US007045351B2

(12) United States Patent
Lambeth et al.

(10) Patent No.: US 7,045,351 B2
(45) Date of Patent: May 16, 2006

(54) MITOGENIC OXYGENASES

(75) Inventors: J. David Lambeth, Decatur, GA (US); Kathy K. Griendling, Stone Mountain, GA (US); Bernard P. Lassegue, Decatur, GA (US); Rebecca S. Arnold, Lilburn, GA (US); Guangie Cheng, Lilburn, GA (US)

(73) Assignee: Emory University, Atlanta, GA (US)

( * ) Notice: Subject to any disclaimer, the term of this patent is extended or adjusted under 35 U.S.C. 154(b) by 344 days.

(21) Appl. No.: 10/318,906

(22) Filed: Dec. 13, 2002

(65) Prior Publication Data

US 2003/0157678 A1 Aug. 21, 2003

Related U.S. Application Data

(63) Continuation of application No. 09/437,568, filed on Nov. 10, 1999, now Pat. No. 6,620,603.

(60) Provisional application No. 60/151,242, filed on Aug. 27, 1999, provisional application No. 60/149,332, filed on Aug. 17, 1999, provisional application No. 60/107,911, filed on Nov. 10, 1998.

(51) Int. Cl.
*C12N 5/00* (2006.01)
*C12N 9/02* (2006.01)
*C12N 9/08* (2006.01)
*C12N 15/52* (2006.01)
*C07H 21/04* (2006.01)

(52) U.S. Cl. .................. 435/325; 435/189; 435/192; 435/252.3; 435/320.1; 536/23.2

(58) Field of Classification Search ................ 435/325, 435/189, 192, 252.3, 320.1; 536/23.2
See application file for complete search history.

(56) References Cited

U.S. PATENT DOCUMENTS

| 4,690,914 | A  | 9/1987  | Callut et al. |
| 5,585,103 | A  | 12/1996 | Raychaudhuri et al. |
| 5,593,966 | A  | 1/1997  | Malech et al. |
| 5,733,748 | A  | 3/1998  | Yu et al. |
| 5,929,033 | A  | 7/1999  | Tang et al. |
| 5,985,270 | A  | 11/1999 | Srivastava |
| 6,620,603 | B1 | 9/2003  | Lambeth et al. |
| 6,858,386 | B1 | 2/2005  | Macina et al. |
| 2003/0044783 | A1 | 3/2003 | Williams et al. |
| 2003/0109690 | A1 | 6/2003 | Ruben et al. |

FOREIGN PATENT DOCUMENTS

WO    WO 99/60161    11/1999

OTHER PUBLICATIONS

Edens et al. (2001) J. Cell Biology, vol. 154(4), pp. 879-891.*

U.S. Appl. No. 60/086,266, filed May 21, 1998, Macina et al.

International Search Report dated Aug. 16, 2000 for PCT/US 99/26592.

Li, F. et al.: "CD34+ Peripheral Blood Progenitors as a Target for Genetic Correction of the Two Flavocytochrome B558 Defective Forms of Chronic Granulomatous Disease," Blood, US, W.B. Saunders, Philadelphia, VA, vol. 84, No. 1, Jul. 1, 1994, pp. 53-58, XP000674233 ISSN: 0006-4971, p. 54, col. 2, figures 1, 2.

Strausberg et al., "National cancer institute, cancer genome anatomy project (CGAP)," EMBL Database Acc No.: AA493362, Jun. 28, 1997, XP002137597.

Lloyd: "Human DNA sequence from clone 146h21 on chromosome Xq22," EMBL Database Acc No.: Z83819, Jan. 10, 1997, XP002137598.

Adams et al.: "Initial assessment of human gene diversity and expression patterns based upon 83 million basepairs of cDNA sequence," EMBL Database Acc No.: AA305700, Apr. 18, 1997, XP002137621 cited in the application.

Palmer: "Human DNA sequence from clone 257I9 on chromosome 6q25.1-26 contains gene similar to Cytochrome B, CA repeat, GSS" EMBL Database Acc. No.: AL031773, Sep. 29, 1998, XP002144975.

Hillier et al.: "Generation and analysis of 280,000 human expressed sequence tags," EMBL Database Acc. No.: W52750, Jun. 4, 1996, XP002144976.

Strausberg: "National cancer institute, cancer genome anatomy project (CGAP)" EMBL Database Acc. No.: AA641653, Nov. 1, 1997, XP002144977.

Wilson et al.: "f53g12.3" EMBL Database Acc. No.: AF003139, Jul. 1, 1997, XP002144978, abstract.

Suh et al.: "Cell transformation by the superoxide-generating oxidase Mox1" Nature, vol. 401, Sep. 2, 1999, pp. 79-82, XP002137599.

Dupuy et al.: "Purification of a novel flavoprotein involved in the thyroid NADPH oxidase," The Journal of Biological Chemistry, vol. 274, No. 52, Dec. 24, 1999, pp. 37265-37269, XP002144979.

(Continued)

*Primary Examiner*—Elizabeth Slobodyansky
(74) *Attorney, Agent, or Firm*—Klarquist Sparkman LLP

(57) ABSTRACT

The present invention relates to new genes encoding for the production of novel proteins involved in generation of reactive oxygen intermediates that affect cell division. The present invention also provides vectors containing these genes, cells transfected with these vectors, antibodies raised against these novel proteins, kits for detection, localization and measurement of these genes and proteins, and methods to determine the activity of drugs to affect the activity of the proteins of the present invention.

9 Claims, 8 Drawing Sheets

OTHER PUBLICATIONS

Dupuy et al.: EMBL Database Acc. No.: AF181972, Dec. 29, 1999, XP002144980.

Abdelrahim, M., et al., "Liquid chromatographic assay of dityrosin in human cerebrospinal fluid," J. Chromatogr. B. Biomed. Sci. Appl., vol. 696, pp. 175-182 (1997).

Anderson, S.O., "Covalent cross-links in a structural protein, resilin," Acta Physiol. Scand., vol. 66 Suppl. 263, pp. 1-81 (1966).

Burdon, R.H., "Superoxide and hydrogen peroxide in relation to mammalian cell proliferation," Free Radical Biol. Med., vol. 18, No. 4, pp. 775-794 (1995).

Church, S.L., et al., "Increased managanese superoxide dismutase expression suppresses the malignant phenotype of human melanoma cells," Proc. Natl. Acad. Sci. USA, vol. 90, pp. 3113-3117 (1993).

Emmendörffer, A., et al., "Production of oxygen radicals by fibroblasts and neutrophils from a patient with x-linked chronic granulomatous disease," Eur. J. Haematol, vol. 51, pp. 223-227 (1993).

Fernandez-Pol, J.A., et al., "Correlation between the loss of the transformed phenotype and an increase in superoxide dismutase activity in a revertant subclone of sarcoma virus-infected mammalian cells," Can. Res., vol. 42, pp. 609-617 (1982).

Fire, A., et al., "Potent and specific genetic interference by double-stranded RNA in Caenorhabditis elegans," Nature, vol. 391, No. 6669, pp. 806-811 (1998).

Frohman, M.A., et al., "Rapid production of full-length cDNAs from rare transcripts: Amplification using a single gene-specific oligonucleotide primer," Proc. Natl. Acad. Sci. USA, vol. 85, pp. 8998-9002 (1988).

Fukui, T., et al., "p22phox mRNA expression and NADPH oxidase activity are increased in aortas from hypertensive rats," Cir. Res., vol. 80, No. 1, pp. 45-51 (1997).

Gardner, P.R., et al., "Superoxide radical and iron modulate aconitase activity in mammalian cells," J. Biol. Chem., vol. 270, No. 22, pp. 13399-13405 (1995).

Griendling, K. K., et al., "Angiotensin II stimulates NADH and NADPH oxidase activity in cultured vascular smooth muscle cells," Cir. Res., vol. 74, No. 6, pp. 1141-1148 (1994).

Irani, K., et al., "Mitogenic signaling mediated by oxidants in ras-transformed fibroblasts," Science, vol. 275, No. 5306, pp. 1649-1652 (1997).

Li, Y., et al., "Validation of lucigenin (Bis-N-methylacridinium) as a chemilumigenic probe for detecting superoxide anion radical production by enzymatic and cellular systems," J. Biol. Chem., vol. 273, No. 4, pp. 2015-2023 (1998).

Mastsubara, T., et al., "Increased superoxide anion release from human endothelial cells in response to cytokines," J. Immun., vol. 137, No. 10, pp. 3295-3298 (1986).

Meier, B., et al., "Human fibroblasts release reactive oxygen species in response to interleukin-1 or tumor necrosis factor-α," Biochem. J., vol. 263, No. 2, pp. 539-545, (1989).

Pagano, P. J., et al., "Localization of a constitutively active, phagocyte-like NADPH oxidase in rabbit aortic adventitia: Enhancement by angiotensin II," Proc. Natl. Acad. Sci. USA, vol. 94, No. 26, pp. 14483-14488 (1997).

Schmidt, K. N., et al., "The roles of hydrogen peroxide and superoxide as messengers in the activation of transcription factor NF-κB," Chem. & Bio., vol. 2, No. 1, pp. 13-22 (1995).

Schreck, R., et al., "Reactive oxygen intermediates as apparently widely used messengers in the activation of the NF-κB transcription factor and HIV-1," EMBO J., vol. 10, No. 8, pp. 2247-2258 (1991).

Suh, Y., et al., "Cell transformation by the superoxide-generating oxidase Mox1," Nature, vol. 401, No. 6748, pp. 79-82 (1999).

Sundaresan, M., et al., "Requirement for generation of $H_2O_2$ for platelet-derived growth factor signal transduction," Science, vol. 270, pp. 296-299 (1995).

Szatrowski, T.P., et al., "Production of large amounts of hydrogen peroxide by human tumor cells," Canc. Res., vol. 51, No. 3, pp. 794-798 (1991).

Uhlinger, D.J., "Nucleoside triphosphate requirements for superoxide generation and phosphorylation in a cell-free system from human neutrophils," vol. 266, No. 31, pp. 20990-20997 (1991).

Ushio-Fukai M., et al., "p22$^{phox}$ is a critical component of the superoxide-generating NADH/NADPH oxidase system and regulates angiotensin II-induced hypertrophy in vascular smooth muscle cells," J. Biol. Chem., vol. 271, No. 38, pp. 23317-23321 (1996).

Yan, T., et al., "Manganese-containing superoxide dismutase overexpression causes phenotypic reversion in SV40-transformed human lung fibroblasts," Canc. Res., vol. 56, pp. 2864-2871 (1996).

Yu, L., et al., Biosynthesis of the phagocyte NADPH oxidase cytochrome $b_{558}$, J. Biol. Chem., vol. 272, No. 43, pp. 27288-27294 (1997).

Zhou et al., "Interleukin-4 Suppresses the Expression of Macrophage NADPH Oxidase Heavy Chain Subunit (gp91-phox)," *Biochimica et Biophysica Acta*, vol. 1265, pp. 40-48, 1995.

* cited by examiner

FIGURE 1(a)

```
154 F A R K I K N P E G G L Y L A V T L L A G I T G V V I T L    gp91phox.human
155 F V R Q R I K N P E G G L Y V A V T R L A G I T G V V I T L    gp91phox.bovine
155 F A R E K I K N P E G G L Y V A V T R L A G I T G I V I T L    gp91phox.mouse
157 P I Q S R - - - N T T V E Y V T F T S V A G L T G V I M T I    Mox1.human
156 P I Q S P - - - N V T V M Y A F T S I A G L T G V V A T V    Mox1.rat
156 P V R T F P T N T T T E L R T I - - - A G V T G L V I S L    mox2.human
169 - - - - - - - - - - - - - M K G T D G W T G V T M V V    cytb558/arabidopsis.pep
162 - - - - - - - - - - - - - V K G V E G I T G V I M V V    cytb558.rice.pep 184 C L I L I I T S S T K T I R R S Y - - - - - - - - - - - - F    gp91phox.human
185 C L I L I I T S S T K T I R R S Y - - - - - - - - - - - - F    gp91phox.bovine
185 C L I L I I T S S T K T I R R S Y - - - - - - - - - - - - F    gp91phox.mouse
184 A L I L M V T S A T E F I R R S Y - - - - - - - - - - - - F    Mox1.human
183 A L V L M V T S A M E F I R R N Y - - - - - - - - - - - - F    Mox1.rat
183 A L V L I M T S S T E F I R Q A S - - - - - - - - - - - - Y    mox2.human
183 L M L V A Y V L A Q S W F R R N R A N L P K S L K R L T G F    cytb558/arabidopsis.pep
176 C M I I A F T L A T R W F R R S L V K L P R P F D K L T G F    cytb558.rice.pep 202 E V F W Y T H H L F V I F F I G L A I H G A E R I V R G Q T    gp91phox.human
203 E V F W Y T H H L F V I F F I G L A I H G A Q R I V R G Q T    gp91phox.bovine
203 E V F W Y T H H L F V I F F I G L A I H G A E R I V R G Q T    gp91phox.mouse
202 E V F W Y T H H L F I F Y I L G L G I H G I G G I V R G Q T    Mox1.human
201 E L F W Y T H H L F I I Y I I C L G I H G L G G I V R G Q T    Mox1.rat
201 E L F W Y T H H V F I V F L S L A I H G T G R I V R G Q T    mox2.human
213 N A F W Y S H H L F V I V Y V L L I V H G - - - - - - - - -    cytb558/arabidopsis.pep
206 N A F W Y S H H L F I I V Y I A L I V H G - - - - - - - - -    cytb558.rice.pep 232 A E S L A V H N I T V C E Q K I S E W G K I K - E C P I P Q    gp91phox.human
233 A E S L L K H Q P R N C Y Q N I S Q W G K I E - N C P I P E    gp91phox.bovine
233 A E S L E E H N L D I C A D K I E E W G K I K - E C P V P K    gp91phox.mouse
232 E E S M N E S H P R K C A E S F E M W D D R D S H C R R P K    Mox1.human
231 E L E S M S E S H P R N C S Y S F H E W D K Y E R S C R S P H    Mox1.rat
231 Q D S L S L H N I T F C R D R Y A E W Q T V A - Q C P V P Q    mox2.human
234 - - - - - - - - - - Y F V Y L S K E W - - - - - - - - - - -    cytb558/arabidopsis.pep
227 - - - - - - - - - - E C L Y L I H V W - - - - - - - - - - -    cytb558.rice.pep 261 F A G N P P M T W K W I V G P M F L Y L C E R L V R F W R S    gp91phox.human
262 F S G N P P M T W K W I V G P M F L Y L C E R L V R F W R S    gp91phox.bovine
262 F A G N P P M T W K W I V G P M F L Y L C E R L V R F W R S    gp91phox.mouse
262 F E G H P P E S W K W I L A P V I L Y I C E R I L R F Y R S    Mox1.human
261 F V G Q P P E S W K W I L A P I A F Y I F E R I L R F Y R S    Mox1.rat
260 F S G K E P S A W K W I L G P V V L Y A C E R I I R F W R F    mox2.human
243 - - - Y H K T T W M Y L A V P V L L Y A F E R L I R A F R P    cytb558/arabidopsis.pep
236 - - - Y R R T T W M Y L S V P V C L Y V G E R I L R F F R S    cytb558.rice.pep 291 Q Q K V V - I T K V V T H P F K T I E L Q M K K - K G F K M    gp91phox.human
292 Q Q K V V - I T K V V T H P F K T I E L Q M K K - K G F K M    gp91phox.bovine
292 Q Q K V V - I T K V V T H P F K T I E L Q M K K - K G F K M    gp91phox.mouse
292 Q Q K V V - I T K V V M H P S K V L E L Q M N K - R G F S M    Mox1.human
291 R Q K V V - I T K V V M H P C K V L E L Q M R K - R G F T M    Mox1.rat
290 Q Q E V V - I T K V V S H P S G V L E L H M K K - R G F K M    mox2.human
270 G A K A V K V L K V A V Y P G N V L S L Y M S K P K G F K Y    cytb558/arabidopsis.pep
263 G S Y S V R L L K V A I Y P G N V L T L Q M S K P P T F R Y    cytb558.rice.pep
```

FIGURE 1(b)

```
319 E V G Q Y I F V K C P K V S K L E W H P F T L T S A P E E D   gp91phox.human
320 E V G Q Y I F V K C P V V S K L E W H P F T L T S A P E E D   gp91phox.bovine
320 E V G Q Y I F V K C P K V S K L E W H P F T L T S A P E E D   gp91phox.mouse
320 E V G Q Y I F V N C P S I S L L E W H P F T L T S A P E E D   Mox1.human
319 G I G Q Y I F V N C P S I S F L E W H P F T L T S A P E E E   Mox1.rat
318 A P G Q Y I L V Q C P A I S S L E W H P F T L T S A P Q E D   mox2.human
300 T S G Q Y I Y I N C S D V S P L Q W H P F S I T S A S G D D   cytb558/arabidopsis.pep
293 K S G Q Y M F V Q C P A V S P F E W H P F S I T S A P G D D   cytb558.rice.pep 349 F F S I H I R I V G D W T E G L F N A C G - - C - - - - - -   gp91phox.human
350 F F S I H I R I V G D W T E G L F K A C G - - C - - - - - -   gp91phox.bovine
350 F F S I H I R I V G D W T E G L F N A C G - - C - - - - - -   gp91phox.mouse
350 F F S I H I R A A G D W T E N L I R A F E - - - - - - - -   Mox1.human
349 F F S I H I R A A G D W T E N L I R T F E - - - - - - - -   Mox1.rat
348 F F S V H I R A A G D W T A A L L E A F G - - A - - - - - -   mox2.human
330 Y L S V H I R T L G D W T S Q L K S L Y S K V C Q L P S T S   cytb558/arabidopsis.pep
323 Y L S I H V R Q L G D W T R E L K R V F A A A C E P P A G G   cytb558.rice.pep 371 - - - - - - - D K Q E F Q D A W K L P K I A V D G P F G T A   gp91phox.human
372 - - - - - - - D K Q E F Q D A W K L P K I A V D G P F G T A   gp91phox.bovine
372 - - - - - - - D K Q E F Q D A W K L P K I A V D G P F G T A   gp91phox.mouse
371 - - - - - - - - - - - Q Q Y S P I P R I E V D G P F G T A   Mox1.human
370 - - - - - - - - - - - Q Q H S P M P R I E V D G P F G T V   Mox1.rat
370 - - - - - - - E G Q A L Q E P W S L P R L A V D G P F G T A   mox2.human
360 Q S G L F I A D I G Q A N N I T R F P R L L I D G P Y G A P   cytb558/arabidopsis.pep
353 K S G L L R A D - E T T K K I - - L P K L L I D G P Y G S P   cytb558.rice.pep 394 S E D V F S Y E V V M L V G A G I G V T P F A S I L K S V W   gp91phox.human
395 S E D V F S Y E V V M L V G A G I G V T P F A S I L K S V W   gp91phox.bovine
395 S E D V F S Y E V V M L V G A G I G V T P F A S I L K S V W   gp91phox.mouse
389 S E D V F Q Y E V A V L V G A G I G V T P F A S I L K S I W   Mox1.human
388 S E D V F Q Y E V A V L V G A G I G V T P F A S F L K S I W   Mox1.rat
393 L T D V F H Y P V C V C V A G I G V T P F A L L K S I W   mox2.human
390 A Q D Y R N Y D V L L L V G L G I G A T P L I S I I R D V L   cytb558/arabidopsis.pep
380 A Q D Y S K Y D V L L L V G L G I G A T P F I S I L K D L L   cytb558.rice.pep 424 Y K Y C N N A T N - - - - - - - - - - - - - - - - - - -   gp91phox.human
425 Y K Y C N K A P N - - - - - - - - - - - - - - - - - - -   gp91phox.bovine
425 Y K Y C D N A T S - - - - - - - - - - - - - - - - - - -   gp91phox.mouse
419 Y K F Q C A D H N - - - - - - - - - - - - - - - - - - -   Mox1.human
418 Y K F Q R A H N K - - - - - - - - - - - - - - - - - - -   Mox1.rat
423 Y K C S E A Q T P - - - - - - - - - - - - - - - - - - -   mox2.human
420 N N I - - - - - - - - - - - - - - - K N Q N S I E R G   cytb558/arabidopsis.pep
410 N N I I K M E E E E D A S T D L Y P P M G R N N P H V D L G   cytb558.rice.pep 433 - - - - - - - - - - - - L K L K K I Y F Y W L C R D T H A F   gp91phox.human
434 - - - - - - - - - - - - L R L K K I Y F Y W L C R D T H A F   gp91phox.bovine
434 - - - - - - - - - - - - L K L K K I Y F Y W L C R D T H A F   gp91phox.mouse
428 - - - - - - - - - - - - L K T K K I Y F Y W I C R E T G A F   Mox1.human
427 - - - - - - - - - - - - L K T Q K I Y F Y W I C R E T G A F   Mox1.rat
432 - - - - - - - - - - - - L K L S K V Y F Y W I C R D A R A F   mox2.human
432 T N Q H I - - - - K N Y V A T K R A Y F Y W V T R E Q G S L   cytb558/arabidopsis.pep
440 T L M T I T S R P K K I L K T T N A Y F Y W V T R E Q G S F   cytb558.rice.pep
```

FIGURE 1(c)

```
451 E W F A D L L Q L L E S Q M Q E R N N A G F L S Y - - N I Y    gp91phox.human
452 E W F A D L L Q L L E T Q M Q E K N N T D F L S Y - - N I C    gp91phox.bovine
452 E W F A D L L Q L L E T Q M Q E R N N A N F L S Y - - N I Y    gp91phox.mouse
446 S W F N N L L T S L E Q E M E E L G K V G F L N Y - - R L F    Mox1.human
445 A W F N N L L N S L E Q E M D E L G K P D F L N Y - - R L F    Mox1.rat
450 E W F A D L L L S L E T R M S E Q G K T H F L S Y - - H I F    mox2.human
458 E W F S E V M N E V - A E Y D S E G M I E L H N Y C T S V Y    cytb558/arabidopsis.pep
470 D W F K G V M N E I - A D L D Q R N I I E M H N Y L T S V Y    cytb558.rice.pep 479 L T G - - W D E S Q A N H F A V H H D E E K - D V I T G L K    gp91phox.human
480 L T G - - W D E S Q A S H F A M H H D E E K - D V I T G L K    gp91phox.bovine
480 L T G - - W D E S Q A N H F A V H H D E E K - D V I T G L K    gp91phox.mouse
474 L T G - - W D S N I V G H A A L N F D K A T - D I V T G L K    Mox1.human
473 L T G - - W D S N I A G H A A L N F D R A T - D V L T G L K    Mox1.rat
478 L T G - - W D E N Q A L H I A L H W D E N T - D V I T G L K    mox2.human
487 E E G D A R S A L I T M L Q S L H H A K S G I D I V S G T R    cytb558/arabidopsis.pep
499 E E G D A R S A L I T M L Q A L N H A K N G V D I V S G T K    cytb558.rice.pep 506 Q K T L Y G R P N W D N E F K T I A S Q H P N T R I G V F L    gp91phox.human
507 Q K T L Y G R P N W D N E F K T I G S Q H P N T R I G V F L    gp91phox.bovine
507 Q K T L Y G R P N W D N E F K T I A S E H P N T T I G V F L    gp91phox.mouse
501 Q K T S F G R P M W D N E F S T I A T S H P K S V V G V F L    Mox1.human
500 Q K T S F G R P M W D N E F S R I A T A H P K S V V G V F L    Mox1.rat
505 Q K T F Y G R P N W N E F K Q I A Y N H P S S S I G V F F    mox2.human
517 V R T H F A R P N W R S V F K H V A V N H V N Q R V G V F Y    cytb558/arabidopsis.pep
529 V R T H F A R P N W R K V L S K I S S K H P Y A K I G V F Y    cytb558.rice.pep 536 C G P E A L A E T L S K Q S I S N S E S G P R G V H F I F N    gp91phox.human
537 C G P E A L A D T L N K Q C I S N S D S G P R G V H F I F N    gp91phox.bovine
537 C G P E A L A E T L S K Q S I S N S E S G P R G V H F I F N    gp91phox.mouse
531 C G P R T L A K S L R K C H R Y S S L D P R K V Q F Y F N    Mox1.human
530 C G P P T L A K S L R K C R R Y S S L D P R K V Q F Y F N    Mox1.rat
535 C G P K A L S R T L Q K M C H L Y S S A D P R G V H F Y Y N    mox2.human
547 C G N T C I I G E L K R L A Q D F S R K T - - T T K F E F H    cytb558/arabidopsis.pep
559 C G A P V L A Q E L S K L C H E F N G K C - - T T K F D F H    cytb558.rice.pep 566 K E N F    gp91phox.human
567 K E N F    gp91phox.bovine
567 K E N F    gp91phox.mouse
561 K E N - F  Mox1.human
560 K E T F    Mox1.rat
565 K E S F    mox2.human
575 K E N F    cytb558/arabidopsis.pep
587 K E H F    cytb558.rice.pep
```

Decoration 'Decoration #1': Box residues that match the Consensus exactly.

FIGURE 1(d)

SEQUENCE LISTING

<160> NUMBER OF SEQ ID NOS: 61

<210> SEQ ID NO 1
<211> LENGTH: 2609
<212> TYPE: DNA
<213> ORGANISM: Homo sapiens
<220> FEATURE:
<221> NAME/KEY: modified_base
<222> LOCATION: (2025)
<223> OTHER INFORMATION: n at position 2025 = any nucleotide
<220> FEATURE:
<221> NAME/KEY: modified_base
<222> LOCATION: (2036)
<223> OTHER INFORMATION: n at position 2036 = any nucleotide
<220> FEATURE:
<221> NAME/KEY: modified_base
<222> LOCATION: (2164)
<223> OTHER INFORMATION: n at position 2164 = any nucleotide
<220> FEATURE:
<221> NAME/KEY: modified_base
<222> LOCATION: (2264)
<223> OTHER INFORMATION: n at position 2264 = any nucleotide
<220> FEATURE:
<221> NAME/KEY: CDS
<222> LOCATION: (207)..(1901)

<400> SEQUENCE: 1

```
gctgatagca cagttctgtc cagagaagga aggcggaata aacttattca ttcccaggaa      60
ctcttggggt aggtgtgtgt ttttcacatc ttaaaggctc acagaccctg cgctggacaa     120
atgttccatt cctgaaggac ctctccgaaa tccggattgc tgaatcttcc ctgttgccta     180
gaagggctcc aaaccacctc ttgaca atg gga aac tgg gtg gtt aac cac tgg      233
                              Met Gly Asn Trp Val Val Asn His Trp
                                1               5 ttt tca gtt ttg ttt ctg gtt gtt tgg tta ggg ctg aat gtt ttc ctg       281
Phe Ser Val Leu Phe Leu Val Val Trp Leu Gly Leu Asn Val Phe Leu
 10              15                  20                  25 ttt gtg gat gcc ttc ctg aaa tat gag aag gcc gac aaa tac tac tac       329
Phe Val Asp Ala Phe Leu Lys Tyr Glu Lys Ala Asp Lys Tyr Tyr Tyr
                 30                  35                  40 aca aga aaa atc ctt ggg tca aca ttg gcc tgt gcc cga gcg tct gct       377
Thr Arg Lys Ile Leu Gly Ser Thr Leu Ala Cys Ala Arg Ala Ser Ala
             45                  50                  55 ctc tgc ttg aat ttt aac agc acg ctg atc ctg ctt cct gtg tgt cgc       425
Leu Cys Leu Asn Phe Asn Ser Thr Leu Ile Leu Leu Pro Val Cys Arg
 60                  65                  70 aat ctg ctg tcc ttc ctg agg ggc acc tgc tca ttt gca agc cgc aca       473
Asn Leu Leu Ser Phe Leu Arg Gly Thr Cys Ser Phe Ala Ser Arg Thr
         75                  80                  85 ctg aga aag caa ttg gat cac aac ctc acc ttc cac aag ctg gtg gcc       521
Leu Arg Lys Gln Leu Asp His Asn Leu Thr Phe His Lys Leu Val Ala
 90                  95                 100                 105 tat atg atc tgc cta cat aca gct att cac atc att gca cac ctg ttt       569
Tyr Met Ile Cys Leu His Thr Ala Ile His Ile Ile Ala His Leu Phe
                110                 115                 120 aac ttt gac tgc tat agc aga agc cga cag gcc aca gat ggc tcc ctt       617
Asn Phe Asp Cys Tyr Ser Arg Ser Arg Gln Ala Thr Asp Gly Ser Leu
            125                 130                 135 gcc tcc att ctc tcc agc cta tct cat gat gag aaa aag ggg ggt tct       665
Ala Ser Ile Leu Ser Ser Leu Ser His Asp Glu Lys Lys Gly Gly Ser
        140                 145                 150 tgg cta aat ccc atc cag tcc cga aac acg aca gtg gag tat gtg aca       713
Trp Leu Asn Pro Ile Gln Ser Arg Asn Thr Thr Val Glu Tyr Val Thr
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 155 |     |     |     |     | 160 |     |     |     |     | 165 |     |     |     |      |
| ttc | acc | agc | gtt | gct | ggt | ctc | act | gga | gtg | atc | atg | aca | ata | gcc | ttg | 761  |
| Phe | Thr | Ser | Val | Ala | Gly | Leu | Thr | Gly | Val | Ile | Met | Thr | Ile | Ala | Leu |      |
| 170 |     |     |     |     | 175 |     |     |     |     | 180 |     |     |     |     | 185 |      |
| att | ctc | atg | gta | act | tca | gct | act | gag | ttc | atc | cgg | agg | agt | tat | ttt | 809  |
| Ile | Leu | Met | Val | Thr | Ser | Ala | Thr | Glu | Phe | Ile | Arg | Arg | Ser | Tyr | Phe |      |
|     |     |     |     | 190 |     |     |     |     | 195 |     |     |     |     | 200 |     |      |
| gaa | gtc | ttc | tgg | tat | act | cac | cac | ctt | ttt | atc | ttc | tat | atc | ctt | ggc | 857  |
| Glu | Val | Phe | Trp | Tyr | Thr | His | His | Leu | Phe | Ile | Phe | Tyr | Ile | Leu | Gly |      |
|     |     |     |     | 205 |     |     |     |     | 210 |     |     |     |     | 215 |     |      |
| tta | ggg | att | cac | ggc | att | ggt | gga | att | gtc | cgg | ggt | caa | aca | gag | gag | 905  |
| Leu | Gly | Ile | His | Gly | Ile | Gly | Gly | Ile | Val | Arg | Gly | Gln | Thr | Glu | Glu |      |
|     |     |     |     | 220 |     |     |     |     | 225 |     |     |     |     | 230 |     |      |
| agc | atg | aat | gag | agt | cat | cct | cgc | aag | tgt | gca | gag | tct | ttt | gag | atg | 953  |
| Ser | Met | Asn | Glu | Ser | His | Pro | Arg | Lys | Cys | Ala | Glu | Ser | Phe | Glu | Met |      |
|     | 235 |     |     |     |     | 240 |     |     |     |     | 245 |     |     |     |     |      |
| tgg | gat | gat | cgt | gac | tcc | cac | tgt | agg | cgc | cct | aag | ttt | gaa | ggg | cat | 1001 |
| Trp | Asp | Asp | Arg | Asp | Ser | His | Cys | Arg | Arg | Pro | Lys | Phe | Glu | Gly | His |      |
| 250 |     |     |     |     | 255 |     |     |     |     | 260 |     |     |     |     | 265 |      |
| ccc | cct | gag | tct | tgg | aag | tgg | atc | ctt | gca | ccg | gtc | att | ctt | tat | atc | 1049 |
| Pro | Pro | Glu | Ser | Trp | Lys | Trp | Ile | Leu | Ala | Pro | Val | Ile | Leu | Tyr | Ile |      |
|     |     |     |     | 270 |     |     |     |     | 275 |     |     |     |     | 280 |     |      |
| tgt | gaa | agg | atc | ctc | cgg | ttt | tac | cgc | tcc | cag | cag | aag | gtt | gtg | att | 1097 |
| Cys | Glu | Arg | Ile | Leu | Arg | Phe | Tyr | Arg | Ser | Gln | Gln | Lys | Val | Val | Ile |      |
|     |     |     |     | 285 |     |     |     |     | 290 |     |     |     |     | 295 |     |      |
| acc | aag | gtt | gtt | atg | cac | cca | tcc | aaa | gtt | ttg | gaa | ttg | cag | atg | aac | 1145 |
| Thr | Lys | Val | Val | Met | His | Pro | Ser | Lys | Val | Leu | Glu | Leu | Gln | Met | Asn |      |
|     |     |     | 300 |     |     |     |     | 305 |     |     |     |     | 310 |     |     |      |
| aag | cgt | ggc | ttc | agc | atg | gaa | gtg | ggg | cag | tat | atc | ttt | gtt | aat | tgc | 1193 |
| Lys | Arg | Gly | Phe | Ser | Met | Glu | Val | Gly | Gln | Tyr | Ile | Phe | Val | Asn | Cys |      |
|     | 315 |     |     |     |     | 320 |     |     |     |     | 325 |     |     |     |     |      |
| ccc | tca | atc | tct | ctc | ctg | gaa | tgg | cat | cct | ttt | act | ttg | acc | tct | gct | 1241 |
| Pro | Ser | Ile | Ser | Leu | Leu | Glu | Trp | His | Pro | Phe | Thr | Leu | Thr | Ser | Ala |      |
| 330 |     |     |     |     | 335 |     |     |     |     | 340 |     |     |     |     | 345 |      |
| cca | gag | gaa | gat | ttc | ttc | tcc | att | cat | atc | cga | gca | gca | ggg | gac | tgg | 1289 |
| Pro | Glu | Glu | Asp | Phe | Phe | Ser | Ile | His | Ile | Arg | Ala | Ala | Gly | Asp | Trp |      |
|     |     |     |     | 350 |     |     |     |     | 355 |     |     |     |     | 360 |     |      |
| aca | gaa | aat | ctc | ata | agg | gct | ttc | gaa | caa | caa | tat | tca | cca | att | ccc | 1337 |
| Thr | Glu | Asn | Leu | Ile | Arg | Ala | Phe | Glu | Gln | Gln | Tyr | Ser | Pro | Ile | Pro |      |
|     |     |     | 365 |     |     |     |     | 370 |     |     |     |     | 375 |     |     |      |
| agg | att | gaa | gtg | gat | ggt | ccc | ttt | ggc | aca | gcc | agt | gag | gat | gtt | ttc | 1385 |
| Arg | Ile | Glu | Val | Asp | Gly | Pro | Phe | Gly | Thr | Ala | Ser | Glu | Asp | Val | Phe |      |
|     | 380 |     |     |     |     | 385 |     |     |     |     | 390 |     |     |     |     |      |
| cag | tat | gaa | gtg | gct | gtg | ctg | gtt | gga | gca | gga | att | ggg | gtc | acc | ccc | 1433 |
| Gln | Tyr | Glu | Val | Ala | Val | Leu | Val | Gly | Ala | Gly | Ile | Gly | Val | Thr | Pro |      |
|     |     | 395 |     |     |     |     | 400 |     |     |     |     | 405 |     |     |     |      |
| ttt | gct | tct | atc | ttg | aaa | tcc | atc | tgg | tac | aaa | ttc | cag | tgt | gca | gac | 1481 |
| Phe | Ala | Ser | Ile | Leu | Lys | Ser | Ile | Trp | Tyr | Lys | Phe | Gln | Cys | Ala | Asp |      |
| 410 |     |     |     |     | 415 |     |     |     |     | 420 |     |     |     |     | 425 |      |
| cac | aac | ctc | aaa | aca | aaa | aag | atc | tat | ttc | tac | tgg | atc | tgc | agg | gag | 1529 |
| His | Asn | Leu | Lys | Thr | Lys | Lys | Ile | Tyr | Phe | Tyr | Trp | Ile | Cys | Arg | Glu |      |
|     |     |     |     | 430 |     |     |     |     | 435 |     |     |     |     | 440 |     |      |
| aca | ggt | gcc | ttt | tcc | tgg | ttc | aac | aac | ctg | ttg | act | tcc | ctg | gaa | cag | 1577 |
| Thr | Gly | Ala | Phe | Ser | Trp | Phe | Asn | Asn | Leu | Leu | Thr | Ser | Leu | Glu | Gln |      |
|     |     |     | 445 |     |     |     |     | 450 |     |     |     |     | 455 |     |     |      |
| gag | atg | gag | gaa | tta | ggc | aaa | gtg | ggt | ttt | cta | aac | tac | cgt | ctc | ttc | 1625 |
| Glu | Met | Glu | Glu | Leu | Gly | Lys | Val | Gly | Phe | Leu | Asn | Tyr | Arg | Leu | Phe |      |
|     | 460 |     |     |     |     | 465 |     |     |     |     | 470 |     |     |     |     |      |
| ctc | acc | gga | tgg | gac | agc | aat | att | gtt | ggt | cat | gca | gca | tta | aac | ttt | 1673 |

-continued

| | | | | | | | | | | | | | |
|---|---|---|---|---|---|---|---|---|---|---|---|---|---|
| Leu | Thr | Gly | Trp | Asp | Ser | Asn | Ile | Val | Gly | His | Ala | Ala | Leu | Asn | Phe |
| | 475 | | | | 480 | | | | 485 | | | | |

```
gac aag gcc act gac atc gtg aca ggt ctg aaa cag aaa acc tcc ttt      1721
Asp Lys Ala Thr Asp Ile Val Thr Gly Leu Lys Gln Lys Thr Ser Phe
490             495                 500                 505 ggg aga cca atg tgg gac aat gag ttt tct aca ata gct acc tcc cac      1769
Gly Arg Pro Met Trp Asp Asn Glu Phe Ser Thr Ile Ala Thr Ser His
            510                 515                 520 ccc aag tct gta gtg gga gtt ttc tta tgt ggc cct cgg act ttg gca      1817
Pro Lys Ser Val Val Gly Val Phe Leu Cys Gly Pro Arg Thr Leu Ala
        525                 530                 535 aag agc ctg cgc aaa tgc tgt cac cga tat tcc agt ctg gat cct aga      1865
Lys Ser Leu Arg Lys Cys Cys His Arg Tyr Ser Ser Leu Asp Pro Arg
    540                 545                 550 aag gtt caa ttc tac ttc aac aaa gaa aat ttt tga gttataggaa           1911
Lys Val Gln Phe Tyr Phe Asn Lys Glu Asn Phe
555                 560                 565 taaggacggt aatctgcatt ttgtctcttt gtatcttcag taattgagtt ataggaataa    1971
ggacggtaat ctgcattttg tctctttgta tcttcagtaa tttacttggt ctcntcaggt    2031
ttgancagtc actttaggat aagaatgtgc ctctcaagcc ttgactccct ggtattcttt    2091
ttttgattgc attcaacttc gttacttgag cttcagcaac ttaagaactt ctgaagttct    2151
taaagttctg aanttcttaa agcccatgga tcctttctca gaaaaataac tgtaaatctt    2211
tctggacagc catgactgta gcaaggcttg atagcagaag tttggtggtt canaattata    2271
caactaatcc caggtgattt tatcaattcc agtgttacca tctcctgagt tttggttttgt   2331 aatcttttgt ccctcccacc cccacagaag attttaagta gggtgacttt ttaaataaaa    2391
atttattgaa taattaatga taaaacataa taataaacat aaataataaa caaaattacc    2451
gagaacccca tccccatata acaccaacag tgtacatgtt tactgtcact tttgatatgg    2511
tttatccagt gtgaacagca atttattatt tttgctcatc aaaaaataaa ggatttttt     2571 tcacttgaaa aaaaaaaaaa aaaaaaaaa aaaaaaa                              2609
```

<210> SEQ ID NO 2
<211> LENGTH: 564
<212> TYPE: PRT
<213> ORGANISM: Homo sapiens

<400> SEQUENCE: 2

| Met | Gly | Asn | Trp | Val | Val | Asn | His | Trp | Phe | Ser | Val | Leu | Phe | Leu | Val |
|---|---|---|---|---|---|---|---|---|---|---|---|---|---|---|---|
| 1 | | | | 5 | | | | | 10 | | | | | 15 | |

| Val | Trp | Leu | Gly | Leu | Asn | Val | Phe | Leu | Phe | Val | Asp | Ala | Phe | Leu | Lys |
|---|---|---|---|---|---|---|---|---|---|---|---|---|---|---|---|
| | | | 20 | | | | | 25 | | | | | 30 | | |

| Tyr | Glu | Lys | Ala | Asp | Lys | Tyr | Tyr | Tyr | Thr | Arg | Lys | Ile | Leu | Gly | Ser |
|---|---|---|---|---|---|---|---|---|---|---|---|---|---|---|---|
| | 35 | | | | | 40 | | | | | 45 | | | | |

| Thr | Leu | Ala | Cys | Ala | Arg | Ala | Ser | Ala | Leu | Cys | Leu | Asn | Phe | Asn | Ser |
|---|---|---|---|---|---|---|---|---|---|---|---|---|---|---|---|
| | 50 | | | | 55 | | | | | 60 | | | | | |

| Thr | Leu | Ile | Leu | Leu | Pro | Val | Cys | Arg | Asn | Leu | Leu | Ser | Phe | Leu | Arg |
|---|---|---|---|---|---|---|---|---|---|---|---|---|---|---|---|
| 65 | | | | | 70 | | | | | 75 | | | | | 80 |

| Gly | Thr | Cys | Ser | Phe | Cys | Ser | Arg | Thr | Leu | Arg | Lys | Gln | Leu | Asp | His |
|---|---|---|---|---|---|---|---|---|---|---|---|---|---|---|---|
| | | | | 85 | | | | | 90 | | | | | 95 | |

| Asn | Leu | Thr | Phe | His | Lys | Leu | Val | Ala | Tyr | Met | Ile | Cys | Leu | His | Thr |
|---|---|---|---|---|---|---|---|---|---|---|---|---|---|---|---|
| | | | 100 | | | | | 105 | | | | | 110 | | |

| Ala | Ile | His | Ile | Ile | Ala | His | Leu | Phe | Asn | Phe | Asp | Cys | Tyr | Ser | Arg |
|---|---|---|---|---|---|---|---|---|---|---|---|---|---|---|---|
| | | 115 | | | | | 120 | | | | | 125 | | | |

-continued

```
Ser Arg Gln Ala Thr Asp Gly Ser Leu Ala Ser Ile Leu Ser Ser Leu
    130                 135                 140

Ser His Asp Glu Lys Lys Gly Gly Ser Trp Leu Asn Pro Ile Gln Ser
145                 150                 155                 160

Arg Asn Thr Thr Val Glu Tyr Val Thr Phe Thr Ser Val Ala Gly Leu
                165                 170                 175

Thr Gly Val Ile Met Thr Ile Ala Leu Ile Leu Met Val Thr Ser Ala
            180                 185                 190

Thr Glu Phe Ile Arg Arg Ser Tyr Phe Glu Val Phe Trp Tyr Thr His
        195                 200                 205

His Leu Phe Ile Phe Tyr Ile Leu Gly Leu Gly Ile His Gly Ile Gly
    210                 215                 220

Gly Ile Val Arg Gly Gln Thr Glu Glu Ser Met Asn Glu Ser His Pro
225                 230                 235                 240

Arg Lys Cys Ala Glu Ser Phe Glu Met Trp Asp Asp Arg Asp Ser His
                245                 250                 255

Cys Arg Arg Pro Lys Phe Glu Gly His Pro Pro Glu Ser Trp Lys Trp
            260                 265                 270

Ile Leu Ala Pro Val Ile Leu Tyr Ile Cys Glu Arg Ile Leu Arg Phe
        275                 280                 285

Tyr Arg Ser Gln Gln Lys Val Val Ile Thr Lys Val Val Met His Pro
    290                 295                 300

Ser Lys Val Leu Glu Leu Gln Met Asn Lys Arg Gly Phe Ser Met Glu
305                 310                 315                 320

Val Gly Gln Tyr Ile Phe Val Asn Cys Pro Ser Ile Ser Leu Leu Glu
                325                 330                 335

Trp His Pro Phe Thr Leu Thr Ser Ala Pro Glu Glu Asp Phe Phe Ser
            340                 345                 350

Ile His Ile Arg Ala Ala Gly Asp Trp Thr Glu Asn Leu Ile Arg Ala
        355                 360                 365

Phe Glu Gln Gln Tyr Ser Pro Ile Pro Arg Ile Glu Val Asp Gly Pro
    370                 375                 380

Phe Gly Thr Ala Ser Glu Asp Val Phe Gln Tyr Glu Val Ala Val Leu
385                 390                 395                 400

Val Gly Ala Gly Ile Gly Val Thr Pro Phe Ala Ser Ile Leu Lys Ser
                405                 410                 415

Ile Trp Tyr Lys Phe Gln Cys Ala Asp His Asn Leu Lys Thr Lys Lys
            420                 425                 430

Ile Tyr Phe Tyr Trp Ile Cys Arg Glu Thr Gly Ala Phe Ser Trp Phe
        435                 440                 445

Asn Asn Leu Leu Thr Ser Leu Glu Gln Glu Met Glu Glu Leu Gly Lys
    450                 455                 460

Val Gly Phe Leu Asn Tyr Arg Leu Phe Leu Thr Gly Trp Asp Ser Asn
465                 470                 475                 480

Ile Val Gly His Ala Ala Leu Asn Phe Asp Lys Ala Thr Asp Ile Val
                485                 490                 495

Thr Gly Leu Lys Gln Lys Thr Ser Phe Gly Arg Pro Met Trp Asp Asn
            500                 505                 510

Glu Phe Ser Thr Ile Ala Thr Ser His Pro Lys Ser Val Val Gly Val
        515                 520                 525

Phe Leu Cys Gly Pro Arg Thr Leu Ala Lys Ser Leu Arg Lys Cys Cys
    530                 535                 540

His Arg Tyr Ser Ser Leu Asp Pro Arg Lys Val Gln Phe Tyr Phe Asn
```

-continued

```
                545                 550                 555                 560
Lys Glu Asn Phe

<210> SEQ ID NO 3
<211> LENGTH: 2044
<212> TYPE: DNA
<213> ORGANISM: Homo sapiens
<220> FEATURE:
<221> NAME/KEY: CDS
<222> LOCATION: (104)..(1810)

<400> SEQUENCE: 3
caaagacaaa ataatttact agggaagccc ttactaacga cccaacatcc agacacaggt         60
gagggagaag aaatttcctg acagccgaag agcaacaagt atc atg atg ggg tgc        115
                                              Met Met Gly Cys
                                                1 tgg att ttg aat gag ggt ctc tcc acc ata tta gta ctc tca tgg ctg        163
Trp Ile Leu Asn Glu Gly Leu Ser Thr Ile Leu Val Leu Ser Trp Leu
  5                  10                  15                  20 gga ata aat ttt tat ctg ttt att gac acg ttc tac tgg tat gaa gag        211
Gly Ile Asn Phe Tyr Leu Phe Ile Asp Thr Phe Tyr Trp Tyr Glu Glu
             25                  30                  35 gag gag tct ttc cat tac aca cga gtt att ttg ggt tca aca ctg gct        259
Glu Glu Ser Phe His Tyr Thr Arg Val Ile Leu Gly Ser Thr Leu Ala
         40                  45                  50 tgg gca cga gca tcc gca ctg tgc ctg aat ttt aac tgc atg cta att        307
Trp Ala Arg Ala Ser Ala Leu Cys Leu Asn Phe Asn Cys Met Leu Ile
 55                  60                  65 cta ata cct gtc agt cga aac ctt att tca ttc ata aga gga aca agt        355
Leu Ile Pro Val Ser Arg Asn Leu Ile Ser Phe Ile Arg Gly Thr Ser
     70                  75                  80 att tgc tgc aga gga ccg tgg agg agg caa tta gac aaa aac ctc aga        403
Ile Cys Cys Arg Gly Pro Trp Arg Arg Gln Leu Asp Lys Asn Leu Arg
 85                  90                  95                 100 ttt cac aaa ctg gtc gcc tat ggg ata gct gtt aat gca acc atc cac        451
Phe His Lys Leu Val Ala Tyr Gly Ile Ala Val Asn Ala Thr Ile His
                105                 110                 115 atc gtg gcg cat ttc ttc aac ctg gaa cgc tac cac tgg agc cag tcc        499
Ile Val Ala His Phe Phe Asn Leu Glu Arg Tyr His Trp Ser Gln Ser
            120                 125                 130 gag gag gcc cag gga ctt ctg gcc gca ctt tcc aag ctg ggc aac acc        547
Glu Glu Ala Gln Gly Leu Leu Ala Ala Leu Ser Lys Leu Gly Asn Thr
        135                 140                 145 cct aac gag agc tac ctc aac cct gtc cgg acc ttc ccc aca aac aca        595
Pro Asn Glu Ser Tyr Leu Asn Pro Val Arg Thr Phe Pro Thr Asn Thr
    150                 155                 160 acc act gaa ttg cta agg aca ata gca ggc gtc acc ggt ctg gtg atc        643
Thr Thr Glu Leu Leu Arg Thr Ile Ala Gly Val Thr Gly Leu Val Ile
165                 170                 175                 180 tct ctg gct tta gtc ttg atc atg acc tcg tca act gag ttc atc aga        691
Ser Leu Ala Leu Val Leu Ile Met Thr Ser Ser Thr Glu Phe Ile Arg
                185                 190                 195 cag gcc tcc tat gag ttg ttc tgg tac aca cac cat gtt ttc atc gtc        739
Gln Ala Ser Tyr Glu Leu Phe Trp Tyr Thr His His Val Phe Ile Val
            200                 205                 210 ttc ttt ctc agc ctg gcc atc cat ggg acg ggt cgg att gtt cga ggc        787
Phe Phe Leu Ser Leu Ala Ile His Gly Thr Gly Arg Ile Val Arg Gly
        215                 220                 225 caa acc caa gac agt ctc tct ctg cac aac atc acc ttc tgt aga gac        835
Gln Thr Gln Asp Ser Leu Ser Leu His Asn Ile Thr Phe Cys Arg Asp
    230                 235                 240
```

```
                                                          -continued cgc tat gca gaa tgg cag aca gtg gcc caa tgc ccc gtg cct caa ttt      883
Arg Tyr Ala Glu Trp Gln Thr Val Ala Gln Cys Pro Val Pro Gln Phe
245                 250                 255                 260 tct ggc aag gaa ccc tcg gct tgg aaa tgg att tta ggc cct gtg gtc      931
Ser Gly Lys Glu Pro Ser Ala Trp Lys Trp Ile Leu Gly Pro Val Val
            265                 270                 275 ttg tat gca tgt gaa aga ata att agg ttc tgg cga ttt caa caa gaa      979
Leu Tyr Ala Cys Glu Arg Ile Ile Arg Phe Trp Arg Phe Gln Gln Glu
        280                 285                 290 gtt gtc att acc aag gtg gta agc cac ccc tct gga gtc ctg gaa ctt     1027
Val Val Ile Thr Lys Val Val Ser His Pro Ser Gly Val Leu Glu Leu
    295                 300                 305 cac atg aaa aag cgt ggc ttt aaa atg gcg cca ggg cag tac atc ttg     1075
His Met Lys Lys Arg Gly Phe Lys Met Ala Pro Gly Gln Tyr Ile Leu
310                 315                 320 gtg cag tgc cca gcc ata tct tcg ctg gag tgg cac ccc ttc acc ctt     1123
Val Gln Cys Pro Ala Ile Ser Ser Leu Glu Trp His Pro Phe Thr Leu
325                 330                 335                 340 acc tct gcc ccc cag gaa gac ttt ttc agc gtg cac atc cgg gca gca     1171
Thr Ser Ala Pro Gln Glu Asp Phe Phe Ser Val His Ile Arg Ala Ala
            345                 350                 355 gga gac tgg aca gca gcg cta ctg gag gcc ttt ggg gca gag gga cag     1219
Gly Asp Trp Thr Ala Ala Leu Leu Glu Ala Phe Gly Ala Glu Gly Gln
        360                 365                 370 gcc ctc cag gag ccc tgg agc ctg cca agg ctg gca gtg gac ggg ccc     1267
Ala Leu Gln Glu Pro Trp Ser Leu Pro Arg Leu Ala Val Asp Gly Pro
    375                 380                 385 ttt gga act gcc ctg aca gat gta ttt cac tac cca gtg tgt gtg tgc     1315
Phe Gly Thr Ala Leu Thr Asp Val Phe His Tyr Pro Val Cys Val Cys
390                 395                 400 gtt gcc gcg ggg atc gga gtc act ccc ttc gct gct ctt ctg aaa tct     1363
Val Ala Ala Gly Ile Gly Val Thr Pro Phe Ala Ala Leu Leu Lys Ser
405                 410                 415                 420 ata tgg tac aaa tgc agt gag gca cag acc cca ctg aag ctg agc aag     1411
Ile Trp Tyr Lys Cys Ser Glu Ala Gln Thr Pro Leu Lys Leu Ser Lys
            425                 430                 435 gtg tat ttc tac tgg att tgc cgg gat gca aga gct ttt gag tgg ttt     1459
Val Tyr Phe Tyr Trp Ile Cys Arg Asp Ala Arg Ala Phe Glu Trp Phe
        440                 445                 450 gct gat ctc tta ctc tcc ctg gaa aca cgg atg agt gag cag ggg aaa     1507
Ala Asp Leu Leu Leu Ser Leu Glu Thr Arg Met Ser Glu Gln Gly Lys
    455                 460                 465 act cac ttt ctg agt tat cat ata ttt ctt acc ggc tgg gat gaa aat     1555
Thr His Phe Leu Ser Tyr His Ile Phe Leu Thr Gly Trp Asp Glu Asn
470                 475                 480 cag gct ctt cac ata gct tta cac tgg gac gaa aat act gac gtg att     1603
Gln Ala Leu His Ile Ala Leu His Trp Asp Glu Asn Thr Asp Val Ile
485                 490                 495                 500 aca ggc tta aag cag aag acc ttc tat ggg agg ccc aac tgg aac aat     1651
Thr Gly Leu Lys Gln Lys Thr Phe Tyr Gly Arg Pro Asn Trp Asn Asn
            505                 510                 515 gag ttc aag cag att gcc tac aat cac ccc agc agc agt att ggc gtg     1699
Glu Phe Lys Gln Ile Ala Tyr Asn His Pro Ser Ser Ser Ile Gly Val
        520                 525                 530 ttc ttc tgt gga cct aaa gct ctc tcg agg aca ctt caa aag atg tgc     1747
Phe Phe Cys Gly Pro Lys Ala Leu Ser Arg Thr Leu Gln Lys Met Cys
    535                 540                 545 cac ttg tat tca tca gct gac ccc aga ggt gtt cat ttc tat tac aac     1795
His Leu Tyr Ser Ser Ala Asp Pro Arg Gly Val His Phe Tyr Tyr Asn
```

-continued

```
                 550                 555                 560
aag gag agc ttc tag actttggagg tcaagtccag gcattgtgtt ttcaatcaag        1850
Lys Glu Ser Phe
565 ttattgattc caaagaactc caccaggaat tcctgtgacg gcctgttgat atgagctccc       1910 agttgggaac tggtgaataa taattaacta ttgtgaacag tacactatac catacttcct      1970 tagcttataa ataacatgtc atatacaaca gaacaaaaac atttactgaa attaaatat       2030 attatgtttc tcca                                                        2044

<210> SEQ ID NO 4
<211> LENGTH: 568
<212> TYPE: PRT
<213> ORGANISM: Homo sapiens

<400> SEQUENCE: 4

Met Met Gly Cys Trp Ile Leu Asn Glu Gly Leu Ser Thr Ile Leu Val
  1               5                  10                  15

Leu Ser Trp Leu Gly Ile Asn Phe Tyr Leu Phe Ile Asp Thr Phe Tyr
             20                  25                  30

Trp Tyr Glu Glu Glu Ser Phe His Tyr Thr Arg Val Ile Leu Gly
         35                  40                  45

Ser Thr Leu Ala Trp Ala Arg Ala Ser Ala Leu Cys Leu Asn Phe Asn
     50                  55                  60

Cys Met Leu Ile Leu Ile Pro Val Ser Arg Asn Leu Ile Ser Phe Ile
 65                  70                  75                  80

Arg Gly Thr Ser Ile Cys Cys Arg Gly Pro Trp Arg Arg Gln Leu Asp
                 85                  90                  95

Lys Asn Leu Arg Phe His Lys Leu Val Ala Tyr Gly Ile Ala Val Asn
            100                 105                 110

Ala Thr Ile His Ile Val Ala His Phe Phe Asn Leu Glu Arg Tyr His
        115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
            180                 185                 190

Glu Phe Ile Arg Gln Ala Ser Tyr Glu Leu Phe Trp Tyr Thr His His
        195                 200                 205

Val Phe Ile Val Phe Phe Leu Ser Leu Ala Ile His Gly Thr Gly Arg
    210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
            260                 265                 270

Gly Pro Val Val Leu Tyr Ala Cys Glu Arg Ile Ile Arg Phe Trp Arg
        275                 280                 285

Phe Gln Gln Glu Val Val Ile Thr Lys Val Val Ser His Pro Ser Gly
    290                 295                 300
```

-continued

Val Leu Glu Leu His Met Lys Lys Arg Gly Phe Lys Met Ala Pro Gly
305                 310                 315                 320

Gln Tyr Ile Leu Val Gln Cys Pro Ala Ile Ser Ser Leu Glu Trp His
            325                 330                 335

Pro Phe Thr Leu Thr Ser Ala Pro Gln Glu Asp Phe Phe Ser Val His
        340                 345                 350

Ile Arg Ala Ala Gly Asp Trp Thr Ala Leu Leu Glu Ala Phe Gly
    355                 360                 365

Ala Glu Gly Gln Ala Leu Gln Glu Pro Trp Ser Leu Pro Arg Leu Ala
370                 375                 380

Val Asp Gly Pro Phe Gly Thr Ala Leu Thr Asp Val Phe His Tyr Pro
385                 390                 395                 400

Val Cys Val Cys Val Ala Ala Gly Ile Gly Val Thr Pro Phe Ala Ala
            405                 410                 415

Leu Leu Lys Ser Ile Trp Tyr Lys Cys Ser Glu Ala Gln Thr Pro Leu
            420                 425                 430

Lys Leu Ser Lys Val Tyr Phe Tyr Trp Ile Cys Arg Asp Ala Arg Ala
        435                 440                 445

Phe Glu Trp Phe Ala Asp Leu Leu Ser Leu Glu Thr Arg Met Ser
    450                 455                 460

Glu Gln Gly Lys Thr His Phe Leu Ser Tyr His Ile Phe Leu Thr Gly
465                 470                 475                 480

Trp Asp Glu Asn Gln Ala Leu His Ile Ala Leu His Trp Asp Glu Asn
            485                 490                 495

Thr Asp Val Ile Thr Gly Leu Lys Gln Lys Thr Phe Tyr Gly Arg Pro
            500                 505                 510

Asn Trp Asn Asn Glu Phe Lys Gln Ile Ala Tyr Asn His Pro Ser Ser
        515                 520                 525

Ser Ile Gly Val Phe Cys Gly Pro Lys Ala Leu Ser Arg Thr Leu
    530                 535                 540

Gln Lys Met Cys His Leu Tyr Ser Ser Ala Asp Pro Arg Gly Val His
545                 550                 555                 560

Phe Tyr Tyr Asn Lys Glu Ser Phe
                565

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
aacaagcgtg gcttcagcat g                                                21

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 6
agcaatattg ttggtcat                                                    18

<210> SEQ ID NO 7
<211> LENGTH: 24
<212> TYPE: DNA

```
<213> ORGANISM: Artificial Sequence
<220> FEATURE:
<223> OTHER INFORMATION: Description of Artificial Sequence: primer

<400> SEQUENCE: 7
gacttgacag aaaatctata aggg                                          24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 8
ttgtaccaga tggatttcaa                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
caggtctgaa acagaaaacc t                                             21

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 10
atgaattctc attaattatt caataaa                                       27

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 11
atctcaaaag actctgcaca                                               20

<210> SEQ ID NO 12
<211> LENGTH: 569
<212> TYPE: PRT
<213> ORGANISM: Homo sapiens

<400> SEQUENCE: 12

Gly Asn Trp Ala Val Asn Glu Gly Leu Ser Ile Phe Ala Ile Leu Val
 1               5                  10                  15

Trp Leu Gly Leu Asn Val Phe Leu Phe Val Trp Tyr Tyr Arg Val Tyr
                20                  25                  30

Asp Ile Pro Pro Lys Phe Phe Tyr Thr Arg Lys Leu Leu Gly Ser Ala
            35                  40                  45

Leu Ala Leu Ala Arg Ala Pro Ala Ala Cys Leu Asn Phe Asn Cys Met
        50                  55                  60

Leu Ile Leu Leu Pro Val Cys Arg Asn Leu Leu Ser Phe Leu Arg Gly
65                  70                  75                  80
```

```
Ser Ser Ala Cys Cys Ser Thr Arg Val Arg Gln Leu Asp Arg Asn
                85                  90                  95

Leu Thr Phe His Lys Met Val Ala Trp Met Ile Ala Leu His Ser Ala
            100                 105                 110

Ile His Thr Ile Ala His Leu Phe Asn Val Glu Trp Cys Val Asn Ala
            115                 120                 125

Arg Val Asn Asn Ser Asp Pro Tyr Ser Val Ala Leu Ser Glu Leu Gly
            130                 135                 140

Asp Arg Gln Asn Glu Ser Tyr Leu Asn Phe Ala Arg Lys Arg Ile Lys
145                 150                 155                 160

Asn Pro Glu Gly Gly Leu Tyr Leu Ala Val Thr Leu Ala Gly Ile
                165                 170                 175

Thr Gly Val Val Ile Thr Leu Cys Leu Ile Leu Ile Thr Ser Ser
            180                 185                 190

Thr Lys Thr Ile Arg Arg Ser Tyr Phe Glu Val Phe Trp Tyr Thr His
        195                 200                 205

His Leu Phe Val Ile Phe Phe Ile Gly Leu Ala Ile His Gly Ala Glu
        210                 215                 220

Arg Ile Val Arg Gly Gln Thr Ala Glu Ser Leu Ala Val His Asn Ile
225                 230                 235                 240

Thr Val Cys Glu Gln Lys Ile Ser Glu Trp Gly Lys Ile Lys Glu Cys
                245                 250                 255

Pro Ile Pro Gln Phe Ala Gly Asn Pro Pro Met Thr Trp Lys Trp Ile
                260                 265                 270

Val Gly Pro Met Phe Leu Tyr Leu Cys Glu Arg Leu Val Arg Phe Trp
            275                 280                 285

Arg Ser Gln Gln Lys Val Val Ile Thr Lys Val Val Thr His Pro Phe
    290                 295                 300

Lys Thr Ile Glu Leu Gln Met Lys Lys Gly Phe Lys Met Glu Val
305                 310                 315                 320

Gly Gln Tyr Ile Phe Val Lys Cys Pro Lys Val Ser Lys Leu Glu Trp
                325                 330                 335

His Pro Phe Thr Leu Thr Ser Ala Pro Glu Glu Asp Phe Phe Ser Ile
            340                 345                 350

His Ile Arg Ile Val Gly Asp Trp Thr Glu Gly Leu Phe Asn Ala Cys
            355                 360                 365

Gly Cys Asp Lys Gln Glu Phe Gln Asp Ala Trp Lys Leu Pro Lys Ile
370                 375                 380

Ala Val Asp Gly Pro Phe Gly Thr Ala Ser Glu Asp Val Phe Ser Tyr
385                 390                 395                 400

Glu Val Val Met Leu Val Gly Ala Gly Ile Gly Val Thr Pro Phe Ala
                405                 410                 415

Ser Ile Leu Lys Ser Val Trp Tyr Lys Tyr Cys Asn Asn Ala Thr Asn
                420                 425                 430

Leu Lys Leu Lys Lys Ile Tyr Phe Tyr Trp Leu Cys Arg Asp Thr His
            435                 440                 445

Ala Phe Glu Trp Phe Ala Asp Leu Leu Gln Leu Leu Glu Ser Gln Met
    450                 455                 460

Gln Glu Arg Asn Asn Ala Gly Phe Leu Ser Tyr Asn Ile Tyr Leu Thr
465                 470                 475                 480

Gly Trp Asp Glu Ser Gln Ala Asn His Phe Ala Val His His Asp Glu
                485                 490                 495

Glu Lys Asp Val Ile Thr Gly Leu Lys Gln Lys Thr Leu Tyr Gly Arg
```

-continued

```
                500               505                510
Pro Asn Trp Asp Asn Glu Phe Lys Thr Ile Ala Ser Gln His Pro Asn
        515                 520                 525

Thr Arg Ile Gly Val Phe Leu Cys Gly Pro Glu Ala Leu Ala Glu Thr
    530                 535                 540

Leu Ser Lys Gln Ser Ile Ser Asn Ser Glu Ser Gly Pro Arg Gly Val
545                 550                 555                 560

His Phe Ile Phe Asn Lys Glu Asn Phe
                565
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 13
ttggctaaat cccatcca                                               18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 14
tgcatgacca acaatattgc t                                           21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 15
caaggtacct cttgaccatg ggaaact                                     27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 16
acgaattcaa gtaaattact gaagata                                     27

<210> SEQ ID NO 17
<211> LENGTH: 26
<212> TYPE: DNA
<213> ORGANISM: Artificial Sequence
<220> FEATURE:
<221> NAME/KEY: modified_base
<222> LOCATION: (3)
<223> OTHER INFORMATION: n at position 3 = inosine
<220> FEATURE:
<221> NAME/KEY: modified_base
<222> LOCATION: (6)
<223> OTHER INFORMATION: n at position 6 = inosine
<220> FEATURE:
<221> NAME/KEY: modified_base
<222> LOCATION: (12)
<223> OTHER INFORMATION: n at position 12 = inosine -continued

```
<220> FEATURE:
<223> OTHER INFORMATION: Description of Artificial Sequence: primer

<400> SEQUENCE: 17
ccngtntgtc gnaatctgct stcctt                                          26

<210> SEQ ID NO 18
<211> LENGTH: 29
<212> TYPE: DNA
<213> ORGANISM: Artificial Sequence
<220> FEATURE:
<221> NAME/KEY: modified_base
<222> LOCATION: (5)
<223> OTHER INFORMATION: n at position 5 = inosine
<220> FEATURE:
<221> NAME/KEY: modified_base
<222> LOCATION: (9)
<223> OTHER INFORMATION: n at position 9 = inosine
<220> FEATURE:
<221> NAME/KEY: modified_base
<222> LOCATION: (11)
<223> OTHER INFORMATION: n at position 11 = inosine
<220> FEATURE:
<223> OTHER INFORMATION: Description of Artificial Sequence: primer

<400> SEQUENCE: 18
tcccngcana nccagtagaa rtagatctt                                       29

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 19
ttggcacagt cagtgaggat gtcttc                                          26

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 20
ctgttggctt ctactgtagc gttcaaagtt                                      30

<210> SEQ ID NO 21
<211> LENGTH: 563
<212> TYPE: PRT
<213> ORGANISM: Rat

<400> SEQUENCE: 21

Met Gly Asn Trp Leu Val Asn His Trp Leu Ser Val Leu Phe Leu Val
  1               5                  10                  15

Ser Trp Leu Gly Leu Asn Ile Phe Leu Phe Val Tyr Val Phe Leu Asn
             20                  25                  30

Tyr Glu Lys Ser Asp Lys Tyr Tyr Tyr Thr Arg Glu Ile Leu Gly Thr
         35                  40                  45

Ala Leu Ala Leu Ala Arg Ala Ser Ala Leu Cys Leu Asn Phe Asn Ser
     50                  55                  60

Met Val Ile Leu Ile Pro Val Cys Arg Asn Leu Leu Ser Phe Leu Arg
 65                  70                  75                  80

Gly Thr Cys Ser Phe Cys Asn His Thr Leu Arg Lys Pro Leu Asp His
```

```
                        85                  90                  95
Asn Leu Thr Phe His Lys Leu Val Ala Tyr Met Ile Cys Ile Phe Thr
                100                 105                 110
Ala Ile His Ile Ile Ala His Leu Phe Asn Phe Glu Arg Tyr Ser Arg
                115                 120                 125
Ser Gln Gln Ala Met Asp Gly Ser Leu Ala Ser Val Leu Ser Ser Leu
            130                 135                 140
Phe His Pro Glu Lys Glu Asp Ser Trp Leu Asn Pro Ile Gln Ser Pro
145                 150                 155                 160
Asn Val Thr Val Met Tyr Ala Ala Phe Thr Ser Ile Ala Gly Leu Thr
                165                 170                 175
Gly Val Val Ala Thr Val Ala Leu Val Leu Met Val Thr Ser Ala Met
                180                 185                 190
Glu Phe Ile Arg Arg Asn Tyr Phe Glu Leu Phe Trp Tyr Thr His His
                195                 200                 205
Leu Phe Ile Ile Tyr Ile Ile Cys Leu Gly Ile His Gly Leu Gly Gly
                210                 215                 220
Ile Val Arg Gly Gln Thr Glu Glu Ser Met Ser Glu Ser His Pro Arg
225                 230                 235                 240
Asn Cys Ser Tyr Ser Phe His Glu Trp Asp Lys Tyr Glu Arg Ser Cys
                245                 250                 255
Arg Ser Pro His Phe Val Gly Gln Pro Pro Glu Ser Trp Lys Trp Ile
                260                 265                 270
Leu Ala Pro Ile Ala Phe Tyr Ile Phe Glu Arg Ile Leu Arg Phe Tyr
                275                 280                 285
Arg Ser Arg Gln Lys Val Ile Thr Lys Val Val Met His Pro Cys
                290                 295                 300
Lys Val Leu Glu Leu Gln Met Arg Lys Arg Gly Phe Thr Met Gly Ile
305                 310                 315                 320
Gly Gln Tyr Ile Phe Val Asn Cys Pro Ser Ile Ser Phe Leu Glu Trp
                325                 330                 335
His Pro Phe Thr Leu Thr Ser Ala Pro Glu Glu Glu Phe Phe Ser Ile
                340                 345                 350
His Ile Arg Ala Ala Gly Asp Trp Thr Glu Asn Leu Ile Arg Thr Phe
                355                 360                 365
Glu Gln Gln His Ser Pro Met Pro Arg Ile Glu Val Asp Gly Pro Phe
                370                 375                 380
Gly Thr Val Ser Glu Asp Val Phe Gln Tyr Glu Val Ala Val Leu Val
385                 390                 395                 400
Gly Ala Gly Ile Gly Val Thr Pro Phe Ala Ser Phe Leu Lys Ser Ile
                405                 410                 415
Trp Tyr Lys Phe Gln Arg Ala His Asn Lys Leu Lys Thr Gln Lys Ile
                420                 425                 430
Tyr Phe Tyr Trp Ile Cys Arg Glu Thr Gly Ala Phe Ala Trp Phe Asn
                435                 440                 445
Asn Leu Leu Asn Ser Leu Glu Gln Glu Met Asp Glu Leu Gly Lys Pro
                450                 455                 460
Asp Phe Leu Asn Tyr Arg Leu Phe Leu Thr Gly Trp Asp Ser Asn Ile
465                 470                 475                 480
Ala Gly His Ala Ala Leu Asn Phe Asp Arg Ala Thr Asp Val Leu Thr
                485                 490                 495
Gly Leu Lys Gln Lys Thr Ser Phe Gly Arg Pro Met Trp Asp Asn Glu
                500                 505                 510
```

```
Phe Ser Arg Ile Ala Thr Ala His Pro Lys Ser Val Val Gly Val Phe
    515                 520                 525

Leu Cys Gly Pro Pro Thr Leu Ala Lys Ser Leu Arg Lys Cys Cys Arg
    530                 535                 540

Arg Tyr Ser Ser Leu Asp Pro Arg Lys Val Gln Phe Tyr Phe Asn Lys
545                 550                 555                 560

Glu Thr Phe

<210> SEQ ID NO 22
<211> LENGTH: 2577
<212> TYPE: DNA
<213> ORGANISM: Rat

<400> SEQUENCE: 22
```

| | | | | | |
|---|---|---|---|---|---|
| ttctgagtag | gtgtgcattt | gagtgtcata | aagacatata | tcttgagcta | gacagaagtt | 60 |
| cctatcctga | aggatcccat | cagagaaacc | agattgctcc | taagaggctc | cagacctcca | 120 |
| tttgacaatg | ggaaactggc | tggttaacca | ctggctctca | gttttgtttc | tggtttcttg | 180 |
| gttgggctg | aacatttttc | tgtttgtgta | cgtcttcctg | aattatgaga | agtctgacaa | 240 |
| gtactattac | acgagagaaa | ttctcggaac | tgccttggcc | ttggccagag | catctgcttt | 300 |
| gtgcctgaat | tttaacagca | tggtgatcct | gattcctgtg | tgtcgaaatc | tgctctcctt | 360 |
| cctgaggggc | acctgctcat | tttgcaacca | cacgctgaga | aagccattgg | atcacaacct | 420 |
| caccttccat | aagctggtgg | catatatgat | ctgcatattc | acagctattc | atatcattgc | 480 |
| acatctattt | aactttgaac | gctacagtag | aagccaacag | gccatggatg | gatctcttgc | 540 |
| ctctgttctc | tccagcctat | tccatcccga | gaaagaagat | tcttggctaa | atcccatcca | 600 |
| gtctccaaac | gtgacagtga | tgtatgcagc | atttaccagt | attgctggcc | ttactggagt | 660 |
| ggtcgccact | gtggctttgg | ttctcatggt | aacttcagct | atggagttta | tccgcaggaa | 720 |
| ttattttgag | ctcttctggt | atacacatca | ccttttcatc | atctatatca | tctgcttagg | 780 |
| gatccatggc | ctggggggga | ttgtccgggg | tcaaacagaa | gagagcatga | gtgaaagtca | 840 |
| tccccgcaac | tgttcatact | cttttccacga | gtgggataag | tatgaaagga | gttgcaggag | 900 |
| tcctcatttt | gtgggggcaac | cccctgagtc | ttggaagtgg | atcctcgcgc | cgattgcttt | 960 |
| ttatatctttt | gaaaggatcc | ttcgctttta | tcgctcccgg | cagaaggtcg | tgattaccaa | 1020 |
| ggttgtcatg | cacccatgta | aagttttgga | attgcagatg | aggaagcggg | gctttactat | 1080 |
| gggaatagga | cagtatatat | tcgtaaattg | cccctcgatt | tccttcctgg | aatggcatcc | 1140 |
| ctttactctg | acctctgctc | cagaggaaga | atttttctcc | attcatattc | gagcagcagg | 1200 |
| ggactggaca | gaaaatctca | taaggacatt | tgaacaacag | cactcaccaa | tgcccaggat | 1260 |
| cgaggtggat | ggtcccttttg | gcacagtcag | tgaggatgtc | ttccagtacg | aagtggctgt | 1320 |
| actggttggg | gcagggattg | gcgtcactcc | ctttgcttcc | ttcttgaaat | ctatctggta | 1380 |
| caaattccag | cgtgcacaca | acaagctgaa | aacacaaaag | atctatttct | actggatttg | 1440 |
| tagagagacg | ggtgccttttg | cctggttcaa | caacttattg | aattccctgg | aacaagagat | 1500 |
| ggacgaatta | ggcaaaccgg | atttcctaaa | ctaccgactc | ttcctcactg | gctgggatag | 1560 |
| caacattgct | ggtcatgcag | cattaaactt | tgcagagcc | actgacgtcc | tgacaggtct | 1620 |
| gaaacagaaa | acctccttttg | ggagaccaat | gtgggacaat | gagttttcta | gaatagctac | 1680 |
| tgcccacccc | aagtctgtgg | tgggggtttt | cttatgcggc | cctccgactt | tggcaaaaag | 1740 |
| cctgcgcaaa | tgctgtcggc | ggtactcaag | tctggatcct | aggaaggttc | aattctactt | 1800 |

```
caacaaagaa acgttctgaa ttggaggaag ccgcacagta gtacttctcc atcttccttt    1860
tcactaacgt gtgggtcagc tactagatag tccgttgtcg cacaaggact tcactcccat    1920
cttaaagttg actcaactcc atcattcttg ggctttggca acatgagagc tgcataactc    1980
acaattgcaa acacatgaa ttattattgg ggggattgta atccttctg ggaaacctgc     2040 ctttagctga atcttgctgg ttgacacttg cacaatttaa cctcaggtgt cttggttgat    2100
acctgataat cttccctccc acctgtccct cacagaagat ttctaagtag ggtgatttta    2160
aaatatttat tgaatccacg acaaaacaat aatcataaat aataaacata aaattaccaa    2220
gattcccact cccatatcat acccactaag aacatcgtta tacatgagct tatcatccag    2280
tgtgaccaac aatttatact ttactgtgcc aaaataatct tcatctttgc ttattgaaca    2340
attttgctga ctttccctag taatatctta agtatattaa ctggaatcaa atttgtatta    2400
tagttagaag ccaactatat tgccagtttg tattgtttga aataactgga aaggcctgac    2460
ctacatcgtg gggtaattta acagaagctc tttccatttt ttgttgttgt tgttaaagag    2520
ttttgtttat gaatgtgtta taaaagaaa ataaaaagtt ataattttga cggaaaa       2577
```

<210> SEQ ID NO 23
<211> LENGTH: 332
<212> TYPE: PRT
<213> ORGANISM: Homo sapiens

<400> SEQUENCE: 23

```
Glu Ser Met Asn Glu Ser His Pro Arg Lys Cys Ala Glu Ser Phe Glu
 1               5                  10                  15

Met Trp Asp Arg Asp Ser His Cys Arg Arg Pro Lys Phe Glu Gly
            20                  25                  30

His Pro Pro Glu Ser Trp Lys Trp Ile Leu Ala Pro Val Ile Leu Tyr
        35                  40                  45

Ile Cys Glu Arg Ile Leu Arg Phe Tyr Arg Ser Gln Gln Lys Val Val
    50                  55                  60

Ile Thr Lys Val Val Met His Pro Ser Lys Val Leu Glu Leu Gln Met
65                  70                  75                  80

Asn Lys Arg Gly Phe Ser Met Glu Val Gly Gln Tyr Ile Phe Val Asn
                85                  90                  95

Cys Pro Ser Ile Ser Leu Leu Glu Trp His Pro Phe Thr Leu Thr Ser
            100                 105                 110

Ala Pro Glu Glu Asp Phe Phe Ser Ile His Ile Arg Ala Ala Gly Asp
        115                 120                 125

Trp Thr Glu Asn Leu Ile Arg Ala Phe Glu Gln Gln Tyr Ser Pro Ile
    130                 135                 140

Pro Arg Ile Glu Val Asp Gly Pro Phe Gly Thr Ala Ser Glu Asp Val
145                 150                 155                 160

Phe Gln Tyr Glu Val Ala Val Leu Val Gly Ala Gly Ile Gly Val Thr
                165                 170                 175

Pro Phe Ala Ser Ile Leu Lys Ser Ile Trp Tyr Lys Phe Gln Cys Ala
            180                 185                 190

Asp His Asn Leu Lys Thr Lys Lys Ile Tyr Phe Tyr Trp Ile Cys Arg
        195                 200                 205

Glu Thr Gly Ala Phe Ser Trp Phe Asn Asn Leu Leu Thr Ser Leu Glu
    210                 215                 220

Gln Glu Met Glu Glu Leu Gly Lys Val Gly Phe Leu Asn Tyr Arg Leu
225                 230                 235                 240
```

```
Phe Leu Thr Gly Trp Asp Ser Asn Ile Val Gly His Ala Ala Leu Asn
                245                 250                 255

Phe Asp Lys Ala Thr Asp Ile Val Thr Gly Leu Lys Gln Lys Thr Ser
            260                 265                 270

Phe Gly Arg Pro Met Trp Asp Asn Glu Phe Ser Thr Ile Ala Thr Ser
        275                 280                 285

His Pro Lys Ser Val Val Gly Val Phe Leu Cys Gly Pro Arg Thr Leu
    290                 295                 300

Ala Lys Ser Leu Arg Lys Cys Cys His Arg Tyr Ser Ser Leu Asp Pro
305                 310                 315                 320

Arg Lys Val Gln Phe Tyr Phe Asn Lys Glu Asn Phe
                325                 330

<210> SEQ ID NO 24
<211> LENGTH: 14
<212> TYPE: PRT
<213> ORGANISM: Homo sapiens

<400> SEQUENCE: 24

Cys Ala Glu Ser Phe Glu Met Trp Asp Asp Arg Asp Ser His
  1               5                  10

<210> SEQ ID NO 25
<211> LENGTH: 14
<212> TYPE: PRT
<213> ORGANISM: Homo sapiens

<400> SEQUENCE: 25

Lys Ser Leu Arg Lys Cys Cys His Arg Tyr Ser Ser Leu Asp
  1               5                  10

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 26
gaagtggtgg gaggcgaaga cata                                          24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 27
cctgtcatac ctgggacggt ctgg                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 28
gagcacagtg agatgcctgt tcag                                          24

<210> SEQ ID NO 29
```

```
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 29
ggaaggcagc agagagcaat gatg                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 30
acatctgcga gcggcacttc caga                                          24

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 31
agctcgtcaa caggcaggac cgagc                                         25

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 32
gcagtgcatc cacatcttca gcac                                          24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 33
gagagctctg gagacacttg agttc                                         25

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 34
catgttctct ctggctgaca ag                                            22

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 35
```
cacaatagcg agctccgctt cacgc         25

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 36
gcaggacatc aaccctgcac tctc         24

<210> SEQ ID NO 37
<211> LENGTH: 570
<212> TYPE: PRT
<213> ORGANISM: Bovine

<400> SEQUENCE: 37

```
Met Gly Asn Trp Val Val Asn Glu Gly Ile Ser Ile Phe Val Ile Leu
 1               5                  10                  15

Val Trp Leu Gly Met Asn Val Phe Leu Phe Val Trp Tyr Tyr Arg Val
            20                  25                  30

Tyr Asp Ile Pro Asp Lys Phe Phe Tyr Thr Arg Lys Leu Leu Gly Ser
        35                  40                  45

Ala Leu Ala Leu Ala Arg Ala Pro Ala Ala Cys Leu Asn Phe Asn Cys
    50                  55                  60

Met Leu Ile Leu Leu Pro Val Cys Arg Asn Leu Leu Ser Phe Leu Arg
 65                  70                  75                  80

Gly Ser Ser Ala Cys Cys Ser Thr Arg Ile Arg Arg Gln Leu Asp Arg
                85                  90                  95

Asn Leu Thr Phe His Lys Met Val Ala Trp Met Ile Ala Leu His Thr
            100                 105                 110

Ala Ile His Thr Ile Ala His Leu Phe Asn Val Glu Trp Cys Val Asn
        115                 120                 125

Ala Arg Val Asn Asn Ser Asp Pro Tyr Ser Ile Ala Leu Ser Asp Ile
    130                 135                 140

Gly Asp Lys Pro Asn Glu Thr Tyr Leu Asn Phe Val Arg Gln Arg Ile
145                 150                 155                 160

Lys Asn Pro Glu Gly Gly Leu Tyr Val Ala Val Thr Arg Leu Ala Gly
                165                 170                 175

Ile Thr Gly Val Val Ile Thr Leu Cys Leu Ile Leu Ile Ile Thr Ser
            180                 185                 190

Ser Thr Lys Thr Ile Arg Arg Ser Tyr Phe Glu Val Phe Trp Tyr Thr
        195                 200                 205

His His Leu Phe Val Ile Phe Phe Ile Gly Leu Ala Ile His Gly Ala
    210                 215                 220

Gln Arg Ile Val Arg Gly Gln Thr Ala Glu Ser Leu Leu Lys His Gln
225                 230                 235                 240

Pro Arg Asn Cys Tyr Gln Asn Ile Ser Gln Trp Gly Lys Ile Glu Asn
                245                 250                 255

Cys Pro Ile Pro Glu Phe Ser Gly Asn Pro Pro Met Thr Trp Lys Trp
            260                 265                 270

Ile Val Gly Pro Met Phe Leu Tyr Leu Cys Glu Arg Leu Val Arg Phe
        275                 280                 285

Trp Arg Ser Gln Gln Lys Val Val Ile Thr Lys Val Val Thr His Pro
    290                 295                 300
```

```
Phe Lys Thr Ile Glu Leu Gln Met Lys Lys Gly Phe Lys Met Glu
305                 310                 315                 320

Val Gly Gln Tyr Ile Phe Val Lys Cys Pro Val Val Ser Lys Leu Glu
                325                 330                 335

Trp His Pro Phe Thr Leu Thr Ser Ala Pro Glu Asp Phe Phe Ser
                340                 345                 350

Ile His Ile Arg Ile Val Gly Asp Trp Thr Glu Gly Leu Phe Lys Ala
                355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Lys Ala Pro
                420                 425                 430

Asn Leu Arg Leu Lys Lys Ile Tyr Phe Tyr Trp Leu Cys Arg Asp Thr
                435                 440                 445

His Ala Phe Glu Trp Phe Ala Asp Leu Leu Gln Leu Leu Glu Thr Gln
    450                 455                 460

Met Gln Glu Lys Asn Asn Thr Asp Phe Leu Ser Tyr Asn Ile Cys Leu
465                 470                 475                 480

Thr Gly Trp Asp Glu Ser Gln Ala Ser His Phe Ala Met His His Asp
                485                 490                 495

Glu Glu Lys Asp Val Ile Thr Gly Leu Lys Gln Lys Thr Leu Tyr Gly
                500                 505                 510

Arg Pro Asn Trp Asp Asn Glu Phe Lys Thr Ile Gly Ser Gln His Pro
                515                 520                 525

Asn Thr Arg Ile Gly Val Phe Leu Cys Gly Pro Glu Ala Leu Ala Asp
                530                 535                 540

Thr Leu Asn Lys Gln Cys Ile Ser Asn Ser Asp Ser Gly Pro Arg Gly
545                 550                 555                 560

Val His Phe Ile Phe Asn Lys Glu Asn Phe
                565                 570

<210> SEQ ID NO 38
<211> LENGTH: 570
<212> TYPE: PRT
<213> ORGANISM: murine

<400> SEQUENCE: 38

Met Gly Asn Trp Ala Val Asn Glu Gly Leu Ser Ile Phe Val Ile Leu
1               5                   10                  15

Val Trp Leu Gly Leu Asn Val Phe Leu Phe Ile Asn Tyr Tyr Lys Val
                20                  25                  30

Tyr Asp Asp Gly Pro Lys Tyr Asn Tyr Thr Arg Lys Leu Leu Gly Ser
            35                  40                  45

Ala Leu Ala Leu Ala Arg Ala Pro Ala Ala Cys Leu Asn Phe Asn Cys
        50                  55                  60

Met Leu Ile Leu Leu Pro Val Cys Arg Asn Leu Leu Ser Phe Leu Arg
65                  70                  75                  80

Gly Ser Ser Ala Cys Cys Ser Thr Arg Ile Arg Arg Gln Leu Asp Arg
                85                  90                  95
```

-continued

```
Asn Leu Thr Phe His Lys Met Val Ala Trp Met Ile Ala Leu His Thr
                100                 105                 110
Ala Ile His Thr Ile Ala His Leu Phe Asn Val Glu Trp Cys Val Asn
            115                 120                 125
Ala Arg Val Gly Ile Ser Asp Arg Tyr Ser Ile Ala Leu Ser Asp Ile
        130                 135                 140
Gly Asp Asn Glu Asn Glu Glu Tyr Leu Asn Phe Ala Arg Glu Lys Ile
145                 150                 155                 160
Lys Asn Pro Glu Gly Gly Leu Tyr Val Ala Val Thr Arg Leu Ala Gly
                165                 170                 175
Ile Thr Gly Ile Val Ile Thr Leu Cys Leu Ile Leu Ile Ile Thr Ser
            180                 185                 190
Ser Thr Lys Thr Ile Arg Arg Ser Tyr Phe Glu Val Phe Trp Tyr Thr
        195                 200                 205
His His Leu Phe Val Ile Phe Phe Ile Gly Leu Ala Ile His Gly Ala
    210                 215                 220
Glu Arg Ile Val Arg Gly Gln Thr Ala Glu Ser Leu Glu Glu His Asn
225                 230                 235                 240
Leu Asp Ile Cys Ala Asp Lys Ile Glu Glu Trp Gly Lys Ile Lys Glu
                245                 250                 255
Cys Pro Val Pro Lys Phe Ala Gly Asn Pro Pro Met Thr Trp Lys Trp
            260                 265                 270
Ile Val Gly Pro Met Phe Leu Tyr Leu Cys Glu Arg Leu Val Arg Phe
        275                 280                 285
Trp Arg Ser Gln Gln Lys Val Val Ile Thr Lys Val Val Thr His Pro
    290                 295                 300
Phe Lys Thr Ile Glu Leu Gln Met Lys Lys Gly Phe Lys Met Glu
305                 310                 315                 320
Val Gly Gln Tyr Ile Phe Val Lys Cys Pro Lys Val Ser Lys Leu Glu
                325                 330                 335
Trp His Pro Phe Thr Leu Thr Ser Ala Pro Glu Glu Asp Phe Phe Ser
            340                 345                 350
Ile His Ile Arg Ile Val Gly Asp Trp Thr Glu Gly Leu Phe Asn Ala
        355                 360                 365
Cys Gly Cys Asp Lys Gln Glu Phe Gln Asp Ala Trp Lys Leu Pro Lys
    370                 375                 380
Ile Ala Val Asp Gly Pro Phe Gly Thr Ala Ser Glu Asp Val Phe Ser
385                 390                 395                 400
Tyr Glu Val Val Met Leu Val Gly Ala Gly Ile Gly Val Thr Pro Phe
                405                 410                 415
Ala Ser Ile Leu Lys Ser Val Trp Tyr Lys Tyr Cys Asp Asn Ala Thr
            420                 425                 430
Ser Leu Lys Leu Lys Lys Ile Tyr Phe Tyr Trp Leu Cys Arg Asp Thr
        435                 440                 445
His Ala Phe Glu Trp Phe Ala Asp Leu Leu Gln Leu Leu Glu Thr Gln
    450                 455                 460
Met Gln Glu Arg Asn Asn Ala Asn Phe Leu Ser Tyr Asn Ile Tyr Leu
465                 470                 475                 480
Thr Gly Trp Asp Glu Ser Gln Ala Asn His Phe Ala Val His His Asp
                485                 490                 495
Glu Glu Lys Asp Val Ile Thr Gly Leu Lys Gln Lys Thr Leu Tyr Gly
            500                 505                 510
Arg Pro Asn Trp Asp Asn Glu Phe Lys Thr Ile Ala Ser Glu His Pro
```

```
            515                 520                 525
Asn Thr Thr Ile Gly Val Phe Leu Cys Gly Pro Glu Ala Leu Ala Glu
        530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570

<210> SEQ ID NO 39
<211> LENGTH: 944
<212> TYPE: PRT
<213> ORGANISM: Arabidopsis sp.

<400> SEQUENCE: 39

Met Lys Pro Phe Ser Lys Asn Asp Arg Arg Trp Ser Phe Asp Ser
 1               5                  10                  15

Val Ser Ala Gly Lys Thr Ala Val Gly Ser Ala Ser Thr Ser Pro Gly
                20                  25                  30

Thr Glu Tyr Ser Ile Asn Gly Asp Gln Glu Phe Val Glu Val Thr Ile
            35                  40                  45

Asp Leu Gln Asp Asp Thr Ile Val Leu Arg Ser Val Glu Pro Ala
     50                  55                  60

Thr Ala Ile Asn Val Ile Gly Asp Ile Ser Asp Asn Thr Gly Ile
 65                  70                  75                  80

Met Thr Pro Val Ser Ile Ser Arg Ser Pro Thr Met Lys Arg Thr Ser
                85                  90                  95

Ser Asn Arg Phe Arg Gln Phe Ser Gln Glu Leu Lys Ala Glu Ala Val
            100                 105                 110

Ala Lys Ala Lys Gln Leu Ser Gln Glu Leu Lys Arg Phe Ser Trp Ser
        115                 120                 125

Arg Ser Phe Ser Gly Asn Leu Thr Thr Thr Ser Thr Ala Ala Asn Gln
130                 135                 140

Ser Gly Gly Ala Gly Gly Gly Leu Val Asn Ser Ala Leu Glu Ala Arg
145                 150                 155                 160

Ala Leu Arg Lys Gln Arg Ala Gln Leu Asp Arg Thr Arg Ser Ser Ala
                165                 170                 175

Gln Arg Ala Leu Arg Gly Leu Arg Phe Ile Ser Asn Lys Gln Lys Asn
            180                 185                 190

Val Asp Gly Trp Asn Asp Val Gln Ser Asn Phe Glu Lys Phe Glu Lys
        195                 200                 205

Asn Gly Tyr Ile Tyr Arg Ser Asp Phe Ala Gln Cys Ile Gly Met Lys
    210                 215                 220

Asp Ser Lys Glu Phe Ala Leu Glu Leu Phe Asp Ala Leu Ser Arg Arg
225                 230                 235                 240

Arg Arg Leu Lys Val Glu Lys Ile Asn His Asp Glu Leu Tyr Glu Tyr
                245                 250                 255

Trp Ser Gln Ile Asn Asp Glu Ser Phe Asp Ser Arg Leu Gln Ile Phe
            260                 265                 270

Phe Asp Ile Val Asp Lys Asn Glu Asp Gly Arg Ile Thr Glu Glu Glu
        275                 280                 285

Val Lys Glu Ile Ile Met Leu Ser Ala Ser Ala Asn Lys Leu Ser Arg
    290                 295                 300

Leu Lys Glu Gln Ala Glu Glu Tyr Ala Ala Leu Ile Met Glu Glu Leu
305                 310                 315                 320
```

-continued

```
Asp Pro Glu Arg Leu Gly Tyr Ile Glu Leu Trp Gln Leu Glu Thr Leu
            325                 330                 335
Leu Leu Gln Lys Asp Thr Tyr Leu Asn Tyr Ser Gln Ala Leu Ser Tyr
                340                 345                 350
Thr Ser Gln Ala Leu Ser Gln Asn Leu Gln Gly Leu Arg Gly Lys Ser
            355                 360                 365
Arg Ile His Arg Met Ser Ser Asp Phe Val Tyr Ile Met Gln Glu Asn
        370                 375                 380
Trp Lys Arg Ile Trp Val Leu Ser Leu Trp Ile Met Ile Met Ile Gly
385                 390                 395                 400
Leu Phe Leu Trp Lys Phe Phe Gln Tyr Lys Gln Lys Asp Ala Phe His
                405                 410                 415
Val Met Gly Tyr Cys Leu Leu Thr Ala Lys Gly Ala Ala Glu Thr Leu
            420                 425                 430
Lys Phe Asn Met Ala Leu Ile Leu Phe Pro Val Cys Arg Asn Thr Ile
        435                 440                 445
Thr Trp Leu Arg Ser Thr Arg Leu Ser Tyr Phe Val Pro Phe Asp Asp
    450                 455                 460
Asn Ile Asn Phe His Lys Thr Ile Ala Gly Ala Ile Val Val Ala Val
465                 470                 475                 480
Ile Leu His Ile Gly Asp His Leu Ala Cys Asp Phe Pro Arg Ile Val
                485                 490                 495
Arg Ala Thr Glu Tyr Asp Tyr Asn Arg Tyr Leu Phe His Tyr Phe Gln
            500                 505                 510
Thr Lys Gln Pro Thr Tyr Phe Asp Leu Val Lys Gly Pro Glu Gly Ile
        515                 520                 525
Thr Gly Ile Leu Met Val Ile Leu Met Ile Ile Ser Phe Thr Leu Ala
    530                 535                 540
Thr Arg Trp Phe Arg Arg Asn Leu Val Lys Leu Pro Lys Pro Phe Asp
545                 550                 555                 560
Arg Leu Thr Gly Phe Asn Ala Phe Trp Tyr Ser His His Leu Phe Val
                565                 570                 575
Ile Val Tyr Ile Leu Leu Ile Leu His Gly Ile Phe Leu Tyr Phe Ala
            580                 585                 590
Lys Pro Trp Tyr Val Arg Thr Thr Trp Met Tyr Leu Ala Val Pro Val
        595                 600                 605
Leu Leu Tyr Gly Gly Glu Arg Thr Leu Arg Tyr Phe Arg Ser Gly Ser
    610                 615                 620
Tyr Ser Val Arg Leu Leu Lys Val Ala Ile Tyr Pro Gly Asn Val Leu
625                 630                 635                 640
Thr Leu Gln Met Ser Lys Pro Thr Gln Phe Arg Tyr Lys Ser Gly Gln
                645                 650                 655
Tyr Met Phe Val Gln Cys Pro Ala Val Ser Pro Phe Glu Trp His Pro
            660                 665                 670
Phe Ser Ile Thr Ser Ala Pro Glu Asp Asp Tyr Ile Ser Ile His Ile
        675                 680                 685
Arg Gln Leu Gly Asp Trp Thr Gln Glu Leu Lys Arg Val Phe Ser Glu
    690                 695                 700
Val Cys Glu Pro Pro Val Gly Lys Ser Gly Leu Leu Arg Ala Asp
705                 710                 715                 720
Glu Thr Thr Lys Lys Ser Leu Pro Lys Leu Leu Ile Asp Gly Pro Tyr
                725                 730                 735
Gly Ala Pro Ala Gln Asp Tyr Arg Lys Tyr Asp Val Leu Leu Leu Val
```

-continued

```
                740                 745                 750
Gly Leu Gly Ile Gly Ala Thr Pro Phe Ile Ser Ile Leu Lys Asp Leu
            755                 760                 765
Leu Asn Asn Ile Val Lys Met Glu Glu His Ala Asp Ser Ile Ser Asp
        770                 775                 780
Phe Ser Arg Ser Ser Glu Tyr Ser Thr Gly Ser Asn Gly Asp Thr Pro
785                 790                 795                 800
Arg Arg Lys Arg Ile Leu Lys Thr Thr Asn Ala Tyr Phe Tyr Trp Val
                805                 810                 815
Thr Arg Glu Gln Gly Ser Phe Asp Trp Phe Lys Gly Val Met Asn Glu
            820                 825                 830
Val Ala Glu Leu Asp Gln Arg Gly Val Ile Glu Met His Asn Tyr Leu
        835                 840                 845
Thr Ser Val Tyr Glu Glu Gly Asp Ala Arg Ser Ala Leu Ile Thr Met
    850                 855                 860
Val Gln Ala Leu Asn His Ala Lys Asn Gly Val Asp Ile Val Ser Gly
865                 870                 875                 880
Thr Arg Val Arg Thr His Phe Ala Arg Pro Asn Trp Lys Lys Val Leu
                885                 890                 895
Thr Lys Leu Ser Ser Lys His Cys Asn Ala Arg Ile Gly Val Phe Tyr
            900                 905                 910
Cys Gly Val Pro Val Leu Gly Lys Glu Leu Ser Lys Leu Cys Asn Thr
        915                 920                 925
Phe Asn Gln Lys Gly Ser Thr Lys Phe Glu Phe His Lys Glu His Phe
    930                 935                 940

<210> SEQ ID NO 40
<211> LENGTH: 590
<212> TYPE: PRT
<213> ORGANISM: Rice

<400> SEQUENCE: 40

Asn Leu Ala Gly Leu Arg Lys Lys Ser Ser Ile Arg Lys Ile Ser Thr
1               5                   10                  15
Ser Leu Ser Tyr Tyr Phe Glu Asp Asn Trp Lys Arg Leu Trp Val Leu
            20                  25                  30
Ala Leu Trp Ile Gly Ile Met Ala Gly Leu Phe Thr Trp Lys Phe Met
        35                  40                  45
Gln Tyr Arg Asn Arg Tyr Val Phe Asp Val Met Gly Tyr Cys Val Thr
    50                  55                  60
Thr Ala Lys Gly Ala Ala Glu Thr Leu Lys Leu Asn Met Ala Ile Ile
65                  70                  75                  80
Leu Leu Pro Val Cys Arg Asn Thr Ile Thr Trp Leu Arg Ser Thr Arg
                85                  90                  95
Ala Ala Arg Ala Leu Pro Phe Asp Asp Asn Ile Asn Phe His Lys Thr
            100                 105                 110
Ile Ala Ala Ile Val Val Gly Ile Ile Leu His Ala Gly Asn His
        115                 120                 125
Leu Val Cys Asp Phe Pro Arg Leu Ile Lys Ser Ser Asp Glu Lys Tyr
    130                 135                 140
Ala Pro Leu Gly Gln Tyr Phe Gly Glu Ile Lys Pro Thr Tyr Phe Thr
145                 150                 155                 160
Leu Val Lys Gly Val Glu Gly Ile Thr Gly Val Ile Met Val Val Cys
                165                 170                 175
```

```
Met Ile Ile Ala Phe Thr Leu Ala Thr Arg Trp Phe Arg Arg Ser Leu
                180                 185                 190

Val Lys Leu Pro Arg Pro Phe Asp Lys Leu Thr Gly Phe Asn Ala Phe
            195                 200                 205

Trp Tyr Ser His His Leu Phe Ile Ile Val Tyr Ile Ala Leu Ile Val
        210                 215                 220

His Gly Glu Cys Leu Tyr Leu Ile His Val Trp Tyr Arg Arg Thr Thr
225                 230                 235                 240

Trp Met Tyr Leu Ser Val Pro Val Cys Leu Tyr Val Gly Glu Arg Ile
                245                 250                 255

Leu Arg Phe Phe Arg Ser Gly Ser Tyr Ser Val Arg Leu Leu Lys Val
            260                 265                 270

Ala Ile Tyr Pro Gly Asn Val Leu Thr Leu Gln Met Ser Lys Pro Pro
        275                 280                 285

Thr Phe Arg Tyr Lys Ser Gly Gln Tyr Met Phe Val Gln Cys Pro Ala
    290                 295                 300

Val Ser Pro Phe Glu Trp His Pro Phe Ser Ile Thr Ser Ala Pro Gly
305                 310                 315                 320

Asp Asp Tyr Leu Ser Ile His Val Arg Gln Leu Gly Asp Trp Thr Arg
                325                 330                 335

Glu Leu Lys Arg Val Phe Ala Ala Ala Cys Glu Pro Pro Ala Gly Gly
            340                 345                 350

Lys Ser Gly Leu Leu Arg Ala Asp Glu Thr Thr Lys Lys Ile Leu Pro
        355                 360                 365

Lys Leu Leu Ile Asp Gly Pro Tyr Gly Ser Pro Ala Gln Asp Tyr Ser
    370                 375                 380

Lys Tyr Asp Val Leu Leu Leu Val Gly Leu Gly Ile Gly Ala Thr Pro
385                 390                 395                 400

Phe Ile Ser Ile Leu Lys Asp Leu Leu Asn Asn Ile Ile Lys Met Glu
                405                 410                 415

Glu Glu Glu Asp Ala Ser Thr Asp Leu Tyr Pro Pro Met Gly Arg Asn
            420                 425                 430

Asn Pro His Val Asp Leu Gly Thr Leu Met Thr Ile Thr Ser Arg Pro
        435                 440                 445

Lys Lys Ile Leu Lys Thr Thr Asn Ala Tyr Phe Tyr Trp Val Thr Arg
    450                 455                 460

Glu Gln Gly Ser Phe Asp Trp Phe Lys Gly Val Met Asn Glu Ile Ala
465                 470                 475                 480

Asp Leu Asp Gln Arg Asn Ile Ile Glu Met His Asn Tyr Leu Thr Ser
                485                 490                 495

Val Tyr Glu Glu Gly Asp Ala Arg Ser Ala Leu Ile Thr Met Leu Gln
            500                 505                 510

Ala Leu Asn His Ala Lys Asn Gly Val Asp Ile Val Ser Gly Thr Lys
        515                 520                 525

Val Arg Thr His Phe Ala Arg Pro Asn Trp Arg Lys Val Leu Ser Lys
    530                 535                 540

Ile Ser Ser Lys His Pro Tyr Ala Lys Ile Gly Val Phe Tyr Cys Gly
545                 550                 555                 560

Ala Pro Val Leu Ala Gln Glu Leu Ser Lys Leu Cys His Glu Phe Asn
                565                 570                 575

Gly Lys Cys Thr Thr Lys Phe Asp Phe His Lys Glu His Phe
            580                 585                 590
```

<210> SEQ ID NO 41
<211> LENGTH: 2619
<212> TYPE: DNA
<213> ORGANISM: Rat

<400> SEQUENCE: 41

| | | | | | | |
|---|---|---|---|---|---|---|
| gtgctgtcag | agctttacag | agcctctggg | catgcgcatg | gctacccatt | tcattgattt | 60 |
| acagaagtca | tgctaaaatc | tctttcatgc | atgtcttcct | ttttcagtct | ctcctttccc | 120 |
| aaagcttttc | agtttgccct | tgcttgtac | caactgctat | ccctcctcaa | aggctgctgc | 180 |
| aaaaggtatg | cctttttctt | ggaggctttc | agcaaatact | acctgggaac | ctgcttcagc | 240 |
| tcttggaata | tttaagtgaa | gagaacattt | catagcattt | gtatctttct | ttgaaggagc | 300 |
| caccagacag | actgccttgg | ccttggccag | agcatctgct | ttgtgcctga | attttaacag | 360 |
| catggtgatc | ctgattcctg | tgtgtcgaaa | tctgctctcc | ttcctgaggg | gcacctgctc | 420 |
| attttgcaac | cacacgctga | gaaagccatt | ggatcacaac | ctcaccttcc | ataagctggt | 480 |
| ggcatatatg | atctgcatat | tcacagctat | tcatatcatt | gcacatctat | ttaactttga | 540 |
| acgctacagt | agaagccaac | aggccatgga | tggatctctt | gcctctgttc | tctccagcct | 600 |
| attccatccc | gagaaagaag | attcttggct | aaatcccatc | cagtctccaa | acgtgacagt | 660 |
| gatgtatgca | gcatttacca | gtattgctgg | ccttactgga | gtggtcgcca | ctgtggcttt | 720 |
| ggttctcatg | gtaacttcag | ctatggagtt | tatccgcagg | aattattttg | agctcttctg | 780 |
| gtatacacat | caccttttca | tcatctatat | catctgctta | gggatccatg | cctgggggg | 840 |
| gattgtccgg | ggtcaaacag | aagagagcat | gagtgaaagt | catccccgca | actgttcata | 900 |
| ctctttccac | gagtgggata | gtatgaaag | gagttcagg | agtcctcatt | ttgtggggca | 960 |
| acccctgag | tcttggaagt | ggatcctcgc | gccgattgct | ttttatatct | ttgaaaggat | 1020 |
| ccttcgcttt | tatcgctccc | ggcagaaggt | cgtgattacc | aaggttgtca | tgcacccatg | 1080 |
| taaagttttg | gaattgcaga | tgaggaagcg | gggcttact | atgggaatag | gacagtatat | 1140 |
| attcgtaaat | tgcccctcga | tttccttcct | ggaatggcat | ccctttactc | tgacctctgc | 1200 |
| tccagaggaa | gaattttct | ccattcatat | tcgagcagca | ggggactgga | cagaaaatct | 1260 |
| cataaggaca | tttgaacaac | agcactcacc | aatgcccagg | atcgaggtgg | atggtccctt | 1320 |
| tggcacagtc | agtgaggatg | tcttccagta | cgaagtggct | gtactggttg | gggcagggat | 1380 |
| tggcgtcact | cccttttgctt | ccttcttgaa | atctatctgg | tacaaattcc | agcgtgcaca | 1440 |
| caacaagctg | aaaacacaaa | agatctattt | ctactggatt | tgtagagaga | cgggtgcctt | 1500 |
| tgcctggttc | aacaacttat | tgaattccct | ggaacaagag | atggacgaat | taggcaaacc | 1560 |
| ggatttccta | aactaccgac | tcttcctcac | tggctgggat | agcaacattg | ctggtcatgc | 1620 |
| agcattaaac | tttgacagag | ccactgacgt | cctgacaggt | ctgaaacaga | aaacctcctt | 1680 |
| tgggagacca | atgtgggaca | atgagttttc | tagaatagc | actgcccacc | ccaagtctgt | 1740 |
| ggtgggggtt | ttcttatgcg | gccctccgac | tttggcaaaa | agcctgcgca | aatgctgtcg | 1800 |
| gcggtactca | agtctggatc | ctaggaaggt | tcaattctac | ttcaacaaag | aaacgttctg | 1860 |
| aattggagga | agccgcacag | tagtacttct | ccatcttcct | tttcactaac | gtgtgggtca | 1920 |
| gctactagat | agtccgttgt | cgcacaagga | cttcactccc | atcttaaagt | tgactcaact | 1980 |
| ccatcattct | tgggctttgg | caacatgaga | gctgcataac | tcacaattgc | aaaacacatg | 2040 |
| aattattatt | gggggattg | taaatccttc | tgggaaacct | gcctttagct | gaatcttgct | 2100 |
| ggttgacact | tgcacaattt | aacctcaggt | gtcttggttg | atacctgata | atcttccctc | 2160 |

-continued

```
ccacctgtcc ctcacagaag atttctaagt agggtgattt taaaatattt attgaatcca    2220
cgacaaaaca ataatcataa ataataaaca taaaattacc aagattccca ctcccatatc    2280
atacccacta agaacatcgt tatacatgag cttatcatcc agtgtgacca acaatttata    2340
ctttactgtg ccaaaataat cttcatcttt gcttattgaa caattttgct gactttccct    2400
agtaatatct taagtatatt aactggaatc aaatttgtat tatagttaga agccaactat    2460
attgccagtt tgtattgttt gaaataactg gaaaggcctg acctacatcg tggggtaatt    2520
taacagaagc tctttccatt ttttgttgtt gttgttaaag agttttgttt atgaatgtgt    2580 tataaaaga aaataaaaag ttataatttt gacggaaaa                            2619
```

<210> SEQ ID NO 42
<211> LENGTH: 499
<212> TYPE: PRT
<213> ORGANISM: Rat

<400> SEQUENCE: 42

```
Met Val Ile Leu Ile Pro Val Cys Arg Asn Leu Leu Ser Phe Leu Arg
  1               5                  10                  15

Gly Thr Cys Ser Phe Cys Asn His Thr Leu Arg Lys Pro Leu Asp His
             20                  25                  30

Asn Leu Thr Phe His Lys Leu Val Ala Tyr Met Ile Cys Ile Phe Thr
         35                  40                  45

Ala Ile His Ile Ile Ala His Leu Phe Asn Phe Glu Arg Tyr Ser Arg
     50                  55                  60

Ser Gln Gln Ala Met Asp Gly Ser Leu Ala Ser Val Leu Ser Ser Leu
 65                  70                  75                  80

Phe His Pro Glu Lys Glu Asp Ser Trp Leu Asn Pro Ile Gln Ser Pro
                 85                  90                  95

Asn Val Thr Val Met Tyr Ala Ala Phe Thr Ser Ile Ala Gly Leu Thr
            100                 105                 110

Gly Val Val Ala Thr Val Ala Leu Val Leu Met Val Thr Ser Ala Met
        115                 120                 125

Glu Phe Ile Arg Arg Asn Tyr Phe Glu Leu Phe Trp Tyr Thr His His
    130                 135                 140

Leu Phe Ile Ile Tyr Ile Ile Cys Leu Gly Ile His Gly Leu Gly Gly
145                 150                 155                 160

Ile Val Arg Gly Gln Thr Glu Glu Ser Met Ser Glu Ser His Pro Arg
                165                 170                 175

Asn Cys Ser Tyr Ser Phe His Glu Trp Asp Lys Tyr Glu Arg Ser Cys
            180                 185                 190

Arg Ser Pro His Phe Val Gly Gln Pro Pro Glu Ser Trp Lys Trp Ile
        195                 200                 205

Leu Ala Pro Ile Ala Phe Tyr Ile Phe Glu Arg Ile Leu Arg Phe Tyr
    210                 215                 220

Arg Ser Arg Gln Lys Val Val Ile Thr Lys Val Val Met His Pro Cys
225                 230                 235                 240

Lys Val Leu Glu Leu Gln Met Arg Lys Arg Gly Phe Thr Met Gly Ile
                245                 250                 255

Gly Gln Tyr Ile Phe Val Asn Cys Pro Ser Ile Ser Phe Leu Glu Trp
            260                 265                 270

His Pro Phe Thr Leu Thr Ser Ala Pro Glu Glu Glu Phe Phe Ser Ile
        275                 280                 285

His Ile Arg Ala Ala Gly Asp Trp Thr Glu Asn Leu Ile Arg Thr Phe
```

-continued

```
                290                 295                 300
Glu Gln Gln His Ser Pro Met Pro Arg Ile Glu Val Asp Gly Pro Phe
305                 310                 315                 320

Gly Thr Val Ser Glu Asp Val Phe Gln Tyr Glu Val Ala Val Leu Val
                325                 330                 335

Gly Ala Gly Ile Gly Val Thr Pro Phe Ala Ser Phe Leu Lys Ser Ile
                340                 345                 350

Trp Tyr Lys Phe Gln Arg Ala His Asn Lys Leu Lys Thr Gln Lys Ile
                355                 360                 365

Tyr Phe Tyr Trp Ile Cys Arg Glu Thr Gly Ala Phe Ala Trp Phe Asn
                370                 375                 380

Asn Leu Leu Asn Ser Leu Glu Gln Glu Met Asp Glu Leu Gly Lys Pro
385                 390                 395                 400

Asp Phe Leu Asn Tyr Arg Leu Phe Leu Thr Gly Trp Asp Ser Asn Ile
                405                 410                 415

Ala Gly His Ala Ala Leu Asn Phe Asp Arg Ala Thr Asp Val Leu Thr
                420                 425                 430

Gly Leu Lys Gln Lys Thr Ser Phe Gly Arg Pro Met Trp Asp Asn Glu
                435                 440                 445

Phe Ser Arg Ile Ala Thr Ala His Pro Lys Ser Val Val Gly Val Phe
450                 455                 460

Leu Cys Gly Pro Pro Thr Leu Ala Lys Ser Leu Arg Lys Cys Cys Arg
465                 470                 475                 480

Arg Tyr Ser Ser Leu Asp Pro Arg Lys Val Gln Phe Tyr Phe Asn Lys
                485                 490                 495

Glu Thr Phe

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 43
ttctgagtag gtgtgcattt gagtgtcata aagac                              35

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence:  synthetic
      primer

<400> SEQUENCE: 44
ttttccgtca aaattataac tttttatttt cttttttataa cacat                  45

<210> SEQ ID NO 45
<211> LENGTH: 5494
<212> TYPE: DNA
<213> ORGANISM: Homo sapiens
<220> FEATURE:
<221> NAME/KEY: CDS
<222> LOCATION: (155)..(4810)

<400> SEQUENCE: 45
gcagagctgc agaggcaccg gacgagagag ggctccgcgg gcccagctgg cagccaggcc    60
```

```
ggagacaagt tgcagtcccg ggctctggtg acgccgtggc cgcagggtct ccattttggg        120
acattctaat ccctgagccc ctattatttt catc atg ggc ttc tgc ctg gct cta        175
                                     Met Gly Phe Cys Leu Ala Leu
                                      1               5 gca tgg aca ctt ctg gtt ggg gca tgg acc cct ctg gga gct cag aac          223
Ala Trp Thr Leu Leu Val Gly Ala Trp Thr Pro Leu Gly Ala Gln Asn
             10                  15                  20 ccc att tcg tgg gag gtg cag cga ttt gat ggg tgg tac aac aac ctc          271
Pro Ile Ser Trp Glu Val Gln Arg Phe Asp Gly Trp Tyr Asn Asn Leu
         25                  30                  35 atg gag cac aga tgg ggc agc aaa ggt tcc cgg ctg cag cgc ctg gtc          319
Met Glu His Arg Trp Gly Ser Lys Gly Ser Arg Leu Gln Arg Leu Val
 40                  45                  50                  55 cca gcc agc tat gca gat ggc gtg tac cag ccc ttg gga gaa ccc cac          367
Pro Ala Ser Tyr Ala Asp Gly Val Tyr Gln Pro Leu Gly Glu Pro His
                 60                  65                  70 ctg ccc aac ccc cga gac ctt agc aac acc atc tca agg ggc cct gca          415
Leu Pro Asn Pro Arg Asp Leu Ser Asn Thr Ile Ser Arg Gly Pro Ala
             75                  80                  85 ggg ctg gcc tcc ctg aga aac cgc aca gtg ttg ggg gtc ttc ttt ggc          463
Gly Leu Ala Ser Leu Arg Asn Arg Thr Val Leu Gly Val Phe Phe Gly
         90                  95                 100 tat cac gtg ctt tca gac ctg gtg agc gtg gaa act ccc ggc tgc ccc          511
Tyr His Val Leu Ser Asp Leu Val Ser Val Glu Thr Pro Gly Cys Pro
105                 110                 115 gcc gag ttc ctc aac att cgc atc ccg ccc gga gac ccc atg ttc gac          559
Ala Glu Phe Leu Asn Ile Arg Ile Pro Pro Gly Asp Pro Met Phe Asp
120                 125                 130                 135 ccc gac cag cgc ggg gac gtg gtg ctg ccc ttc cag aga agc cgc tgg          607
Pro Asp Gln Arg Gly Asp Val Val Leu Pro Phe Gln Arg Ser Arg Trp
                140                 145                 150 gac ccc gag acc gga cgg agt ccc agc aat ccc cgg gac ccg gcc aac          655
Asp Pro Glu Thr Gly Arg Ser Pro Ser Asn Pro Arg Asp Pro Ala Asn
            155                 160                 165 cag gtg acg ggc tgg ctg gac ggc agc gcc atc tat ggt tcc tcg cat          703
Gln Val Thr Gly Trp Leu Asp Gly Ser Ala Ile Tyr Gly Ser Ser His
        170                 175                 180 tcc tgg agc gac gcg ctg cgg agc ttc tcc agg gga cag ctg gcg tcg          751
Ser Trp Ser Asp Ala Leu Arg Ser Phe Ser Arg Gly Gln Leu Ala Ser
185                 190                 195 ggg ccc gac ccc gct ttt ccc cga gac tcg cag aac ccc ctg ctc atg          799
Gly Pro Asp Pro Ala Phe Pro Arg Asp Ser Gln Asn Pro Leu Leu Met
200                 205                 210                 215 tgg gcg gcg ccc gac ccc gcc acc ggg cag aac ggg ccc cgg ggg ctg          847
Trp Ala Ala Pro Asp Pro Ala Thr Gly Gln Asn Gly Pro Arg Gly Leu
                220                 225                 230 tac gcc ttc ggg gca gag aga ggg aac cgg gaa ccc ttc ctg cag gcg          895
Tyr Ala Phe Gly Ala Glu Arg Gly Asn Arg Glu Pro Phe Leu Gln Ala
            235                 240                 245 ctg ggc ctg ctc tgg ttc cgc tac cac aac ctg tgg gcg cag agg ctg          943
Leu Gly Leu Leu Trp Phe Arg Tyr His Asn Leu Trp Ala Gln Arg Leu
        250                 255                 260 gcc cgc cag cac cca gac tgg gag gac gag gag ctg ttc cag cac gca          991
Ala Arg Gln His Pro Asp Trp Glu Asp Glu Glu Leu Phe Gln His Ala
265                 270                 275 cgc aag agg gtc atc gcc acc tac cag aac atc gct gtg tat gag tgg          1039
Arg Lys Arg Val Ile Ala Thr Tyr Gln Asn Ile Ala Val Tyr Glu Trp
280                 285                 290                 295 ctg ccc agc ttc ctg cag aaa aca ctc ccg gag tat aca gga tac cgg          1087
```

```
                                    -continued

Leu Pro Ser Phe Leu Gln Lys Thr Leu Pro Glu Tyr Thr Gly Tyr Arg
                300                 305                 310 cca ttt ctg gac ccc agc atc tcc tca gag ttc gtg gcg gcc tct gag      1135
Pro Phe Leu Asp Pro Ser Ile Ser Ser Glu Phe Val Ala Ala Ser Glu
            315                 320                 325 cag ttc ctg tcc acc atg gtg ccc cct ggc gtc tac atg aga aat gcc      1183
Gln Phe Leu Ser Thr Met Val Pro Pro Gly Val Tyr Met Arg Asn Ala
        330                 335                 340 agc tgc cac ttc cag ggg gtc atc aat cgg aac tca agt gtc tcc aga      1231
Ser Cys His Phe Gln Gly Val Ile Asn Arg Asn Ser Ser Val Ser Arg
    345                 350                 355 gct ctc cgg gtc tgc aac agc tac tgg agc cgt gag cac cca agc cta      1279
Ala Leu Arg Val Cys Asn Ser Tyr Trp Ser Arg Glu His Pro Ser Leu
360                 365                 370                 375 caa agt gct gaa gat gtg gat gca ctg ctg ctg ggc atg gcc tcc cag      1327
Gln Ser Ala Glu Asp Val Asp Ala Leu Leu Leu Gly Met Ala Ser Gln
            380                 385                 390 atc gca gag cga gag gac cat gtg ttg gtt gaa gat gtg cgg gat ttc      1375
Ile Ala Glu Arg Glu Asp His Val Leu Val Glu Asp Val Arg Asp Phe
        395                 400                 405 tgg cct ggg cca ctg aag ttt tcc cgc aca gac cac ctg gcc agc tgc      1423
Trp Pro Gly Pro Leu Lys Phe Ser Arg Thr Asp His Leu Ala Ser Cys
    410                 415                 420 ctg cag cgg ggc cgg gat ctg ggc ctg ccc tct tac acc aag gcc agg      1471
Leu Gln Arg Gly Arg Asp Leu Gly Leu Pro Ser Tyr Thr Lys Ala Arg
425                 430                 435 gca gca ctg ggc ttg tct ccc att acc cgc tgg cag gac atc aac cct      1519
Ala Ala Leu Gly Leu Ser Pro Ile Thr Arg Trp Gln Asp Ile Asn Pro
440                 445                 450                 455 gca ctc tcc cgg agc aat gac act gta ctg gag gcc aca gct gcc ctg      1567
Ala Leu Ser Arg Ser Asn Asp Thr Val Leu Glu Ala Thr Ala Ala Leu
            460                 465                 470 tac aac cag gac tta tcc tgg cta gag ctg ctc cct ggg gga ctc ctg      1615
Tyr Asn Gln Asp Leu Ser Trp Leu Glu Leu Leu Pro Gly Gly Leu Leu
        475                 480                 485 gag agc cac cgg gac cct gga cct ctg ttc agc acc atc gtc ctt gaa      1663
Glu Ser His Arg Asp Pro Gly Pro Leu Phe Ser Thr Ile Val Leu Glu
    490                 495                 500 caa ttt gtg cgg cta cgg gat ggt gac cgc tac tgg ttt gag aac acc      1711
Gln Phe Val Arg Leu Arg Asp Gly Asp Arg Tyr Trp Phe Glu Asn Thr
505                 510                 515 agg aat ggg ctg ttc tcc aag aag gag att gaa gaa atc cga aat acc      1759
Arg Asn Gly Leu Phe Ser Lys Lys Glu Ile Glu Glu Ile Arg Asn Thr
520                 525                 530                 535 acc ctg cag gac gtg ctg gtc gct gtt atc aac att gac ccc agt gct      1807
Thr Leu Gln Asp Val Leu Val Ala Val Ile Asn Ile Asp Pro Ser Ala
            540                 545                 550 ctg cag ccc aat gtc ttt gtc tgg cat aaa gga gac ccc tgt ccg cag      1855
Leu Gln Pro Asn Val Phe Val Trp His Lys Gly Asp Pro Cys Pro Gln
        555                 560                 565 ccg aga cag ctc agc act gaa ggc ctg cca gcg tgt gct ccc tct gtt      1903
Pro Arg Gln Leu Ser Thr Glu Gly Leu Pro Ala Cys Ala Pro Ser Val
    570                 575                 580 gtt cgt gac tat ttt gag ggc agt gga ttt ggc ttc ggg gtc acc atc      1951
Val Arg Asp Tyr Phe Glu Gly Ser Gly Phe Gly Phe Gly Val Thr Ile
585                 590                 595 ggg acc ctc tgt tgc ttc cct ttg gtg agc ctg ctc agt gcc tgg att      1999
Gly Thr Leu Cys Cys Phe Pro Leu Val Ser Leu Leu Ser Ala Trp Ile
600                 605                 610                 615
```

```
                                                    -continued gtt gcc cgg ctc cgg atg aga aat ttc aag agg ctc cag ggc cag gac    2047
Val Ala Arg Leu Arg Met Arg Asn Phe Lys Arg Leu Gln Gly Gln Asp
            620                 625                 630 cgc cag agc atc gtg tct gag aag ctc gtg gga ggc atg gaa gct ttg    2095
Arg Gln Ser Ile Val Ser Glu Lys Leu Val Gly Gly Met Glu Ala Leu
                635                 640                 645 gaa tgg caa ggc cac aag gag ccc tgc cgg ccc gtg ctt gtg tac ctg    2143
Glu Trp Gln Gly His Lys Glu Pro Cys Arg Pro Val Leu Val Tyr Leu
        650                 655                 660 cag ccc ggg cag atc cgt gtg gta gat ggc agg ctc acc gtg ctc cgc    2191
Gln Pro Gly Gln Ile Arg Val Val Asp Gly Arg Leu Thr Val Leu Arg
    665                 670                 675 acc atc cag ctg cag cct cca cag aag gtc aac ttc gtc ctg tcc agc    2239
Thr Ile Gln Leu Gln Pro Pro Gln Lys Val Asn Phe Val Leu Ser Ser
680                 685                 690                 695 aac cgt gga cgc cgc act ctg ctg ctc aag atc ccc aag gag tat gac    2287
Asn Arg Gly Arg Arg Thr Leu Leu Leu Lys Ile Pro Lys Glu Tyr Asp
                700                 705                 710 ctg gtg ctg ctg ttt aac ttg gag gaa gag cgg cag gcg ctg gtg gaa    2335
Leu Val Leu Leu Phe Asn Leu Glu Glu Glu Arg Gln Ala Leu Val Glu
        715                 720                 725 aat ctc cgg gga gct ctg aag gag agc ggg ttg agc atc cag gag tgg    2383
Asn Leu Arg Gly Ala Leu Lys Glu Ser Gly Leu Ser Ile Gln Glu Trp
    730                 735                 740 gag ctg cgg gag cag gag ctg atg aga gca gct gtg aca cgg gag cag    2431
Glu Leu Arg Glu Gln Glu Leu Met Arg Ala Ala Val Thr Arg Glu Gln
745                 750                 755 cgg agg cac ctc ctg gag acc ttt ttc agg cac ctt ttc tcc cag gtg    2479
Arg Arg His Leu Leu Glu Thr Phe Phe Arg His Leu Phe Ser Gln Val
760                 765                 770                 775 ctg gac atc aac cag gcc gac gca ggg acc ctg ccc ctg gac tcc tcc    2527
Leu Asp Ile Asn Gln Ala Asp Ala Gly Thr Leu Pro Leu Asp Ser Ser
                780                 785                 790 cag aag gtg cgg gag gcc ctg acc tgt gag ctg agc agg gcc gag ttt    2575
Gln Lys Val Arg Glu Ala Leu Thr Cys Glu Leu Ser Arg Ala Glu Phe
        795                 800                 805 gcc gag tcc ctg ggc ctc aag ccc cag gac atg ttt gtg gag tcc atg    2623
Ala Glu Ser Leu Gly Leu Lys Pro Gln Asp Met Phe Val Glu Ser Met
    810                 815                 820 ttc tct ctg gct gac aag gat ggc aat ggc tac ctg tcc ttc cga gag    2671
Phe Ser Leu Ala Asp Lys Asp Gly Asn Gly Tyr Leu Ser Phe Arg Glu
825                 830                 835 ttc ctg gac atc ctg gtg gtc ttc atg aaa ggc tct cct gag gaa aag    2719
Phe Leu Asp Ile Leu Val Val Phe Met Lys Gly Ser Pro Glu Glu Lys
840                 845                 850                 855 tct cgc ctt atg ttc cgc atg tac gac ttt gat ggg aat ggc ctc att    2767
Ser Arg Leu Met Phe Arg Met Tyr Asp Phe Asp Gly Asn Gly Leu Ile
                860                 865                 870 tcc aag gat gag ttc atc agg atg ctg aga tcc ttc atc gag atc tcc    2815
Ser Lys Asp Glu Phe Ile Arg Met Leu Arg Ser Phe Ile Glu Ile Ser
        875                 880                 885 aac aac tgc ctg tcc aag gcc cag ctg gct gag gtg gtg gag tcc atg    2863
Asn Asn Cys Leu Ser Lys Ala Gln Leu Ala Glu Val Val Glu Ser Met
    890                 895                 900 ttc cgg gag tcg gga ttc cag gac aag gag gaa ctg aca tgg gaa gat    2911
Phe Arg Glu Ser Gly Phe Gln Asp Lys Glu Glu Leu Thr Trp Glu Asp
905                 910                 915 ttt cac ttc atg ctg cgg gac cac aat agc gag ctc cgc ttc acg cag    2959
Phe His Phe Met Leu Arg Asp His Asn Ser Glu Leu Arg Phe Thr Gln
920                 925                 930                 935
```

-continued

```
ctc tgt gtc aaa ggg gtg gag gtg cct gaa gtc atc aag gac ctc tgc      3007
Leu Cys Val Lys Gly Val Glu Val Pro Glu Val Ile Lys Asp Leu Cys
            940                 945                 950 cgg cga gcc tcc tac atc agc cag gat atg atc tgt ccc tct ccc aga      3055
Arg Arg Ala Ser Tyr Ile Ser Gln Asp Met Ile Cys Pro Ser Pro Arg
        955                 960                 965 gtg agt gcc cgc tgt tcc cgc agc gac att gag act gag ttg aca cct      3103
Val Ser Ala Arg Cys Ser Arg Ser Asp Ile Glu Thr Glu Leu Thr Pro
    970                 975                 980 cag aga ctg cag tgc ccc atg gac aca gac cct ccc cag gag att cgg      3151
Gln Arg Leu Gln Cys Pro Met Asp Thr Asp Pro Pro Gln Glu Ile Arg
985                 990                 995 cgg agg ttt ggc aag aag gta acg tca ttc cag ccc ttg ctg ttc act      3199
Arg Arg Phe Gly Lys Lys Val Thr Ser Phe Gln Pro Leu Leu Phe Thr
1000                1005                1010                1015 gag gcg cac cga gag aag ttc caa cgc agc tgt ctc cac cag acg gtg      3247
Glu Ala His Arg Glu Lys Phe Gln Arg Ser Cys Leu His Gln Thr Val
                1020                1025                1030 caa cag ttc aag cgc ttc att gag aac tac cgg cgc cac atc ggc tgc      3295
Gln Gln Phe Lys Arg Phe Ile Glu Asn Tyr Arg Arg His Ile Gly Cys
            1035                1040                1045 gtg gcc gtg ttc tac gcc atc gct ggg ggg ctt ttc ctg gag agg gcc      3343
Val Ala Val Phe Tyr Ala Ile Ala Gly Gly Leu Phe Leu Glu Arg Ala
        1050                1055                1060 tac tac tac gcc ttt gcc gca cat cac acg ggc atc acg gac acc acc      3391
Tyr Tyr Tyr Ala Phe Ala Ala His His Thr Gly Ile Thr Asp Thr Thr
    1065                1070                1075 cgc gtg gga atc atc ctg tcg cgg ggc aca gca gcc agc atc tct ttc      3439
Arg Val Gly Ile Ile Leu Ser Arg Gly Thr Ala Ala Ser Ile Ser Phe
1080                1085                1090                1095 atg ttc tcc tac atc ttg ctc acc atg tgc cgc aac ctc atc acc ttc      3487
Met Phe Ser Tyr Ile Leu Leu Thr Met Cys Arg Asn Leu Ile Thr Phe
                1100                1105                1110 ctg cga gaa acc ttc ctc aac cgc tac gtg ccc ttc gac gcc gcc gtg      3535
Leu Arg Glu Thr Phe Leu Asn Arg Tyr Val Pro Phe Asp Ala Ala Val
            1115                1120                1125 gac ttc cat cgc ctc att gcc tcc acc gcc atc gtc ctc aca gtc tta      3583
Asp Phe His Arg Leu Ile Ala Ser Thr Ala Ile Val Leu Thr Val Leu
        1130                1135                1140 cac agt gtg ggc cat gtg gtg aat gtg tac ctg ttc tcc atc agc ccc      3631
His Ser Val Gly His Val Val Asn Val Tyr Leu Phe Ser Ile Ser Pro
    1145                1150                1155 ctc agc gtc ctc tct tgc ctc ttt cct ggc ctc ttc cat gat gat ggg      3679
Leu Ser Val Leu Ser Cys Leu Phe Pro Gly Leu Phe His Asp Asp Gly
1160                1165                1170                1175 tct gag ttc ccc cag aag tat tac tgg tgg ttc ttc cag acc gta cca      3727
Ser Glu Phe Pro Gln Lys Tyr Tyr Trp Trp Phe Phe Gln Thr Val Pro
                1180                1185                1190 ggc ctc acg ggg gtt gtg ctg ctc ctg atc ctg gcc atc atg tat gtc      3775
Gly Leu Thr Gly Val Val Leu Leu Leu Ile Leu Ala Ile Met Tyr Val
            1195                1200                1205 ttt gcc tcc cac cac ttc cgc cgc cgc agt ttc cgg ggc ttc tgg ctg      3823
Phe Ala Ser His His Phe Arg Arg Arg Ser Phe Arg Gly Phe Trp Leu
        1210                1215                1220 acc cac cac ctc tac atc ctg ctc tat gtc ctg ctc atc atc cat ggt      3871
Thr His His Leu Tyr Ile Leu Leu Tyr Val Leu Leu Ile Ile His Gly
    1225                1230                1235 agc ttt gcc ctg atc cag ctg ccc cgt ttc cac atc ttc ttc ctg gtc      3919
Ser Phe Ala Leu Ile Gln Leu Pro Arg Phe His Ile Phe Phe Leu Val
```

-continued

| | |
|---|---|
| cca gca atc atc tat ggg ggc gac aag ctg gtg agc ctg agc cgg aag<br>Pro Ala Ile Ile Tyr Gly Gly Asp Lys Leu Val Ser Leu Ser Arg Lys<br>1260                    1265                 1270 | 3967 |
| aag gtg gag atc agc gtg gtg aag gcg gag ctg ctg ccc tca gga gtg<br>Lys Val Glu Ile Ser Val Val Lys Ala Glu Leu Leu Pro Ser Gly Val<br>    1275                  1280                1285 | 4015 |
| acc cac ctg cgg ttc cag cgg ccc cag ggc ttt gag tac aag tca ggg<br>Thr His Leu Arg Phe Gln Arg Pro Gln Gly Phe Glu Tyr Lys Ser Gly<br>        1290                 1295              1300 | 4063 |
| cag tgg gtg cgg atc gct tgc ctg gct ctg ggg acc acc gag tac cac<br>Gln Trp Val Arg Ile Ala Cys Leu Ala Leu Gly Thr Thr Glu Tyr His<br>1305                    1310                1315 | 4111 |
| ccc ttc aca ctg acc tct gcg ccc cat gag gac acg ctt agc ctg cac<br>Pro Phe Thr Leu Thr Ser Ala Pro His Glu Asp Thr Leu Ser Leu His<br>1320                    1325                1330              1335 | 4159 |
| atc cgg gca gca ggg ccc tgg acc act cgc ctc agg gag atc tac tca<br>Ile Arg Ala Ala Gly Pro Trp Thr Thr Arg Leu Arg Glu Ile Tyr Ser<br>            1340                 1345                1350 | 4207 |
| gcc ccg acg ggt gac aga tgt gcc aga tac cca aag ctg tac ctt gat<br>Ala Pro Thr Gly Asp Arg Cys Ala Arg Tyr Pro Lys Leu Tyr Leu Asp<br>            1355                 1360                1365 | 4255 |
| gga cca ttt gga gag ggc cac cag gag tgg cat aag ttt gag gtg tca<br>Gly Pro Phe Gly Glu Gly His Gln Glu Trp His Lys Phe Glu Val Ser<br>1370                    1375                1380 | 4303 |
| gtg tta gtg gga ggg ggc att ggg gtc acc cct ttt gcc tcc atc ctc<br>Val Leu Val Gly Gly Gly Ile Gly Val Thr Pro Phe Ala Ser Ile Leu<br>1385                    1390                1395 | 4351 |
| aaa gac ctg gtc ttc aag tca tcc gtc agc tgc caa gtg ttc tgt aag<br>Lys Asp Leu Val Phe Lys Ser Ser Val Ser Cys Gln Val Phe Cys Lys<br>1400                    1405                1410              1415 | 4399 |
| aag atc tac ttc atc tgg gtg acg cgg acc cag cgt cag ttt gag tgg<br>Lys Ile Tyr Phe Ile Trp Val Thr Arg Thr Gln Arg Gln Phe Glu Trp<br>            1420                 1425                1430 | 4447 |
| ctg gct gac atc atc cga gag gtg gag gag aat gac cac cag gac ctg<br>Leu Ala Asp Ile Ile Arg Glu Val Glu Glu Asn Asp His Gln Asp Leu<br>        1435                 1440                1445 | 4495 |
| gtg tct gtg cac atc tac atc acc cag ctg gct gag aag ttc gac ctc<br>Val Ser Val His Ile Tyr Ile Thr Gln Leu Ala Glu Lys Phe Asp Leu<br>1450                    1455                1460 | 4543 |
| agg acc act atg ctg tac atc tgt gag cgg cac ttc cag aag gtt ctg<br>Arg Thr Thr Met Leu Tyr Ile Cys Glu Arg His Phe Gln Lys Val Leu<br>1465                    1470                1475 | 4591 |
| aac cgg agt cta ttc aca ggc ctg cgc tcc atc acc cac ttt ggc cgt<br>Asn Arg Ser Leu Phe Thr Gly Leu Arg Ser Ile Thr His Phe Gly Arg<br>1480                    1485                1490              1495 | 4639 |
| ccc ccc ttt gag ccc ttc ttc aac tcc ctg cag gag gtc cac ccc cag<br>Pro Pro Phe Glu Pro Phe Phe Asn Ser Leu Gln Glu Val His Pro Gln<br>            1500                 1505                1510 | 4687 |
| gtc cgg aag atc ggg gtg ttt agc tgt ggc ccc cct ggc atg acc aag<br>Val Arg Lys Ile Gly Val Phe Ser Cys Gly Pro Pro Gly Met Thr Lys<br>        1515                 1520                1525 | 4735 |
| aat gtg gaa aag gcc tgt cag ctc atc aac agg cag gac cgg act cac<br>Asn Val Glu Lys Ala Cys Gln Leu Ile Asn Arg Gln Asp Arg Thr His<br>1530                    1535                1540 | 4783 |
| ttc tcc cac cat tat gag aac ttc tag gcccctgccc gggggttctg<br>Phe Ser His His Tyr Glu Asn Phe<br>1545                    1550 | 4830 |
| cccactgtcc agttgagcag aggtttgagc ccacacctca cctctgttct tcctatttct | 4890 |

-continued

```
ggctgcctca gccttctctg atttcccacc tcccaacctt gttccaggtg gccatagtca   4950
gtcaccatgt gtgggctcag ggacccccag gaccaggatg tgtctcagcc tggagaaatg   5010
gtgggggggc agtgtctagg gactagagtg agaagtaggg gagctactga tttggggcaa   5070
agtgaaacct ctgcttcaga cttcagaaac aaatctcaga agacaagctg acctgacaag   5130
tactatgtgt gtgcatgtct gtatgtgtgt tggggcggtg agtgtaagga tgcagtggga   5190
gcatggatgc tggcatctta gaaccctccc tactcccata cctcctcctc ttctgggctc   5250
cccactgtca gacgggctgg caaatgcctt gcaggaggta gaggctggac ccatggcaag   5310
ccatttacag aaacccactc ggcaccccag tctaacacca caactaattt cacccaaggt   5370
tttaagcacg ttctttcatc agaccctggc ccaataccta tgtatgcaat gctcctcagc   5430
cctcttctcc ctgctccagt agtctccctt ccaaataaat cacttttctg ccaaaaaaaa   5490
aaaa                                                                5494
```

```

<210> SEQ ID NO 46
<211> LENGTH: 1551
<212> TYPE: PRT
<213> ORGANISM: Homo sapiens

<400> SEQUENCE: 46

Met Gly Phe Cys Leu Ala Leu Ala Trp Thr Leu Leu Val Gly Ala Trp
1               5                   10                  15

Thr Pro Leu Gly Ala Gln Asn Pro Ile Ser Trp Glu Val Gln Arg Phe
            20                  25                  30

Asp Gly Trp Tyr Asn Asn Leu Met Glu His Arg Trp Gly Ser Lys Gly
        35                  40                  45

Ser Arg Leu Gln Arg Leu Val Pro Ala Ser Tyr Ala Asp Gly Val Tyr
    50                  55                  60

Gln Pro Leu Gly Glu Pro His Leu Pro Asn Pro Arg Asp Leu Ser Asn
65                  70                  75                  80

Thr Ile Ser Arg Gly Pro Ala Gly Leu Ala Ser Leu Arg Asn Arg Thr
                85                  90                  95

Val Leu Gly Val Phe Phe Gly Tyr His Val Leu Ser Asp Leu Val Ser
            100                 105                 110

Val Glu Thr Pro Gly Cys Pro Ala Glu Phe Leu Asn Ile Arg Ile Pro
        115                 120                 125

Pro Gly Asp Pro Met Phe Asp Pro Asp Gln Arg Gly Asp Val Val Leu
    130                 135                 140

Pro Phe Gln Arg Ser Arg Trp Asp Pro Glu Thr Gly Arg Ser Pro Ser
145                 150                 155                 160

Asn Pro Arg Asp Pro Ala Asn Gln Val Thr Gly Trp Leu Asp Gly Ser
                165                 170                 175

Ala Ile Tyr Gly Ser Ser His Ser Trp Ser Asp Ala Leu Arg Ser Phe
            180                 185                 190

Ser Arg Gly Gln Leu Ala Ser Gly Pro Asp Pro Ala Phe Pro Arg Asp
        195                 200                 205

Ser Gln Asn Pro Leu Leu Met Trp Ala Ala Pro Asp Pro Ala Thr Gly
    210                 215                 220

Gln Asn Gly Pro Arg Gly Leu Tyr Ala Phe Gly Ala Glu Arg Gly Asn
225                 230                 235                 240

Arg Glu Pro Phe Leu Gln Ala Leu Gly Leu Leu Trp Phe Arg Tyr His
                245                 250                 255
```

-continued

```
Asn Leu Trp Ala Gln Arg Leu Ala Arg Gln His Pro Asp Trp Glu Asp
            260                 265                 270
Glu Glu Leu Phe Gln His Ala Arg Lys Arg Val Ile Ala Thr Tyr Gln
        275                 280                 285
Asn Ile Ala Val Tyr Glu Trp Leu Pro Ser Phe Leu Gln Lys Thr Leu
    290                 295                 300
Pro Glu Tyr Thr Gly Tyr Arg Pro Phe Leu Asp Pro Ser Ile Ser Ser
305                 310                 315                 320
Glu Phe Val Ala Ala Ser Glu Gln Phe Leu Ser Thr Met Val Pro Pro
                325                 330                 335
Gly Val Tyr Met Arg Asn Ala Ser Cys His Phe Gln Gly Val Ile Asn
            340                 345                 350
Arg Asn Ser Ser Val Ser Arg Ala Leu Arg Val Cys Asn Ser Tyr Trp
        355                 360                 365
Ser Arg Glu His Pro Ser Leu Gln Ser Ala Glu Asp Val Asp Ala Leu
    370                 375                 380
Leu Leu Gly Met Ala Ser Gln Ile Ala Glu Arg Glu Asp His Val Leu
385                 390                 395                 400
Val Glu Asp Val Arg Asp Phe Trp Pro Gly Pro Leu Lys Phe Ser Arg
                405                 410                 415
Thr Asp His Leu Ala Ser Cys Leu Gln Arg Gly Arg Asp Leu Gly Leu
            420                 425                 430
Pro Ser Tyr Thr Lys Ala Arg Ala Leu Gly Leu Ser Pro Ile Thr
        435                 440                 445
Arg Trp Gln Asp Ile Asn Pro Ala Leu Ser Arg Ser Asn Asp Thr Val
    450                 455                 460
Leu Glu Ala Thr Ala Ala Leu Tyr Asn Gln Asp Leu Ser Trp Leu Glu
465                 470                 475                 480
Leu Leu Pro Gly Gly Leu Leu Glu Ser His Arg Asp Pro Gly Pro Leu
                485                 490                 495
Phe Ser Thr Ile Val Leu Glu Gln Phe Val Arg Leu Arg Asp Gly Asp
            500                 505                 510
Arg Tyr Trp Phe Glu Asn Thr Arg Asn Gly Leu Phe Ser Lys Lys Glu
        515                 520                 525
Ile Glu Glu Ile Arg Asn Thr Thr Leu Gln Asp Val Leu Val Ala Val
    530                 535                 540
Ile Asn Ile Asp Pro Ser Ala Leu Gln Pro Asn Val Phe Val Trp His
545                 550                 555                 560
Lys Gly Asp Pro Cys Pro Gln Pro Arg Gln Leu Ser Thr Glu Gly Leu
                565                 570                 575
Pro Ala Cys Ala Pro Ser Val Val Arg Asp Tyr Phe Glu Gly Ser Gly
            580                 585                 590
Phe Gly Phe Gly Val Thr Ile Gly Thr Leu Cys Cys Phe Pro Leu Val
        595                 600                 605
Ser Leu Leu Ser Ala Trp Ile Val Ala Arg Leu Arg Met Arg Asn Phe
    610                 615                 620
Lys Arg Leu Gln Gly Gln Asp Arg Gln Ser Ile Val Ser Glu Lys Leu
625                 630                 635                 640
Val Gly Met Glu Ala Leu Glu Trp Gln Gly His Lys Glu Pro Cys
                645                 650                 655
Arg Pro Val Leu Val Tyr Leu Gln Pro Gly Gln Ile Arg Val Val Asp
            660                 665                 670
Gly Arg Leu Thr Val Leu Arg Thr Ile Gln Leu Gln Pro Pro Gln Lys
```

-continued

```
            675                 680                 685
Val Asn Phe Val Leu Ser Ser Asn Arg Gly Arg Arg Thr Leu Leu Leu
    690                 695                 700
Lys Ile Pro Lys Glu Tyr Asp Leu Val Leu Leu Phe Asn Leu Glu Glu
705                 710                 715                 720
Glu Arg Gln Ala Leu Val Glu Asn Leu Arg Gly Ala Leu Lys Glu Ser
                725                 730                 735
Gly Leu Ser Ile Gln Glu Trp Glu Leu Arg Glu Gln Glu Leu Met Arg
                740                 745                 750
Ala Ala Val Thr Arg Glu Gln Arg Arg His Leu Leu Glu Thr Phe Phe
                755                 760                 765
Arg His Leu Phe Ser Gln Val Leu Asp Ile Asn Gln Ala Asp Ala Gly
                770                 775                 780
Thr Leu Pro Leu Asp Ser Ser Gln Lys Val Arg Glu Ala Leu Thr Cys
785                 790                 795                 800
Glu Leu Ser Arg Ala Glu Phe Ala Glu Ser Leu Gly Leu Lys Pro Gln
                805                 810                 815
Asp Met Phe Val Glu Ser Met Phe Ser Leu Ala Asp Lys Asp Gly Asn
                820                 825                 830
Gly Tyr Leu Ser Phe Arg Glu Phe Leu Asp Ile Leu Val Val Phe Met
                835                 840                 845
Lys Gly Ser Pro Glu Glu Lys Ser Arg Leu Met Phe Arg Met Tyr Asp
    850                 855                 860
Phe Asp Gly Asn Gly Leu Ile Ser Lys Asp Glu Phe Ile Arg Met Leu
865                 870                 875                 880
Arg Ser Phe Ile Glu Ile Ser Asn Asn Cys Leu Ser Lys Ala Gln Leu
                885                 890                 895
Ala Glu Val Val Glu Ser Met Phe Arg Glu Ser Gly Phe Gln Asp Lys
                900                 905                 910
Glu Glu Leu Thr Trp Glu Asp Phe His Phe Met Leu Arg Asp His Asn
                915                 920                 925
Ser Glu Leu Arg Phe Thr Gln Leu Cys Val Lys Gly Val Glu Val Pro
    930                 935                 940
Glu Val Ile Lys Asp Leu Cys Arg Arg Ala Ser Tyr Ile Ser Gln Asp
945                 950                 955                 960
Met Ile Cys Pro Ser Pro Arg Val Ser Ala Arg Cys Ser Arg Ser Asp
                965                 970                 975
Ile Glu Thr Glu Leu Thr Pro Gln Arg Leu Gln Cys Pro Met Asp Thr
                980                 985                 990
Asp Pro Pro Gln Glu Ile Arg Arg Arg Phe Gly Lys Lys Val Thr Ser
                995                 1000                1005
Phe Gln Pro Leu Leu Phe Thr Glu Ala His Arg Glu Lys Phe Gln
    1010                1015                1020
Arg Ser Cys Leu His Gln Thr Val Gln Gln Phe Lys Arg Phe Ile
    1025                1030                1035
Glu Asn Tyr Arg Arg His Ile Gly Cys Val Ala Val Phe Tyr Ala
    1040                1045                1050
Ile Ala Gly Gly Leu Phe Leu Glu Arg Ala Tyr Tyr Tyr Ala Phe
    1055                1060                1065
Ala Ala His His Thr Gly Ile Thr Asp Thr Thr Arg Val Gly Ile
    1070                1075                1080
Ile Leu Ser Arg Gly Thr Ala Ala Ser Ile Ser Phe Met Phe Ser
    1085                1090                1095
```

```
Tyr Ile Leu Leu Thr Met Cys Arg Asn Leu Ile Thr Phe Leu Arg
    1100                1105                1110

Glu Thr Phe Leu Asn Arg Tyr Val Pro Phe Asp Ala Ala Val Asp
    1115                1120                1125

Phe His Arg Leu Ile Ala Ser Thr Ala Ile Val Leu Thr Val Leu
    1130                1135                1140

His Ser Val Gly His Val Val Asn Val Tyr Leu Phe Ser Ile Ser
    1145                1150                1155

Pro Leu Ser Val Leu Ser Cys Leu Phe Pro Gly Leu Phe His Asp
    1160                1165                1170

Asp Gly Ser Glu Phe Pro Gln Lys Tyr Trp Trp Phe Phe Gln
    1175                1180                1185

Thr Val Pro Gly Leu Thr Gly Val Val Leu Leu Ile Leu Ala
    1190                1195                1200

Ile Met Tyr Val Phe Ala Ser His His Phe Arg Arg Arg Ser Phe
    1205                1210                1215

Arg Gly Phe Trp Leu Thr His His Leu Tyr Ile Leu Leu Tyr Val
    1220                1225                1230

Leu Leu Ile Ile His Gly Ser Phe Ala Leu Ile Gln Leu Pro Arg
    1235                1240                1245

Phe His Ile Phe Phe Leu Val Pro Ala Ile Ile Tyr Gly Gly Asp
    1250                1255                1260

Lys Leu Val Ser Leu Ser Arg Lys Lys Val Glu Ile Ser Val Val
    1265                1270                1275

Lys Ala Glu Leu Leu Pro Ser Gly Val Thr His Leu Arg Phe Gln
    1280                1285                1290

Arg Pro Gln Gly Phe Glu Tyr Lys Ser Gly Gln Trp Val Arg Ile
    1295                1300                1305

Ala Cys Leu Ala Leu Gly Thr Thr Glu Tyr His Pro Phe Thr Leu
    1310                1315                1320

Thr Ser Ala Pro His Glu Asp Thr Leu Ser Leu His Ile Arg Ala
    1325                1330                1335

Ala Gly Pro Trp Thr Thr Arg Leu Arg Glu Ile Tyr Ser Ala Pro
    1340                1345                1350

Thr Gly Asp Arg Cys Ala Arg Tyr Pro Lys Leu Tyr Leu Asp Gly
    1355                1360                1365

Pro Phe Gly Glu Gly His Gln Glu Trp His Lys Phe Glu Val Ser
    1370                1375                1380

Val Leu Val Gly Gly Gly Ile Gly Val Thr Pro Phe Ala Ser Ile
    1385                1390                1395

Leu Lys Asp Leu Val Phe Lys Ser Ser Val Ser Cys Gln Val Phe
    1400                1405                1410

Cys Lys Lys Ile Tyr Phe Ile Trp Val Thr Arg Thr Gln Arg Gln
    1415                1420                1425

Phe Glu Trp Leu Ala Asp Ile Ile Arg Glu Val Glu Glu Asn Asp
    1430                1435                1440

His Gln Asp Leu Val Ser Val His Ile Tyr Ile Thr Gln Leu Ala
    1445                1450                1455

Glu Lys Phe Asp Leu Arg Thr Thr Met Leu Tyr Ile Cys Glu Arg
    1460                1465                1470

His Phe Gln Lys Val Leu Asn Arg Ser Leu Phe Thr Gly Leu Arg
    1475                1480                1485
```

```
Ser Ile Thr His Phe Gly Arg Pro Pro Phe Glu Pro Phe Phe Asn
    1490                1495                1500

Ser Leu Gln Glu Val His Pro Gln Val Arg Lys Ile Gly Val Phe
    1505                1510                1515

Ser Cys Gly Pro Pro Gly Met Thr Lys Asn Val Glu Lys Ala Cys
    1520                1525                1530

Gln Leu Ile Asn Arg Gln Asp Arg Thr His Phe Ser His His Tyr
    1535                1540                1545

Glu Asn Phe
    1550

<210> SEQ ID NO 47
<211> LENGTH: 3453
<212> TYPE: DNA
<213> ORGANISM: Homo sapiens
<220> FEATURE:
<221> NAME/KEY: CDS
<222> LOCATION: (438)..(3134)

<400> SEQUENCE: 47
gtcctcgacc agtttgtacg gctgcgggat ggtgaccgct actggtttga gaacaccagg      60
aatgggctgt tctccaagaa ggagattgag acatccgaaa taccaccgtg cgggacgtgc     120
tggtcgctgt tatcaacatt gaccccagtg ccctgcagcc caatgtcttt gtctggcata     180
aaggtgcacc ctgccctcaa cctaagcagc tcacaactga cggcctgccc cagtgtgcac     240
ccctgactgt gcttgacttc tttgaaggca gcagccctgg ttttgccatc accatcattg     300
ctctctgctg ccttccctta gtgagtctgc ttctctctgg agtggtggcc tatttccggg     360
gccgagaaca caagaagcta caaaagaaac tcaaagagag cgtgaagaag gaagcagcca     420
aagatggagt gccagcg atg gag tgg cca ggc ccc aag gag agg agc agt         470
                   Met Glu Trp Pro Gly Pro Lys Glu Arg Ser Ser
                     1               5                  10 ccc atc atc atc cag ctg ctg tca gac agg tgt ctg cag gtc ctg aac       518
Pro Ile Ile Ile Gln Leu Leu Ser Asp Arg Cys Leu Gln Val Leu Asn
            15                  20                  25 agg cat ctc act gtg ctc cgt gtg gtc cag ctg cag cct ctg cag cag       566
Arg His Leu Thr Val Leu Arg Val Val Gln Leu Gln Pro Leu Gln Gln
        30                  35                  40 gtc aac ctc atc ctg tcc aac aac cga gga tgc cgc acc ctg ctg ctc       614
Val Asn Leu Ile Leu Ser Asn Asn Arg Gly Cys Arg Thr Leu Leu Leu
    45                  50                  55 aag atc cct aag gag tat gac ctg gtg ctg ctg ttt agt tct gaa gag       662
Lys Ile Pro Lys Glu Tyr Asp Leu Val Leu Leu Phe Ser Ser Glu Glu
 60                  65                  70                  75 gaa cgg ggc gcc ttt gtg cag cag cta tgg gac ttc tgc gtg cgc tgg       710
Glu Arg Gly Ala Phe Val Gln Gln Leu Trp Asp Phe Cys Val Arg Trp
                80                  85                  90 gct ctg ggc ctc cat gtg gct gag atg agc gag aag gag cta ttt agg       758
Ala Leu Gly Leu His Val Ala Glu Met Ser Glu Lys Glu Leu Phe Arg
            95                 100                 105 aag gct gtg aca aag cag cag cgg gaa cgc atc ctg gag atc ttc ttc       806
Lys Ala Val Thr Lys Gln Gln Arg Glu Arg Ile Leu Glu Ile Phe Phe
        110                 115                 120 aga cac ctt ttt gct cag gtg ctg gac atc aac cag gcc gac gca ggg       854
Arg His Leu Phe Ala Gln Val Leu Asp Ile Asn Gln Ala Asp Ala Gly
    125                 130                 135 acc ctg ccc ctg gac tcc tcc cag aag gtg cgg gag gcc ctg acc tgc       902
Thr Leu Pro Leu Asp Ser Ser Gln Lys Val Arg Glu Ala Leu Thr Cys
140                 145                 150                 155
```

-continued

| | |
|---|---|
| gag ctg agc agg gcc gag ttt gcc gag tcc ctg ggc ctc aag ccc cag<br>Glu Leu Ser Arg Ala Glu Phe Ala Glu Ser Leu Gly Leu Lys Pro Gln<br>          160                    165                  170 | 950 |
| gac atg ttt gtg gag tcc atg ttc tct ctg gct gac aag gat ggc aat<br>Asp Met Phe Val Glu Ser Met Phe Ser Leu Ala Asp Lys Asp Gly Asn<br>    175                      180                    185 | 998 |
| ggc tac ctg tcc ttc cga gag ttc ctg gac atc ctg gtg gtc ttc atg<br>Gly Tyr Leu Ser Phe Arg Glu Phe Leu Asp Ile Leu Val Val Phe Met<br>         190                    195                200 | 1046 |
| aaa ggc tcc cca gag gat aag tcc cgt cta atg ttt acc atg tat gac<br>Lys Gly Ser Pro Glu Asp Lys Ser Arg Leu Met Phe Thr Met Tyr Asp<br>205                    210                    215 | 1094 |
| ctg gat gag aat ggc ttc ctc tcc aag gac gaa ttc ttc acc atg atg<br>Leu Asp Glu Asn Gly Phe Leu Ser Lys Asp Glu Phe Phe Thr Met Met<br>220                    225                    230                    235 | 1142 |
| cga tcc ttc atc gag atc tcc aac aac tgc ctg tcc aag gcc cag ctg<br>Arg Ser Phe Ile Glu Ile Ser Asn Asn Cys Leu Ser Lys Ala Gln Leu<br>         240                    245                250 | 1190 |
| gcc gag gtg gtg gag tct atg ttc cgg gag tcg gga ttc cag gac aag<br>Ala Glu Val Val Glu Ser Met Phe Arg Glu Ser Gly Phe Gln Asp Lys<br>         255                    260                265 | 1238 |
| gag gag ctg aca tgg gag gat ttt cac ttc atg ctg cgg gac cat gac<br>Glu Glu Leu Thr Trp Glu Asp Phe His Phe Met Leu Arg Asp His Asp<br>    270                      275                    280 | 1286 |
| agc gag ctc cgc ttc acg cag ctc tgt gtc aaa ggt gga ggt gga ggt<br>Ser Glu Leu Arg Phe Thr Gln Leu Cys Val Lys Gly Gly Gly Gly Gly<br>285                    290                    295 | 1334 |
| gga aat ggt att aga gat atc ttt aaa caa aac atc agc tgt cga gtc<br>Gly Asn Gly Ile Arg Asp Ile Phe Lys Gln Asn Ile Ser Cys Arg Val<br>300                    305                    310                    315 | 1382 |
| tcg ttc atc act cgg aca cct ggg gag cgc tcc cac ccc cag gga ctg<br>Ser Phe Ile Thr Arg Thr Pro Gly Glu Arg Ser His Pro Gln Gly Leu<br>                  320                    325                330 | 1430 |
| ggg ccc cct gtc cca gaa gcc cca gag ctg gga ggc cct gga ctg aag<br>Gly Pro Pro Val Pro Glu Ala Pro Glu Leu Gly Gly Pro Gly Leu Lys<br>         335                    340                345 | 1478 |
| aag agg ttt ggc aaa aag gca gca gtg ccc act ccc cgg ctg tac aca<br>Lys Arg Phe Gly Lys Lys Ala Ala Val Pro Thr Pro Arg Leu Tyr Thr<br>    350                      355                    360 | 1526 |
| gag gcg ctg caa gag aag atg cag cga ggc ttc cta gcc caa aag ctg<br>Glu Ala Leu Gln Glu Lys Met Gln Arg Gly Phe Leu Ala Gln Lys Leu<br>365                    370                    375 | 1574 |
| cag cag tac aag cgc ttc gtg gag aac tac cgg agg cac atc gtg tgt<br>Gln Gln Tyr Lys Arg Phe Val Glu Asn Tyr Arg Arg His Ile Val Cys<br>380                    385                    390                    395 | 1622 |
| gtg gca atc ttc tcg gcc atc tgt gtt ggc gtg ttt gca gat cgt gct<br>Val Ala Ile Phe Ser Ala Ile Cys Val Gly Val Phe Ala Asp Arg Ala<br>                  400                    405                410 | 1670 |
| tac tac tat ggc ttt gcc ttg cca ccc tcg gac att gca cag acc acc<br>Tyr Tyr Tyr Gly Phe Ala Leu Pro Pro Ser Asp Ile Ala Gln Thr Thr<br>         415                    420                425 | 1718 |
| ctc gtg ggc atc atc ctg tca cga ggc acg gcg gcc agc gtc tcc ttc<br>Leu Val Gly Ile Ile Leu Ser Arg Gly Thr Ala Ala Ser Val Ser Phe<br>    430                      435                    440 | 1766 |
| atg ttc tct tat atc ttg ctc acc atg tgc cgc aac ctc ata acc ttc<br>Met Phe Ser Tyr Ile Leu Leu Thr Met Cys Arg Asn Leu Ile Thr Phe<br>445                    450                    455 | 1814 |
| ctg cga gag act ttc ctc aac cgc tat gtg cct ttt gat gcc gca gtg<br>Leu Arg Glu Thr Phe Leu Asn Arg Tyr Val Pro Phe Asp Ala Ala Val | 1862 |

```
          460                 465                 470                 475
gac ttc cac cgc tgg atc gcc atg gct gct gtt gtc ctg gcc att ttg              1910
Asp Phe His Arg Trp Ile Ala Met Ala Ala Val Val Leu Ala Ile Leu
                    480                 485                 490 cac agt gct ggc cac gca gtc aat gtc tac atc ttc tca gtc agc cca              1958
His Ser Ala Gly His Ala Val Asn Val Tyr Ile Phe Ser Val Ser Pro
                495                 500                 505 ctc agc ctg ctg gcc tgc ata ttc ccc aac gtc ttt gtg aat gat ggg              2006
Leu Ser Leu Leu Ala Cys Ile Phe Pro Asn Val Phe Val Asn Asp Gly
            510                 515                 520 tcc aag ctt ccc cag aag ttc tat tgg tgg ttc ttc cag acc gtc cca              2054
Ser Lys Leu Pro Gln Lys Phe Tyr Trp Trp Phe Phe Gln Thr Val Pro
        525                 530                 535 ggt atg aca ggt gtg ctt ctg ctc ctg gtc ctg gcc atc atg tat gtc              2102
Gly Met Thr Gly Val Leu Leu Leu Leu Val Leu Ala Ile Met Tyr Val
540                 545                 550                 555 ttc gcc tcc cac cac ttc cgc cgc cgc agc ttc cgg ggc ttc tgg ctg              2150
Phe Ala Ser His His Phe Arg Arg Arg Ser Phe Arg Gly Phe Trp Leu
                    560                 565                 570 acc cac cac ctc tac atc ctg ctc tat gcc ctg ctc atc atc cat ggc              2198
Thr His His Leu Tyr Ile Leu Leu Tyr Ala Leu Leu Ile Ile His Gly
                575                 580                 585 agc tat gct ctg atc cag ctg ccc act ttc cac atc tac ttc ctg gtc              2246
Ser Tyr Ala Leu Ile Gln Leu Pro Thr Phe His Ile Tyr Phe Leu Val
            590                 595                 600 ccg gca atc atc tat gga ggt gac aag ctg gtg agc ctg agc cgg aag              2294
Pro Ala Ile Ile Tyr Gly Gly Asp Lys Leu Val Ser Leu Ser Arg Lys
        605                 610                 615 aag gtg gag atc agc gtg gtg aag gcg gag ctg ctg ccc tca gga gtg              2342
Lys Val Glu Ile Ser Val Val Lys Ala Glu Leu Leu Pro Ser Gly Val
620                 625                 630                 635 acc tac ctg caa ttc cag agg ccc caa ggc ttt gag tac aag tca gga              2390
Thr Tyr Leu Gln Phe Gln Arg Pro Gln Gly Phe Glu Tyr Lys Ser Gly
                    640                 645                 650 cag tgg gtg cgg atc gcc tgc ctg gct ctg ggg acc acc gag tac cac              2438
Gln Trp Val Arg Ile Ala Cys Leu Ala Leu Gly Thr Thr Glu Tyr His
                655                 660                 665 ccc ttc aca ctg acc tcc gcg ccc cat gag gac aca ctc agc ctg cac              2486
Pro Phe Thr Leu Thr Ser Ala Pro His Glu Asp Thr Leu Ser Leu His
            670                 675                 680 atc cgg gca gtg ggg ccc tgg acc act cgc ctc agg gag atc tac tca              2534
Ile Arg Ala Val Gly Pro Trp Thr Thr Arg Leu Arg Glu Ile Tyr Ser
        685                 690                 695 tcc cca aag ggc aat ggc tgt gct gga tac cca aag ctg tac ctt gat              2582
Ser Pro Lys Gly Asn Gly Cys Ala Gly Tyr Pro Lys Leu Tyr Leu Asp
700                 705                 710                 715 gga ccg ttt gga gag ggc cat cag gag tgg cat aaa ttt gag gtg tca              2630
Gly Pro Phe Gly Glu Gly His Gln Glu Trp His Lys Phe Glu Val Ser
                    720                 725                 730 gtg ttg gtg gga ggg ggc att ggg gtc acc ccc ttt gcc tcc atc ctc              2678
Val Leu Val Gly Gly Gly Ile Gly Val Thr Pro Phe Ala Ser Ile Leu
                735                 740                 745 aaa gac ctg gtc ttc aag tca tcc ttg ggc agc caa atg ctg tgt aag              2726
Lys Asp Leu Val Phe Lys Ser Ser Leu Gly Ser Gln Met Leu Cys Lys
            750                 755                 760 aag atc tac ttc atc tgg gtg aca cgg acc cag cgt cag ttt gag tgg              2774
Lys Ile Tyr Phe Ile Trp Val Thr Arg Thr Gln Arg Gln Phe Glu Trp
        765                 770                 775 ctg gct gac atc atc caa gag gtg gag gag aac gac cac cag gac ctg              2822
Leu Ala Asp Ile Ile Gln Glu Val Glu Glu Asn Asp His Gln Asp Leu
```

| | |
|---|---|
| Leu Ala Asp Ile Ile Gln Glu Val Glu Glu Asn Asp His Gln Asp Leu<br>780                               785                       790                   795 | |
| gtg tct gtg cac att tat gtc acc cag ctg gct gag aag ttc gac ctc<br>Val Ser Val His Ile Tyr Val Thr Gln Leu Ala Glu Lys Phe Asp Leu<br>                       800                     805                     810 | 2870 |
| agg acc acc atg cta tac atc tgc gag cgg cac ttc cag aaa gtg ctg<br>Arg Thr Thr Met Leu Tyr Ile Cys Glu Arg His Phe Gln Lys Val Leu<br>               815                     820                   825 | 2918 |
| aac cgg agt ctg ttc acg ggc ctg cgc tcc atc acc cac ttt ggc cgt<br>Asn Arg Ser Leu Phe Thr Gly Leu Arg Ser Ile Thr His Phe Gly Arg<br>         830                     835                   840 | 2966 |
| ccc ccc ttc gag ccc ttc ttc aac tcc ctg cag gag gtc cac cca cag<br>Pro Pro Phe Glu Pro Phe Phe Asn Ser Leu Gln Glu Val His Pro Gln<br>845                               850                       855 | 3014 |
| gtg cgc aag atc ggg gtg ttc agc tgc ggc cct cca gga atg acc aag<br>Val Arg Lys Ile Gly Val Phe Ser Cys Gly Pro Pro Gly Met Thr Lys<br>860                               865                     870                   875 | 3062 |
| aat gta gag aag gcc tgt cag ctc gtc aac agg cag gac cga gcc cac<br>Asn Val Glu Lys Ala Cys Gln Leu Val Asn Arg Gln Asp Arg Ala His<br>                       880                     885                   890 | 3110 |
| ttc atg cac cac tat gag aac ttc tgagcctgtc ctccctggct gctgcttcca<br>Phe Met His His Tyr Glu Asn Phe<br>                   895 | 3164 |
| gtatcctgcc ttctcttctg tgcacctaag ttgcccagcc ctgctggcaa tctctccatc | 3224 |
| agaatccacc ttaggcctca gctggagggc tgcagagccc ctcccaatat tgggagaata | 3284 |
| ttgacccaga caattataca aatgagaaaa ggcattaaaa tttacgtttc tgatgatggc | 3344 |
| aaagctcatt tttctattag taactctgct gaagatccat ttattgcaat tcatgctgaa | 3404 |
| tctaaattgt aaaatttaaa attaaatgca tgtcctcaaa aaaaaaaa | 3453 |

<210> SEQ ID NO 48
<211> LENGTH: 899
<212> TYPE: PRT
<213> ORGANISM: Homo sapiens

<400> SEQUENCE: 48

Met Glu Trp Pro Gly Pro Lys Glu Arg Ser Ser Pro Ile Ile Ile Gln
1               5                   10                  15

Leu Leu Ser Asp Arg Cys Leu Gln Val Leu Asn Arg His Leu Thr Val
            20                  25                  30

Leu Arg Val Val Gln Leu Gln Pro Leu Gln Gln Val Asn Leu Ile Leu
        35                  40                  45

Ser Asn Asn Arg Gly Cys Arg Thr Leu Leu Leu Lys Ile Pro Lys Glu
    50                  55                  60

Tyr Asp Leu Val Leu Leu Phe Ser Ser Glu Glu Arg Gly Ala Phe
65                  70                  75                  80

Val Gln Gln Leu Trp Asp Phe Cys Val Arg Trp Ala Leu Gly Leu His
                85                  90                  95

Val Ala Glu Met Ser Glu Lys Glu Leu Phe Arg Lys Ala Val Thr Lys
            100                 105                 110

Gln Gln Arg Glu Arg Ile Leu Glu Ile Phe Phe Arg His Leu Phe Ala
        115                 120                 125

Gln Val Leu Asp Ile Asn Gln Ala Asp Ala Gly Thr Leu Pro Leu Asp
    130                 135                 140

Ser Ser Gln Lys Val Arg Glu Ala Leu Thr Cys Glu Leu Ser Arg Ala
145                 150                 155                 160

-continued

```
Glu Phe Ala Glu Ser Leu Gly Leu Lys Pro Gln Asp Met Phe Val Glu
            165                 170                 175

Ser Met Phe Ser Leu Ala Asp Lys Asp Gly Asn Gly Tyr Leu Ser Phe
        180                 185                 190

Arg Glu Phe Leu Asp Ile Leu Val Val Phe Met Lys Gly Ser Pro Glu
        195                 200                 205

Asp Lys Ser Arg Leu Met Phe Thr Met Tyr Asp Leu Asp Glu Asn Gly
    210                 215                 220

Phe Leu Ser Lys Asp Glu Phe Thr Met Met Arg Ser Phe Ile Glu
225                 230                 235                 240

Ile Ser Asn Asn Cys Leu Ser Lys Ala Gln Leu Ala Glu Val Val Glu
                245                 250                 255

Ser Met Phe Arg Glu Ser Gly Phe Gln Asp Lys Glu Glu Leu Thr Trp
        260                 265                 270

Glu Asp Phe His Phe Met Leu Arg Asp His Asp Ser Glu Leu Arg Phe
    275                 280                 285

Thr Gln Leu Cys Val Lys Gly Gly Gly Gly Gly Asn Gly Ile Arg
    290                 295                 300

Asp Ile Phe Lys Gln Asn Ile Ser Cys Arg Val Ser Phe Ile Thr Arg
305                 310                 315                 320

Thr Pro Gly Glu Arg Ser His Pro Gln Gly Leu Gly Pro Pro Val Pro
                325                 330                 335

Glu Ala Pro Glu Leu Gly Gly Pro Gly Leu Lys Lys Arg Phe Gly Lys
            340                 345                 350

Lys Ala Ala Val Pro Thr Pro Arg Leu Tyr Thr Glu Ala Leu Gln Glu
        355                 360                 365

Lys Met Gln Arg Gly Phe Leu Ala Gln Lys Leu Gln Gln Tyr Lys Arg
    370                 375                 380

Phe Val Glu Asn Tyr Arg Arg His Ile Val Cys Val Ala Ile Phe Ser
385                 390                 395                 400

Ala Ile Cys Val Gly Val Phe Ala Asp Arg Ala Tyr Tyr Gly Phe
                405                 410                 415

Ala Leu Pro Pro Ser Asp Ile Ala Gln Thr Thr Leu Val Gly Ile Ile
            420                 425                 430

Leu Ser Arg Gly Thr Ala Ala Ser Val Ser Phe Met Phe Ser Tyr Ile
        435                 440                 445

Leu Leu Thr Met Cys Arg Asn Leu Ile Thr Phe Leu Arg Glu Thr Phe
    450                 455                 460

Leu Asn Arg Tyr Val Pro Phe Asp Ala Ala Val Asp Phe His Arg Trp
465                 470                 475                 480

Ile Ala Met Ala Ala Val Val Leu Ala Ile Leu His Ser Ala Gly His
                485                 490                 495

Ala Val Asn Val Tyr Ile Phe Ser Val Ser Pro Leu Ser Leu Leu Ala
            500                 505                 510

Cys Ile Phe Pro Asn Val Phe Asn Asp Gly Ser Lys Leu Pro Gln
    515                 520                 525

Lys Phe Tyr Trp Trp Phe Gln Thr Val Pro Gly Met Thr Gly Val
    530                 535                 540

Leu Leu Leu Leu Val Leu Ala Ile Met Tyr Val Phe Ala Ser His His
545                 550                 555                 560

Phe Arg Arg Arg Ser Phe Arg Gly Phe Trp Leu Thr His His Leu Tyr
            565                 570                 575

Ile Leu Leu Tyr Ala Leu Leu Ile Ile His Gly Ser Tyr Ala Leu Ile
```

```
                    580                585                590
Gln Leu Pro Thr Phe His Ile Tyr Phe Leu Val Pro Ala Ile Ile Tyr
            595                600                605
Gly Gly Asp Lys Leu Val Ser Leu Ser Arg Lys Lys Val Glu Ile Ser
610                615                620
Val Val Lys Ala Glu Leu Leu Pro Ser Gly Val Thr Tyr Leu Gln Phe
625                630                635                640
Gln Arg Pro Gln Gly Phe Glu Tyr Lys Ser Gly Gln Trp Val Arg Ile
                645                650                655
Ala Cys Leu Ala Leu Gly Thr Thr Glu Tyr His Pro Phe Thr Leu Thr
            660                665                670
Ser Ala Pro His Glu Asp Thr Leu Ser Leu His Ile Arg Ala Val Gly
            675                680                685
Pro Trp Thr Thr Arg Leu Arg Glu Ile Tyr Ser Ser Pro Lys Gly Asn
            690                695                700
Gly Cys Ala Gly Tyr Pro Lys Leu Tyr Leu Asp Gly Pro Phe Gly Glu
705                710                715                720
Gly His Gln Glu Trp His Lys Phe Glu Val Ser Val Leu Val Gly Gly
                725                730                735
Gly Ile Gly Val Thr Pro Phe Ala Ser Ile Leu Lys Asp Leu Val Phe
            740                745                750
Lys Ser Ser Leu Gly Ser Gln Met Leu Cys Lys Lys Ile Tyr Phe Ile
            755                760                765
Trp Val Thr Arg Thr Gln Arg Gln Phe Glu Trp Leu Ala Asp Ile Ile
            770                775                780
Gln Glu Val Glu Glu Asn Asp His Gln Asp Leu Val Ser Val His Ile
785                790                795                800
Tyr Val Thr Gln Leu Ala Glu Lys Phe Asp Leu Arg Thr Thr Met Leu
                805                810                815
Tyr Ile Cys Glu Arg His Phe Gln Lys Val Leu Asn Arg Ser Leu Phe
            820                825                830
Thr Gly Leu Arg Ser Ile Thr His Phe Gly Arg Pro Pro Phe Glu Pro
            835                840                845
Phe Phe Asn Ser Leu Gln Glu Val His Pro Gln Val Arg Lys Ile Gly
            850                855                860
Val Phe Ser Cys Gly Pro Pro Gly Met Thr Lys Asn Val Glu Lys Ala
865                870                875                880
Cys Gln Leu Val Asn Arg Gln Asp Arg Ala His Phe Met His His Tyr
                885                890                895
Glu Asn Phe
```

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 49
cctgacagat gtatttcact acccag                                    26

<210> SEQ ID NO 50
<211> LENGTH: 24
<212> TYPE: DNA
<213> ORGANISM: Artificial Sequence
<220> FEATURE:

```
<223> OTHER INFORMATION: Description of Artificial Sequence:  Primer

<400> SEQUENCE: 50
ggatcggagt cactcccttc gctg                                              24

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence:  Primer

<400> SEQUENCE: 51
ctagaagctc tccttgttgt aataga                                            26

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 52
atgaacacct ctggggtcag ctga                                              24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 53
atgaacacct ctggggtcag ctga                                              24

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence:  Primer

<400> SEQUENCE: 54
gtcctctgca gcattgttcc tctta                                             25

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence:  Primer

<400> SEQUENCE: 55
cctgacagat gtatttcact acccag                                            26

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 56
ggatcggagt cactcccttc gctg                                              24
```

-continued

```
<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence:  Primer

<400> SEQUENCE: 57
aatgacactg tactggaggc cacag                                          25

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 58
ctgccatcta ccacacggat ctgc                                           24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 59
cttgccattc caaagcttcc atgc                                           24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 60
gtacaagtca ggacagtggg tgcg                                           24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:  Primer

<400> SEQUENCE: 61
tggatgatgt cagccagcca ctca                                           24
```

MITOGENIC OXYGENASES

CROSS REFERENCE TO RELATED APPLICATIONS

This application is a continuation of U.S. patent application Ser. No. 09/437,568, filed Nov. 10, 1999 now U.S. Pat. No. 6,620,603 which claims the benefit of U.S. Provisional Patent Application Ser. No. 60/107,911, filed Nov. 10, 1998, U.S. Provisional Patent Application Ser. No. 60/149,332, filed Aug. 17, 1999, and U.S. Provisional Patent Application Ser. No. 60/151,242, filed Aug. 27, 1999. Each of the aforementioned patent applications is hereby incorporated by reference in its entirety.

The U.S. Government has a paid-up license in this invention and the right in limited circumstances to require the patent owner to license others on reasonable terms as provided for by the terms of National Institutes of Health grants HL38206 and HL58000.

TECHNICAL FIELD

The present invention relates to the field of normal and abnormal cell growth, in particular mitogenic regulation. The present invention provides the following: nucleotide sequences encoding for the production of enzymes that are mitogenic regulators; amino acid sequences of these enzymes; vectors containing these nucleotide sequences; methods for transfecting cells with vectors that produce these enzymes; transfected cells; methods for administering these transfected cells to animals to induce tumor formation; and antibodies to these enzymes that are useful for detecting and measuring levels of these enzymes, and for binding to cells possessing extracellular epitopes of these enzymes.

BACKGROUND OF THE INVENTION

Reactive oxygen intermediates (ROI) are partial reduction products of oxygen: 1 electron reduces $O_2$ to form superoxide ($O_2^-$), and 2 electrons reduce $O_2$ to form hydrogen peroxide ($H_2O_2$). ROI are generated as a byproduct of aerobic metabolism and by toxicological mechanisms. There is growing evidence for regulated enzymatic generation of $O_2^-$ and its conversion to $H_2O_2$ in a variety of cells. The conversion of $O_2^-$ to $H_2O_2$ occurs spontaneously, but is markedly accelerated by superoxide dismutase (SOD). High levels of ROI are associated with damage to biomolecules such as DNA, biomembranes and proteins. Recent evidence indicates generation of ROI under normal cellular conditions and points to signaling roles for $O_2^-$ and $H_2O_2$.

Several biological systems generate reactive oxygen. Phagocytic cells such as neutrophils generate large quantities of ROI as part of their battery of bactericidal mechanisms. Exposure of neutrophils to bacteria or to various soluble mediators such as formyl-Met-Leu-Phe or phorbol esters activates a massive consumption of oxygen, termed the respiratory burst, to initially generate superoxide, with secondary generation of $H_2O_2$, HOCl and hydroxyl radical. The enzyme responsible for this oxygen consumption is the respiratory burst oxidase (nicotinamide adenine dinucleotide phosphate-reduced form (NADPH) oxidase).

There is growing evidence for the generation of ROI by non-phagocytic cells, particularly in situations related to cell proliferation. Significant generation of $H_2O_2$, $O_2^-$, or both have been noted in some cell types. Fibroblasts and human endothelial cells show increased release of superoxide in response to cytokines such as interleukin-1 or tumor necrosis factor (TNF) (Meier et al. (1989) Biochem J. 263, 539–545.; Matsubara et al. (1986) J. Immun. 137, 3295–3298). Ras-transformed fibroblasts show increased superoxide release compared with control fibroblasts (Irani, et al. (1997) Science 275, 1649–1652). Rat vascular smooth muscle cells show increased $H_2O_2$ release in response to PDGF (Sundaresan et al. (1995) Science 270, 296–299) and angiotensin II (Griendling et al. (1994) Circ. Res. 74, 1141–1148; Fukui et al. (1997) Circ. Res. 80, 45–51; Ushio-Fukai et al. (1996) J. Biol. Chem. 271, 23317–23321), and $H_2O_2$ in these cells is associated with increased proliferation rate. The occurrence of ROI in a variety of cell types is summarized in Table 1 (adapted from Burdon, R. (1995) Free Radical Biol. Med. 18, 775–794).

TABLE 1

| Superoxide | Hydrogen Peroxide |
|---|---|
| human fibroblasts | Balb/3T3 cells |
| human endothelial cells | rat pancreatic islet cells |
| human/rat smooth muscle cells | murine keratinocytes |
| human fat cells | rabbit chondrocytes |
| human osteocytes | human tumor cells |
| BHK-21 cells | fat cells, 3T3 L1 cells |
| human colonic epithelial cells | |

ROI generated by the neutrophil have a cytotoxic function. While ROI are normally directed at the invading microbe, ROI can also induce tissue damage (e.g., in inflammatory conditions such as arthritis, shock, lung disease, and inflammatory bowel disease) or may be involved in tumor initiation or promotion, due to damaging effects on DNA. Nathan (Szatrowski et al. (1991) Canc. Res. 51, 794–798) proposed that the generation of ROI in tumor cells may contribute to the hypermutability seen in tumors, and may therefore contribute to tumor heterogeneity, invasion and metastasis.

In addition to cytotoxic and mutagenic roles, ROI have ideal properties as signal molecules: 1) they are generated in a controlled manner in response to upstream signals; 2) the signal can be terminated by rapid metabolism of $O_2^-$ and $H_2O_2$ by SOD and catalase/peroxidases; 3) they elicit downstream effects on target molecules, e.g., redox-sensitive regulatory proteins such as NF kappa B and AP-1 (Schreck et al. (1991) EMBO J. 10, 2247–2258; Schmidt et al. (1995) Chemistry & Biology 2, 13–22). Oxidants such as $O_2^-$ and $H_2O_2$ have a relatively well defined signaling role in bacteria, operating via the SoxI/II regulon to regulate transcription.

ROI appear to have a direct role in regulating cell division, and may function as mitogenic signals in pathological conditions related to growth. These conditions include cancer and cardiovascular disease. $O_2^-$ is generated in endothelial cells in response to cytokines, and might play a role in angiogenesis (Matsubara et al. (1986) J. Immun. 137, 3295–3298). $O_2^-$ and $H_2O_2$ are also proposed to function as "life-signals", preventing cells from undergoing apoptosis (Matsubara et al. (1986) J. Immun. 137, 3295–3298). As discussed above, many cells respond to growth factors (e.g., platelet derived growth factor (PDGF), epidermal derived growth factor (EGF), angiotensin II, and various cytokines) with both increased production of $O_2^-/H_2O_2$ and increased proliferation. Inhibition of ROI generation prevents the mitogenic response. Exposure to exogenously generated.

$O_2^-$ and $H_2O_2$ results in an increase in cell proliferation. A partial list of responsive cell types is shown below in Table 2 (adapted from Burdon, R. (1995) *Free Radical Biol. Med.* 18, 775–794).

TABLE 2

| Superoxide | Hydrogen peroxide |
| --- | --- |
| human, hamster fibroblasts | mouse osteoblastic cells |
| Balb/3T3 cells | Balb/3T3 cells |
| human histiocytic leukemia | rat, hamster fibroblasts |
| mouse epidermal cells | human smooth muscle cells |
| rat colonic epithelial cells | rat vascular smooth muscle |
| rat vascular smooth muscle cells | |

While non-transformed cells can respond to growth factors and cytokines with the production of ROI, tumor cells appear to produce ROI in an uncontrolled manner. A series of human tumor cells produced large amounts of hydrogen peroxide compared with non-tumor cells (Szatrowski et al. (1991) *Canc. Res.* 51, 794–798). Ras-transformed NIH 3T3 cells generated elevated amounts of superoxide, and inhibition of superoxide generation by several mechanisms resulted in a reversion to a "normal" growth phenotype.

$O_2^-$ has been implicated in maintenance of the transformed phenotype in cancer cells including melanoma, breast carcinoma, fibrosarcoma, and virally transformed tumor cells. Decreased levels of the manganese form of SOD (MnSOD) have been measured in cancer cells and in vitro-transformed cell lines, predicting increased $O_2^-$ levels (Burdon, R. (1995) *Free Radical Biol. Med.* 18, 775–794). MnSOD is encoded on chromosome 6q25 which is very often lost in melanoma. Overexpression of MnSOD in melanoma and other cancer cells (Church et al. (1993) *Proc. of Natl. Acad. Sci.* 90, 3113–3117; Fernandez-Pol et al. (1982) *Canc. Res.* 42, 609–617; Yan et al. (1996) *Canc. Res.* 56, 2864–2871) resulted in suppression of the transformed phenotype.

ROI are implicated in growth of vascular smooth muscle associated with hypertension, atherosclerosis, and restenosis after angioplasty. $O_2^-$ generation is seen in rabbit aortic adventitia (Pagano et al. (1997) *Proc. Natl. Acad. Sci.* 94, 14483–14488). Vascular endothelial cells release $O_2^-$ in response to cytokines (Matsubara et al. (1986) *J. Immun.* 137, 3295–3298). $O_2^-$ is generated by aortic smooth muscle cells in culture, and increased $O_2^-$ generation is stimulated by angiotensin II which also induces cell hypertrophy. In a rat model system, infusion of angiotensin II leads to hypertension as well as increased $O_2^-$ generation in subsequently isolated aortic tissue (Ushio-Fukai et al. (1996) *J. Biol. Chem.* 271, 23317–23321.; Yu et al. (1997) *J. Biol. Chem.* 272, 27288–27294). Intravenous infusion of a form of SOD that localizes to the vasculature or an infusion of an $O_2^-$ scavenger prevented angiotensin II induced hypertension and inhibited ROI generation (Fukui et al. (1997) *Circ. Res.* 80, 45–51).

The neutrophil NADPH oxidase, also known as phagocyte respiratory burst oxidase, provides a paradigm for the study of the specialized enzymatic ROI-generating system. This extensively studied enzyme oxidizes NADPH and reduces oxygen to form $O_2^-$. NADPH oxidase consists of multiple proteins and is regulated by assembly of cytosolic and membrane components. The catalytic moiety consists of flavocytochrome $b_{558}$, an integral plasma membrane enzyme comprised of two components: gp91phox (gp refers to glycoprotein; phox is an abbreviation of the words phagocyte and oxidase) and p22phox (p refers to protein). gp91phox contains 1 flavin adenine dinucleotide (FAD) and 2 hemes as well as the NADPH binding site. p22phox has a C-terminal proline-rich sequence which serves as a binding site for cytosolic regulatory proteins. The two cytochrome subunits, gp91phox and p22phox appear to stabilize one another, since the genetic absence of either subunit, as in the inherited disorder chronic granulomatous disease (CGD), results in the absence of the partner subunit (Yu et al. (1997) *J. Biol. Chem.* 272, 27288–27294). Essential cytosolic proteins include p47phox, p67phox and the small GTPase Rac, of which there are two isoforms. p47phox and p67phox both contain $SH_3$ regions and proline-rich regions which participate in protein interactions governing assembly of the oxidase components during activation. The neutrophil enzyme is regulated in response to bacterial phagocytosis or chemotactic signals by phosphorylation of p47phox, and perhaps other components, as well as by guanine nucleotide exchange to activate the GTP-binding protein Rac.

The origin of ROI in non-phagocytic tissues is unproven, but the occurrence of phagocyte oxidase components has been evaluated in several systems by immunochemical methods, Northern blots and reverse transcriptase-polymerase chain reaction (RT-PCR). The message for p22phox is expressed widely, as is that for Rac1. Several cell types that are capable of $O_2^-$ generation have been demonstrated to contain all of the phox components including gp91phox, as summarized below in Table 3. These cell types include endothelial cells, aortic adventitia and lymphocytes.

TABLE 3

| Tissue | gp91phox | p22phox | p47phox | p67phox |
| --- | --- | --- | --- | --- |
| neutrophil | $+^{1,2}$ | $+^{1,2}$ | $+^{1,2}$ | $+^{1,2}$ |
| aortic adventitia | $+^1$ | $+^1$ | $+^1$ | $+^1$ |
| lymphocytes | $+^2$ | $+^2$ | $+^{1,2}$ | $+^{1,2}$ |
| endothelial cells | $+^2$ | $+^2$ | $+^{1,2}$ | $+^{1,2}$ |
| glomerular mesangial cells | — | $+^{1,2}$ | $+^{1,2}$ | $+^{1,2}$ |
| fibroblasts | — | $+^2$ | $+^{1,2}$ | $+^2$ |
| aortic sm. muscle | — | $+^{1,2}$ | ? | ? |

[1] = protein expression shown.
[2] = mRNA expression shown.

However, a distinctly different pattern is seen in several other cell types shown in Table 3 including glomerular mesangial cells, rat aortic smooth muscle and fibroblasts. In these cells, expression of gp91phox is absent while p22phox and in some cases cytosolic phox components have been demonstrated to be present. Since gp91phox and p22phox stabilize one another in the neutrophil, there has been much speculation that some molecule, possibly related to gp91phox, accounts for ROI generation in glomerular mesangial cells, rat aortic smooth muscle and fibroblasts (Ushio-Fukai et al. (1996) *J. Biol. Chem.* 271, 23317–23321). Investigation of fibroblasts from a patient with a genetic absence of gp91phox provides proof that the gp91phox subunit is not involved in ROI generation in these cells (Emmendorffer et al. (1993) *Eur. J. Haematol.* 51, 223–227). Depletion of p22phox from vascular smooth muscle using an antisense approach indicated that this subunit participates in ROI generation in these cells, despite the absence of detectable gp91phox (Ushio-Fukai et al. (1996) *J. Biol. Chem.* 271, 23317–23321). At this time the molecular candidates possibly related to gp91phox and involved in ROI generation in these cells are unknown.

Accordingly, what is needed is the identity of the proteins involved in ROI generation, especially in non-phagocytic tissues and cells. What is also needed are the nucleotide sequences encoding for these proteins, and the primary sequences of the proteins themselves. Also needed are vectors designed to include nucleotides encoding for these proteins. Probes and PCR primers derived from the nucleotide sequence are needed to detect, localize and measure nucleotide sequences, including mRNA, involved in the synthesis of these proteins. In addition, what is needed is a means to transfect cells with these vectors. What is also needed are expression systems for production of these molecules. Also needed are antibodies directed against these molecules for a variety of uses including localization, detection, measurement and passive immunization.

SUMMARY OF THE INVENTION

The present invention solves the problems described above by providing a novel family of nucleotide sequences and proteins encoded by these nucleotide sequences termed mox proteins and duox proteins. In particular the present invention provides compositions comprising the nucleotide sequences SEQ ID NO:1, SEQ ID NO:3, SEQ ID NO:22, SEQ ID NO:41, SEQ ID NO:45, SEQ ID NO:47, and fragments thereof, which encode for the expression of proteins comprising SEQ ID NO:2, SEQ ID NO:4, SEQ ID NO:21, SEQ ID NO:42, SEQ ID NO:46, SEQ ID NO:48, respectively, and fragments thereof. While not wanting to be bound by the following statement, it is believed that these proteins are involved in ROI production. The present invention also provides vectors containing these nucleotide sequences, cells transfected with these vectors which produce the proteins comprising SEQ ID NO:2, SEQ ID NO:4, SEQ ID NO:21, SEQ ID NO:42, SEQ ID NO:46, SEQ ID NO:48, and fragments thereof, and antibodies to these proteins and fragments thereof. The present invention also provides methods for stimulating cellular proliferation by administering vectors encoded for production of the proteins comprising SEQ ID NO:2, SEQ ID NO:4, SEQ ID NO:21, SEQ ID NO:42, SEQ ID NO:46, SEQ ID NO:48 and fragments thereof. The present invention also provides methods for stimulating cellular proliferation by administering the proteins comprising SEQ ID NO:2, SEQ ID NO:4, SEQ ID NO:21, SEQ ID NO:42, SEQ ID NO:46, SEQ ID NO:48 and fragments thereof. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement.

Most particularly, the present invention involves a method for regulation of cell division or cell proliferation by modifying the activity or expression of the proteins described as SEQ ID NO:2, SEQ ID NO:4, SEQ ID NO:21, SEQ ID NO:42, SEQ ID NO:46, SEQ ID NO:48 or fragments thereof. These proteins, in their naturally occurring or expressed forms, are expected to be useful in drug development, for example for screening of chemical and drug libraries by observing inhibition of the activity of these enzymes. Such chemicals and drugs would likely be useful as treatments for cancer, prostatic hypertrophy, benign prostatic hypertrophy, hypertension, atherosclerosis and many other disorders involving abnormal cell growth or proliferation as described below. The entire expressed protein may be useful in these assays. Portions of the molecule which may be targets for inhibition or modification include but are not limited to the binding site for pyridine nucleotides (NADPH or NADH), the flavoprotein domain (approximately the C-terminal 265 amino acids), and/or the binding or catalytic site for flavin adenine dinucleotide (FAD).

The method of the present invention may be used for the development of drugs or other therapies for the treatment of conditions associated with abnormal growth including, but not limited to the following: cancer, psoriasis, prostatic hypertrophy, benign prostatic hypertrophy, cardiovascular disease, proliferation of vessels, including but not limited to blood vessels and lymphatic vessels, arteriovenous malformation, vascular problems associated with the eye, atherosclerosis, hypertension, and restenosis following angioplasty. The enzymes of the present invention are excellent targets for the development of drugs and other agents which may modulate the activity of these enzymes. It is to be understood that modulation of activity may result in enhanced, diminished or absence of enzymatic activity. Modulation of the activity of these enzymes may be useful in treatment of conditions associated with abnormal growth.

Drugs which affect the activity of the enzymes represented in SEQ ID NO:2, SEQ ID NO:4, SEQ ID NO:21, SEQ ID NO:42, SEQ ID NO:46, SEQ ID NO:48, or fragments thereof, may also be combined with other therapeutics in the treatment of specific conditions. For example, these drugs may be combined with angiogenesis inhibitors in the treatment of cancer, with antihypertensives for the treatment of hypertension, and with cholesterol lowering drugs for the treatment of atherosclerosis.

Accordingly, an object of the present invention is to provide nucleotide sequences, or fragments thereof, encoding for the production of proteins, or fragments thereof, that are involved in ROI production.

Another object of the present invention is to provide vectors containing these nucleotide sequences, or fragments thereof.

Yet another object of the present invention is to provide cells transfected with these vectors.

Still another object of the present invention is to administer cells transfected with these vectors to animals and humans.

Another object of the present invention is to provide proteins, or fragments thereof, that are involved in ROI production.

Still another object of the present invention is to provide antibodies, including monoclonal and polyclonal antibodies, or fragments thereof, raised against proteins, or fragments thereof, that are involved in ROI production.

Another object of the present invention is to administer genes containing nucleotide sequences, or fragments thereof, encoding for the production of proteins, or fragments thereof, that are involved in ROI production, to animals and humans and also to cells obtained from animals and humans.

Another object of the present invention is to administer antisense complimentary sequences of genes containing nucleotide sequences, or fragments thereof, encoding for the production of proteins, or fragments thereof, that are involved in ROI production, to animals and humans and also to cells obtained from animals and humans.

Yet another object of the present invention is to provide a method for stimulating or inhibiting cellular proliferation by administering vectors containing nucleotide sequences, or fragments thereof, encoding for the production of proteins, or fragments thereof, that are involved in ROI production, to animals and humans. It is also an object of the present invention to provide a method for stimulating or inhibiting cellular proliferation by administering vectors containing antisense complimentary sequences of nucleotide sequences, or fragments thereof, encoding for the production of proteins, or fragments thereof, that are involved in ROI production, to animals and humans. These methods of stimulating cellular proliferation are useful for a variety of purposes, including but not limited to, developing animal models of tumor formation, stimulating cellular proliferation of blood marrow cells following chemotherapy or radiation, or in cases of anemia.

Still another object of the present invention is to provide antibodies useful in immunotherapy against cancers expressing the proteins represented in SEQ ID NO:2, SEQ ID NO:4, SEQ ID NO:21, SEQ ID NO:42, SEQ ID NO:46, SEQ ID NO:48 or fragments thereof.

Yet another object of the present invention is to provide nucleotide probes useful for the detection, localization and measurement of nucleotide sequences, or fragments thereof, encoding for the production of proteins, or fragments thereof, that are involved in ROI production.

Another object of the present invention is to provide antibodies useful for the detection, localization and measurement of nucleotide sequences, or fragments thereof, encoding for the production of proteins, or fragments thereof, that are involved in ROI production.

Another object of the present invention is to provide kits useful for detection of nucleic acids including the nucleic acids represented in SEQ ID NO:1, SEQ ID NO:3, SEQ ID NO:22, SEQ ID NO:41, SEQ ID NO:45, SEQ ID NO:47, or fragments thereof, that encode for proteins, or fragments thereof, that are involved in ROI production.

Yet another object of the present invention is to provide kits useful for detection and measurement of nucleic acids including the nucleic acids represented in SEQ ID NO:1, SEQ ID NO:3, SEQ ID NO:22, SEQ ID NO:41, SEQ ID NO:45, SEQ ID NO:47, or fragments thereof, that encode for proteins, or fragments thereof, that are involved in ROI production.

Still another object of the present invention is to provide kits useful for the localization of nucleic acids including the nucleic acids represented in SEQ ID NO:1, SEQ ID NO:3, SEQ ID NO:22, SEQ ID NO:41, SEQ ID NO:45, SEQ ID NO:47, or fragments thereof, that encode for proteins, or fragments thereof that are involved in ROI production.

Another object of the present invention is to provide kits useful for detection of proteins, including the proteins represented in SEQ ID NO:2, SEQ ID NO:4, SEQ ID NO:21, SEQ ID NO:42, SEQ ID NO:46, SEQ ID NO:48, or fragments thereof, that are involved in ROI production.

Yet another object of the present invention is to provide kits useful for detection and measurement of proteins, including the proteins represented in SEQ ID NO:2, SEQ ID NO:4, SEQ ID NO:21, SEQ ID NO:42, SEQ ID NO:46, SEQ ID NO:48, or fragments thereof, that are involved in ROI production.

Still another object of the present invention is to provide kits useful for localization of proteins, including the proteins represented in SEQ ID NO:2, SEQ ID NO:4, SEQ ID NO:21, SEQ ID NO:42, SEQ ID NO:46, SEQ ID NO:48, or fragments thereof, that are involved in ROI production.

Yet another object of the present invention is to provides kits useful for the detection, measurement or localization of nucleic acids, or fragments thereof, encoding for proteins, or fragments thereof, that are involved in ROI production, for use in diagnosis and prognosis of abnormal cellular proliferation related to ROI production.

Another object of the present invention is to provides kits useful for the detection, measurement or localization of proteins, or fragments thereof, that are involved in ROI production, for use in diagnosis and prognosis of abnormal cellular proliferation related to ROI production.

These and other objects, features and advantages of the present invention will become apparent after a review of the following detailed description of the disclosed embodiments and the appended drawings.

BRIEF DESCRIPTION OF THE FIGURES

FIG. 1(a–d). Comparison of amino acid sequences of the human mox1 protein (labeled mox1.human, SEQ ID NO:2), rat mox1 protein (labeled mox1.rat, SEQ ID NO:21), human mox2 protein (labeled mox2.human., SEQ ID NO:4) of the present invention to human (gp 91phox/human.pep, SEQ ID NO:12) bovine (gp 91 phox/bovine.pep, SEQ ID NO:37), and murine (gp 91 phox/mouse.pep, SEQ ID NO:38) proteins. Also included are related plant enzyme proteins cytb 558.arabidopsis.pep (SEQ ID NO:39) and cytb558.rice.pep, (SEQ ID NO:40). Enclosed in boxes are similar amino acid residues.

DETAILED DESCRIPTION OF THE INVENTION

Figure 2:
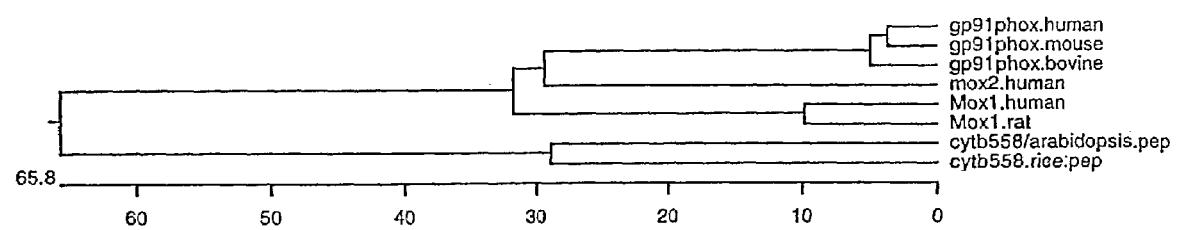
FIG. 2. Sequence similarities among proteins related to gp91phox including human mox1 (SEQ ID NO:2), human mox2 (SEQ ID NO:4), and rat mox1 (SEQ ID NO:21). The dendrogram indicates the degree of similarity among this family of proteins, and also includes the related plant enzymes.

The present invention solves the problems described above by providing a novel family of nucleotide sequences and proteins, encoded by these nucleotide sequences, termed mox proteins and duox proteins. The term "mox" refers to "mitogenic oxidase" while the term "duox" refers to "dual oxidase". In particular, the present invention provides novel compositions comprising the nucleotide sequences SEQ ID NO:1, SEQ ID NO:3, SEQ ID NO:22, SEQ ID NO:41, SEQ ID NO:45, SEQ ID NO:47, and fragments thereof, which encode, respectively, for the expression of proteins comprising NO:42, SEQ ID NO:46, SEQ ID NO:48 and fragments thereof.

Both the mox and duox proteins described herein have homology to the gp91phox protein involved in ROI generation, however, the mox and duox proteins comprise a novel and distinct family of proteins. The mox proteins included in the present invention have a molecular weight of approximately 65 kDa as determined by reducing gel electrophoresis and are capable of inducing ROI generation in cells. As described in more detail below, the mox proteins of the present invention also function in the regulation of cell growth, and are therefore implicated in diseases involving abnormal cell growth such as cancer. The present invention describes mox proteins found in human and rat, however, it is likely that the mox family of genes/proteins is widely distributed among multicellular organisms.

The duox proteins described herein are larger than the mox proteins and have three distinct regions: the amino terminal region having homology to peroxidase proteins, the internal region having homology to calmodulin (CAM) proteins and the carboxy-terminal region having homology to mox proteins. Human duox1 is shown in SEQ ID NO:46 and a portion of human duox2 is shown in SEQ ID NO:48. Nucleotides encoding duox1 and duox2 proteins are also shown in SEQ ID NO: 45 and SEQ ID NO:47, respectively. In addition to the human duox proteins, comparison of the sequence of human duox1 and human duox2 with genomic databases using BLAST searching resulted in the identification of two homologs of duox in C. elegans (Ce-duox1 and Ce-duox2). Drosophila also appears to have at least one duox homolog. Thus, the duox family of genes/proteins is widely distributed among multicellular organisms.

Although not wanting to be bound by the following statement, it is believed that duox1 and duox2 have dual enzymatic functions, catalyzing both the generation of superoxide and peroxidative type reactions. The latter class of reactions utilize hydrogen peroxide as a substrate (and in some cases have-been proposed to utilize superoxide as a substrate). Since hydrogen peroxide is generated spontaneously from the dismutation of superoxide, it is believed that the NAD(P)H oxidase domain generates the superoxide and/or hydrogen peroxide which can then be used as a substrate for the peroxidase domain. In support of this hypothesis, a model for the duox1 protein in C. elegans has been developed that has an extracellular N-terminal peroxidase domain, a transmembrane region and a NADPH binding site located on the cytosolic face of the plasma membrane. By analogy with the neutrophil NADPH-oxidase which generates extracellular superoxide, human duox1 is predicted to generate superoxide and its byproduct hydrogen peroxide extracellularly where it can be utilized by the peroxidase domain.

While the ROI generated by duox1 and duox2 may function as does mox1 in regulation of cell growth, the presence of the peroxidase domain is likely to confer additional biological functions. Depending upon the co-substrate, peroxidases can participate in a variety of reactions including halogenation such as the generation of hypochlorous acid (HOCl) by myeloperoxidase and the iodination of tyrosine to form thyroxin by thyroid peroxidase. Peroxidases have also been documented to participate in the metabolism of polyunsaturated fatty acids, and in the chemical modification of tyrosine in collagen (by sea urchin ovoperoxidase). Although not wanting to be bound by this statement, it is believed that the predicted transmembrane nature of duox1 facilitates its function in the formation or modification of extracellular matrix or basement membrane. Since the extracellular matrix plays an important role in tumor cell growth, invasion and metastasis, it is believed that the duox type enzymes play a pathogenic role in such conditions.

In addition to the nucleotide sequences described above, the present invention also provides vectors containing these nucleotide sequences and fragments thereof, cells transfected with these vectors which produce the proteins comprising SEQ ID NO:2, SEQ ID NO:4, SEQ ID NO:21, SEQ ID NO:42, SEQ ID NO:46, SEQ ID NO:48 and fragments thereof, and antibodies to these proteins and fragments thereof. The present invention also provides methods for stimulating cellular proliferation by administering vectors, or cells containing vectors, encoded for production of the proteins comprising SEQ ID NO:2, SEQ ID NO:4, SEQ ID NO:21, SEQ ID NO:42, SEQ ID NO:46, SEQ ID NO:48 and fragments thereof. The nucleotides and antibodies of the present invention are useful for the detection, localization and measurement of the nucleic acids encoding for the production of the proteins of the present invention, and also for the detection, localization and measurement of the proteins of the present invention. These nucleotides and antibodies can be combined with other reagents in kits for the purposes of detection, localization and measurement. These kits are useful for diagnosis and prognosis of conditions involving cellular proliferation associated with production of reactive oxygen intermediates.

The present invention solves the problems described above by providing a composition comprising the nucleotide sequence SEQ ID NO:1 and fragments thereof. The present invention also provides a composition comprising the nucleotide sequence SEQ ID NO:3 and fragments thereof. The present invention also provides a composition comprising the nucleotide sequence SEQ ID NO:22 and fragments thereof. The present invention also provides a composition comprising the nucleotide sequence SEQ ID NO:41 and fragments thereof. The present invention also provides a composition comprising the nucleotide sequence SEQ ID NO:45 and fragments thereof. The present invention also provides a composition comprising the nucleotide sequence SEQ ID NO:47 and fragments thereof.

The present invention provides a composition comprising the protein SEQ ID NO:2 encoded by the nucleotide sequence SEQ ID NO:1. The present invention provides a composition comprising the protein SEQ ID NO:4 encoded by the nucleotide sequence SEQ ID NO:3. The present invention provides a composition comprising the protein SEQ ID NO:21 encoded by the nucleotide sequence SEQ ID NO:22. The present invention provides a composition comprising the protein SEQ ID NO:42 encoded by the nucleotide sequence SEQ ID NO:41. The present invention provides a composition comprising the protein SEQ ID NO:46 encoded by the nucleotide sequence SEQ ID NO:45. The present invention provides a composition comprising the protein SEQ ID NO:48 encoded by the nucleotide sequence SEQ ID NO:47.

The present invention provides a composition comprising the protein SEQ ID NO:2 or fragments thereof, encoded by the nucleotide sequence SEQ ID NO:1 or fragments thereof. The present invention also provides a composition comprising the protein SEQ ID NO:4 or fragments thereof, encoded by the nucleotide sequence SEQ ID NO:3 or fragments thereof. The present invention also provides a composition comprising the protein SEQ ID NO:21 or fragments thereof, encoded by the nucleotide sequence SEQ ID NO:22 or fragments thereof. The present invention also provides a composition comprising the protein SEQ ID NO:42 or fragments thereof, encoded by the nucleotide sequence SEQ ID NO:41 or fragments thereof. The present invention also provides a composition comprising the protein SEQ ID NO:46 or fragments thereof, encoded by the nucleotide sequence SEQ ID NO:45 or fragments thereof. The present invention also provides a composition comprising the protein SEQ ID NO:48 or fragments thereof, encoded by the nucleotide sequence SEQ ID NO:47 or fragments thereof.

The present invention also provides vectors containing the nucleotide sequences SEQ ID NO:1, SEQ ID NO:3, SEQ ID NO:22, SEQ ID NO:41, SEQ ID NO:45, SEQ ID NO:47 or fragments thereof. The present invention also provides cells transfected with these vectors. In addition, the present invention provides cells stably transfected with the nucleotide sequence SEQ ID NO:1 or fragments thereof. The present invention also provides cells stably transfected with the nucleotide sequence SEQ ID NO:3 or fragments thereof. The present invention also provides cells stably transfected with the nucleotide sequence SEQ ID NO:22 or fragments thereof. The present invention also provides cells stably transfected with the nucleotide sequence SEQ ID NO:41 or fragments thereof. The present invention also provides cells stably transfected with the nucleotide sequence SEQ ID NO:45 or fragments thereof. The present invention also provides cells stably transfected with the nucleotide sequence SEQ ID NO:47 or fragments thereof.

The present invention provides cells stably transfected with the nucleotide sequence SEQ ID NO:1 or fragments thereof, which produce the protein SEQ ID NO:2 or fragments thereof. In addition, the present invention provides cells stably transfected with the nucleotide sequence SEQ ID NO:3 or fragments thereof which produce the protein SEQ ID NO:4 or fragments thereof. In addition, the present invention provides cells stably transfected with the nucleotide sequence SEQ ID NO:22 or fragments thereof which produce the protein SEQ ID NO:21 or fragments thereof. The present invention also provides cells stably transfected with the nucleotide sequence SEQ ID NO:41 or fragments thereof which produce the protein SEQ ID NO:42 or fragments thereof. The present invention also provides cells stably transfected with the nucleotide sequence SEQ ID NO:45 or fragments thereof which produce the protein SEQ ID NO:46 or fragments thereof. The present invention also provides cells stably transfected with the nucleotide sequence SEQ ID NO:47 or fragments thereof which produce the protein SEQ ID NO:48 or fragments thereof.

The present invention provides a method for stimulating growth by administering cells stably transfected with the nucleotide sequence SEQ ID NO:1 which produce the protein SEQ ID NO:2 or fragments thereof. The present invention also provides a method for stimulating growth by administering cells stably transfected with the nucleotide sequence SEQ ID NO:3 or fragments thereof, which produce the protein SEQ ID NO:4 or fragments thereof. The present invention also provides a method for stimulating growth by administering cells stably transfected with the nucleotide sequence SEQ ID NO:22 or fragments thereof, which produce the protein SEQ ID NO:21 or fragments thereof. The present invention also provides a method for stimulating growth by administering cells stably transfected with the nucleotide sequence SEQ ID NO:41 or fragments thereof, which produce the protein SEQ ID NO:42 or fragments thereof. The present invention also provides a method for stimulating growth by administering cells stably transfected with the nucleotide sequence SEQ ID NO:45 or fragments thereof, which produce the protein SEQ ID NO:46 or fragments thereof. The present invention also provides a method for stimulating growth by administering cells stably transfected with the nucleotide sequence SEQ ID NO:47 or fragments thereof, which produce the protein SEQ ID NO:48 or fragments thereof.

Specifically, the present invention provides a method for stimulating tumor formation by administering cells stably transfected with the nucleotide sequence SEQ ID NO:1 or fragments thereof, which produce the protein SEQ ID NO:2 or fragments thereof. The present invention also provides a method for stimulating tumor formation by administering cells stably transfected with the nucleotide sequence SEQ ID NO:3 or fragments thereof, which produce the protein SEQ ID NO:4 or fragments thereof. The present invention also provides a method for stimulating tumor formation by administering cells stably transfected with the nucleotide sequence SEQ ID NO:22 or fragments thereof, which produce the protein SEQ ID NO:21 or fragments thereof. The present invention also provides a method for stimulating tumor formation by administering cells stably transfected with the nucleotide sequence SEQ ID NO:41 or fragments thereof, which produce the protein SEQ ID NO:42 or fragments thereof. The present invention also provides a method for stimulating tumor formation by administering cells stably transfected with the nucleotide sequence SEQ ID NO:45 or fragments thereof, which produce the protein SEQ ID NO:46 or fragments thereof. The present invention also provides a method for stimulating tumor formation by administering cells stably transfected with the nucleotide sequence SEQ ID NO:47 or fragments thereof, which produce the protein SEQ ID NO:48 or fragments thereof.

The present invention may also be used to develop anti-sense nucleotide sequences to SEQ ID NO:1, SEQ ID NO:3, SEQ ID NO:22, SEQ ID NO:41, SEQ ID NO:45, SEQ ID NO:47 or fragments thereof. These anti-sense molecules may be used to interfere with translation of nucleotide sequences, such as SEQ ID NO:1, SEQ ID NO:3, SEQ ID NO:22, SEQ ID NO:41, SEQ ID NO:45, SEQ ID NO:47, or fragments thereof, that encode for proteins such as SEQ ID NO:2, SEQ ID NO:4, SEQ ID NO:21, SEQ ID NO:42, SEQ ID NO:46, SEQ ID NO:48 or fragments thereof. Administration of these anti-sense molecules, or vectors encoding for anti sense molecules, to humans and animals, would interfere with production of proteins such as SEQ ID NO:2, SEQ ID NO:4, SEQ ID NO:21, SEQ ID NO:42, SEQ ID NO:46, SEQ ID NO:48, or fragments thereof, thereby decreasing production of ROIs and inhibiting cellular proliferation. These methods are useful in producing animal models for use in study of tumor development and vascular growth, and for study of the efficacy of treatments for affecting tumor and vascular growth in vivo.

The present invention also provides a method for high throughput screening of drugs and chemicals which modulate the proliferative activity of the enzymes of the present invention, thereby affecting cell division. Combinatorial chemical libraries may be screened for chemicals which modulate the proliferative activity of these enzymes. Drugs and chemicals may be evaluated based on their ability to modulate the enzymatic activity of the expressed or endogenous proteins, including those represented by SEQ ID NO:2, SEQ ID NO:4, SEQ ID NO:21, SEQ ID NO:42, SEQ ID NO:46, SEQ ID NO:48 or fragments thereof. Endogenous proteins may be obtained from many different tissues or cells, such as colon cells. Drugs may also be evaluated based on their ability to bind to the expressed or endogenous proteins represented by SEQ ID NO:2, SEQ ID NO:4, SEQ ID NO:21, SEQ ID NO:42, SEQ ID NO:46, SEQ ID NO:48 or fragments thereof. Enzymatic activity may be NADPH- or NADH-dependent superoxide generation catalyzed by the holoprotein. Enzymatic activity may also be NADPH- or NADH-dependent diaphorase activity catalyzed by either the holoprotein or the flavoprotein domain.

By flavoprotein domain, is meant approximately the C-terminal half of the enzymes shown in SEQ ID NO:2, SEQ ID NO:4, SEQ ID NO:21, SEQ ID NO:42, or fragments thereof, and the C-terminal end of the enzymes shown in SEQ ID NO:46 and SEQ ID NO:48 (approximately the C-terminal 265 amino acids). This fragment of gp91phox has NADPH-dependent reductase activity towards cytochrome c, nitrobluetetrazolium and other dyes. Expressed proteins or fragments thereof can be used for robotic screens of existing combinatorial chemical libraries. While not wanting to be bound by the following statement, it is believed that the NADPH or NADH binding site and the FAD binding site are useful for evaluating the ability of drugs and other compositions to bind to the mox and duox enzymes or to modulate their enzymatic activity. The use of the holoprotein or the C-terminal half or end regions are preferred for developing a high throughput drug screen. Additionally, the N-terminal one-third of the duox domain (the peroxidase domain) may also be used to evaluate the ability of drugs and other compositions to inhibit the peroxidase activity, and for further development of a high throughput drug screen.

The present invention also provides antibodies directed to the proteins SEQ ID NO:2, SEQ ID NO:4, SEQ ID NO:21, SEQ ID NO:42, SEQ ID NO:46, SEQ ID NO:48 and fragments thereof. The antibodies of the present invention are useful for a variety of purposes including localization, detection and measurement of the proteins SEQ ID NO:2, SEQ ID NO:4, SEQ ID NO:21, SEQ ID NO:42, SEQ ID NO:46, SEQ ID NO:48 and fragments thereof. The antibodies may be employed in kits to accomplish these purposes. These antibodies may also be linked to cytotoxic agents for selected killing of cells. The term antibody is meant to include any class of antibody such as IgG, IgM and other classes. The term antibody also includes a completely intact antibody and also fragments thereof, including but not limited to Fab fragments and Fab+Fc fragments.

The present invention also provides the nucleotide sequences SEQ ID NO:1, SEQ ID NO:3, SEQ ID NO:22, SEQ ID NO:41, SEQ ID NO:45, SEQ ID NO:47 and fragments thereof. These nucleotides are useful for a variety of purposes including localization, detection, and measurement of messenger RNA involved in synthesis of the proteins represented as SEQ ID NO:2, SEQ ID NO:4, SEQ ID NO:21, SEQ ID NO:42, SEQ ID NO:46, SEQ ID NO:48 and fragments thereof. These nucleotides may also be used in the construction of labeled probes for the localization, detection, and measurement of nucleic acids such as messenger RNA or alternatively for the isolation of larger nucleotide sequences containing the nucleotide sequences shown in SEQ ID NO:1, SEQ ID NO:3, SEQ ID NO:22, SEQ ID NO:41, SEQ ID NO:45, SEQ ID NO:47 or fragments thereof. These nucleotide sequences may be used to isolate homologous strands from other species using techniques known to one of ordinary skill in the art. These nucleotide sequences may also be used to make probes and complementary strands. In particular, the nucleotide sequence shown in SEQ ID NO:47 may be used to isolate the complete coding sequence for duox2. The nucleotides may be employed in kits to accomplish these purposes.

Most particularly, the present invention involves a method for modulation of growth by modifying the proteins represented as SEQ ID NO:2, SEQ ID NO:4, SEQ ID NO:21, SEQ ID NO:42, SEQ ID NO:46, SEQ ID NO:48 or fragments thereof.

The term "mitogenic regulators" is used herein to mean any molecule that acts to affect cell division.

The term "animal" is used herein to mean humans and non-human animals of both sexes.

The terms "a", "an" and "the" as used herein are defined to mean one or more and include the plural unless the context is inappropriate.

"Proteins", "peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the protein, or to the alpha-amino group (imino group when participating in a peptide bond) of an amino acid at any other location within the protein. Similarly, the term "carboxy terminus" (abbreviated C-terminus) refers to the free carboxyl group on the amino acid at the carboxy terminus of a protein, or to the carboxyl group of an amino acid at any other location within the protein.

Typically, the amino acids making up a protein are numbered in order, starting at the amino terminal and increasing in the direction toward the carboxy terminal of the protein. Thus, when one amino acid is said to "follow" another, that amino acid is positioned closer to the carboxy terminal of the protein than the preceding amino acid.

The term "residue" is used herein to refer to an amino acid (D or L) or an amino acid mimetic that is incorporated into a protein by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V); and
6) Phenylalanine (F), Tyrosine (Y), Tryptophan (W).

When the peptides are relatively short in length (i.e., less than about 50 amino acids), they are often synthesized using standard chemical peptide synthesis techniques. Solid phase synthesis in which the C-terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the antigenic epitopes described herein are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

One of skill in the art will recognize that after chemical synthesis, biological expression or purification, the desired proteins, fragments thereof and peptides may possess a conformation substantially different than the native conformations of the proteins, fragments thereof and peptides. In this case, it is often necessary to denature and reduce protein and then to cause the protein to re-fold into the preferred conformation. Methods of reducing and denaturing proteins and inducing re-folding are well known to those of skill in the art.

The genetic constructs of the present invention include coding sequences for different proteins, fragments thereof, and peptides. The genetic constructs also include epitopes or domains chosen to permit purification or detection of the expressed protein. Such epitopes or domains include DNA sequences encoding the glutathione binding domain from glutathione S-transferase, hexa-histidine, thioredoxin, hemagglutinin antigen, maltose binding protein, and others commonly known to one of skill in the art. The preferred genetic construct includes the nucleotide sequences of SEQ ID NO:1, SEQ ID NO:3, SEQ ID NO:22, SEQ ID NO:41, SEQ ID NO:45, SEQ ID NO:47 or fragments thereof. It is to be understood that additional or alternative nucleotide sequences may be included in the genetic constructs in order to encode for the following: a) multiple copies of the desired proteins, fragments thereof, or peptides; b) various combinations of the desired proteins, fragments thereof, or peptides; and c) conservative modifications of the desired proteins, fragments thereof, or peptides, and combinations thereof. Preferred proteins include the human mox1 protein and human mox2 protein shown as SEQ ID NO:2 and SEQ ID NO:4, respectively, and fragments thereof. Some preferred fragments of the human mox1 protein (SEQ ID NO:2) include but are not limited to the proteins shown as SEQ ID NO:23, SEQ ID NO:24, and SEQ ID NO:25. The protein mox1 is also called p65mox in this application. Another preferred protein of the present invention is rat mox1 protein shown as SEQ ID NO:21 and fragments thereof. Another preferred protein of the present invention is rat mox1B protein shown as SEQ ID NO:42 and fragments thereof. Yet another preferred protein of the present invention is duox1 protein shown as SEQ ID NO:46 and fragments thereof. Still another preferred protein of the present invention is duox2 protein. A partial amino acid sequence of the duox2 protein is shown as SEQ ID NO:48.

The nucleotide sequences of the present invention may also be employed to hybridize to nucleic acids such as DNA or RNA nucleotide sequences under high stringency conditions which permit detection, for example, of alternately spliced messages.

The genetic construct is expressed in an expression system such as in NIH 3T3 cells using recombinant sequences in a pcDNA-3 vector (Invitrogen, Carlsbad, Calif.) to produce a recombinant protein. Preferred expression systems include but are not limited to Cos-7 cells, insect cells using recombinant baculovirus, and yeast. It is to be understood that other expression systems known to one of skill in the art may be used for expression of the genetic constructs of the present invention. The preferred proteins of the present invention are the proteins referred to herein as human mox1 and human mox2 or fragments thereof which have the amino acid sequences set forth in SEQ ID NO:3 and SEQ ID NO:4, respectively, or an amino acid sequence having amino acid substitutions as defined in the definitions that do not significantly alter the function of the recombinant protein in an adverse manner. Another preferred protein of the present invention is referred to herein as rat mox1 and has the amino acid sequence set forth in SEQ ID NO:21. Yet another preferred protein of the present invention is referred to herein as rat mox1B and has the amino acid sequence set forth in SEQ ID NO:42. Two other preferred proteins of the present invention are referred to herein as human duox1 and human duox2, or fragments thereof, which have the amino acid sequences set forth in SEQ ID NO:46 and SEQ ID NO:48, respectively, or an amino acid sequence having amino acid substitutions as defined in the definitions that do not significantly alter the function of the recombinant protein in an adverse manner.

Terminology

It should be understood that some of the terminology used to describe the novel mox and duox proteins contained herein is different from the terminology in U.S. Provisional Application Ser. No. 60/107,911 and U.S. Provisional Application Ser. No. 60/149,332 upon which this application claims priority in part. As described herein, the term "human mox1" refers to a protein comprising an amino acid sequence as set forth in SEQ ID NO:2, or a fragment thereof, and encoded by the nucleotide sequence as set forth in SEQ ID NO:1, or a fragment thereof. As described herein, the term "human mox2" refers to a protein comprising an amino acid sequence as set forth in SEQ ID NO:4, or a fragment thereof, and encoded by the nucleotide sequence as set forth in SEQ ID NO:3, or a fragment thereof As described herein, the term "human duox1" refers to a protein comprising an amino acid sequence as set forth in SEQ ID NO:46, or a fragment thereof, and encoded by the nucleotide sequence as set forth in SEQ ID NO:45, or a fragment thereof. As described herein, the term "human duox2" refers to a protein comprising an amino acid sequence as set forth in SEQ ID NO:48, or a fragment thereof, and encoded by the nucleotide sequence as set forth in SEQ ID NO:47, or a fragment thereof.

Construction of the Recombinant Gene

The desired gene is ligated into a transfer vector, such as pcDNA3, and the recombinants are used to transform host cells such as Cos-7 cells. It is to be understood that different transfer vectors, host cells, and transfection methods may be employed as commonly known to one of ordinary skill in the art. Six desired genes for use in transfection are shown in SEQ ID NO:1, SEQ ID NO:3, SEQ ID NO:22, SEQ ID NO:41 SEQ ID NO:45 and SEQ ID NO:47. For example, lipofectamine-mediated transfection and in vivo homologous recombination was used to introduce the mox1 gene into NIH 3T3 cells.

The synthetic gene is cloned and the recombinant construct containing mox or duox gene is produced and grown in confluent monolayer cultures of a Cos-7 cell line. The expressed recombinant protein is then purified, preferably using affinity chromatography techniques, and its purity and specificity determined by known methods.

A variety of expression systems may be employed for expression of the recombinant protein. Such expression methods include, but are not limited to the following: bacterial expression systems, including those utilizing *E. coli* and *Bacillus subtilis*; virus systems; yeast expression systems; cultured insect and mammalian cells; and other expression systems known to one of ordinary skill in the art.

Transfection of Cells

It is to be understood that the vectors of the present invention may be transfected into any desired cell or cell line. Both in vivo and in vitro transfection of cells are contemplated as part of the present invention. Preferred cells for transfection include but are not limited to the following: fibroblasts (possibly to enhance wound healing and skin formation), granulocytes (possible benefit to increase function in a compromised immune system as seen in AIDS, and aplastic anemia), muscle cells, neuroblasts, stem cells, bone marrow cells, osteoblasts, B lymphocytes, and T lymphocytes.

Cells may be transfected with a variety of methods known to one of ordinary skill in the art and include but are not limited to the following: electroporation, gene gun, calcium phosphate, lipofectamine, and fugene, as well as adenoviral transfection systems.

Host cells transfected with the nucleic acids represented in SEQ ID NO:1, SEQ ID NO:3, SEQ ID NO:22, SEQ ID NO:41 SEQ ID NO:45 and SEQ ID NO:47, or fragments thereof, are used to express the proteins SEQ ID NO:2, SEQ ID NO:4, SEQ ID NO:21, SEQ ID NO:42, SEQ ID NO:46 and SEQ ID NO:48, respectively, or fragments thereof.

These expressed proteins are used to raise antibodies. These antibodies may be used for a variety of applications including but not limited to immunotherapy against cancers expressing one of the mox or duox proteins, and for detection, localization and measurement of the proteins shown in SEQ ID NO:2, SEQ ID NO:4, SEQ ID NO:21, SEQ ID NO:42, SEQ ID NO:46 or SEQ ID NO:48 or fragments thereof.

Purification and Characterization of the Expressed Protein

The proteins of the present invention can be expressed as a fusion protein with a poly histidine component, such as a hexa histidine, and purified by binding to a metal affinity column using nickel or cobalt affinity matrices. The protein can also be expressed as a fusion protein with glutathione S-transferase and purified by affinity chromatography using a glutathione agarose matrix. The protein can also be purified by immunoaffinity chromatography by expressing it as a fusion protein, for example with hemagglutinin antigen. The expressed or naturally occurring protein can also be purified by conventional chromatographic and purification methods which include anion and cation exchange chromatography, gel exclusion chromatography, hydroxylapatite chromatography, dye binding chromatography, ammonium sulfate precipitation, precipitation in organic solvents or other techniques commonly known to one of skill in the art.

Methods of Assessing Activity of Expressed Proteins

Different methods are available for assessing the activity of the expressed proteins of the present invention, including but not limited to the proteins represented as SEQ ID NO:2, SEQ ID NO:4, SEQ ID NO:21, SEQ ID NO:42, SEQ ID NO:46 or SEQ ID NO:48 substituted analogs thereof, and fragments thereof.

1. Assays of the Holoprotein and Fragments Thereof for Superoxide Generation:

A. General Considerations.

These assays are useful in assessing efficacy of drugs designed to modulate the activity of the enzymes of the present invention. The holoprotein may be expressed in COS-7 cells, NIH 3T3 cells, insect cells (using baculoviral technology) or other cells using methods known to one of skill in the art. Membrane fractions or purified protein are used for the assay. The assay may require or be augmented by other cellular proteins such as p47phox, p67phox, and Rac1, as well as potentially other unidentified factors (e.g., kinases or other regulatory proteins).

B. Cytochrome c Reduction.

NADPH or NADH is used as the reducing substrate, in a concentration of about 100 µM. Reduction of cytochrome c is monitored spectrophotometrically by the increase in absorbance at 550 nm, assuming an extinction coefficient of 21 $mM^{-1}cm^{-1}$. The assay is performed in the absence and presence of about 10 µg superoxide dismutase. The superoxide-dependent reduction is defined as cytochrome c reduction in the absence of superoxide dismutase minus that in the presence of superoxide dismutase (Uhlinger et al. (1991) *J. Biol. Chem.* 266, 20990–20997). Acetylated cytochrome c may also be used, since the reduction of acetylated cytochrome c is thought to be exclusively via superoxide.

C. Nitroblue Tetrazolium Reduction.

For nitroblue tetrazolium (NBT) reduction, the same general protocol is used, except that NBT is used in place of cytochrome c. In general, about 1 mL of filtered 0.25% nitrotetrazolium blue (Sigma, St. Louis, Mo.) is added in Hanks buffer without or with about 600 Units of superoxide dismutase (Sigma) and samples are incubated at approximately 37° C. The oxidized NBT is clear, while the reduced NBT is blue and insoluble. The insoluble product is collected by centrifugation, and the pellet is re-suspended in about 1 mL of pyridine (Sigma) and heated for about 10 minutes at 100° C. to solubilize the reduced NBT. The concentration of reduced NBT is determined by measuring the absorbance at 510 nm, using an extinction coefficient of 11,000 $M^{-1}cm^{-1}$. Untreated wells are used to determine cell number.

D. Luminescence.

Superoxide generation may also be monitored with a chemiluminescence detection system utilizing lucigenin (bis-N-methylacridinium nitrate, Sigma, St. Louis, Mo.). The sample is mixed with about 100 µM NADPH (Sigma, St. Louis, Mo.) and 10 µM lucigenin (Sigma, St. Louis, Mo.) in a volume of about 150 µL Hanks solution. Luminescence is monitored in a 96-well plate using a LumiCounter (Packard, Downers Grove, Ill.) for 0.5 second per reading at approximately 1 minute intervals for a total of about 5 minutes; the highest stable value in each data set is used for comparisons. As above, superoxide dismutase is added to some samples to prove that the luminescence arises from superoxide. A buffer blank is subtracted from each reading (Ushio-Fukai et al. (1996) *J. Biol. Chem.* 271, 23317–23321).

E. Assays in Intact Cells.

Assays for superoxide generation may be performed using intact cells, for example, the mox-transfected NIH 3T3 cells. In principle, any of the above assays can be used to evaluate superoxide generation using intact cells, for example, the mox-transfected NIH 3T3 cells. NBT reduction is a preferred assay method.

2. Assays of Truncated Proteins Comprised of Approximately the C-Terminal 265 Amino Acid Residues While not wanting to be bound by the following statement, the truncated protein comprised of approximately the C-terminal 265 amino acid residues is not expected to generate superoxide, and therefore, superoxide dismutase is not added in assays of the truncated protein. Basically, a similar assay is established and the superoxide-independent reduction of NBT, cytochrome c, dichlorophenolindophenol, ferricyanide, or another redox-active dye is examined.

Nucleotides and Nucleic Acid Probes

The nucleotide sequences SEQ ID NO:1, SEQ ID NO:3, SEQ ID NO:22, SEQ ID NO:41 SEQ ID NO:45 and SEQ ID NO:47, as well as fragments thereof and PCR primers therefor, may be used, respectively, for localization, detection and measurement of nucleic acids related to SEQ ID NO:1, SEQ ID NO:3, SEQ ID NO:22, SEQ ID NO:41 SEQ ID NO:45 and SEQ ID NO:47, as well as fragments thereof. The nucleotide sequences SEQ ID NO:1 and SEQ ID NO:3 are also called the human mox1 gene and the human mox2 gene in this application. SEQ ID NO:22 is also known as the rat mox1 gene in this application. SEQ ID NO:41 is also known as the rat mox1B gene in this application. SEQ ID NO:45 is also known as the human duox1 gene in this application. SEQ ID NO:47 is also known as the human duox2 gene in this application.

The nucleotide sequences SEQ ID NO:1, SEQ ID NO:3, SEQ ID NO:22, SEQ ID NO:41 SEQ ID NO:45 and SEQ ID NO:47, as well as fragments thereof, may be used to create probes to isolate larger nucleotide sequences containing the nucleotide sequences SEQ ID NO:1, SEQ ID NO:3, SEQ ID NO:22, SEQ ID NO:41 SEQ ID NO:45 and SEQ ID NO:47, respectively. The nucleotide sequences SEQ ID NO:1, SEQ ID NO:3, SEQ ID NO:22, SEQ ID NO:41 SEQ ID NO:45 and SEQ ID NO:47, as well as fragments thereof, may also be used to create probes to identify and isolate mox and duox proteins in other species.

The nucleic acids described herein include messenger RNA coding for production of SEQ ID NO:2, SEQ ID NO:4, SEQ ID NO:21, SEQ ID NO:42, SEQ ID NO:46, SEQ ID NO:48 and fragments thereof. Such nucleic acids include but are not limited to cDNA probes. These probes may be labeled in a variety of ways known to one of ordinary skill in the art. Such methods include but are not limited to isotopic and non-isotopic labeling. These probes may be used for in situ hybridization for localization of nucleic acids such as mRNA encoding for SEQ ID NO:2, SEQ ID NO:4, SEQ ID NO:21, SEQ ID NO:42, SEQ ID NO:46, SEQ ID NO:48 and fragments thereof. Localization may be performed using in situ hybridization at both ultrastructural and light microscopic levels of resolution using techniques known to one of ordinary skill in the art.

These probes may also be employed to detect and quantitate nucleic acids and mRNA levels using techniques known to one of ordinary skill in the art including but not limited to solution hybridization.

Antibody Production

The proteins shown in SEQ ID NO:2, SEQ ID NO:4, SEQ ID NO:21, SEQ ID NO:42, SEQ ID NO:46, SEQ ID NO:48, or fragments thereof, are combined with a pharmaceutically acceptable carrier or vehicle to produce a pharmaceutical composition and administered to animals for the production of polyclonal antibodies using methods known to one of ordinary skill in the art. The preferred animals for antibody production are rabbits and mice. Other animals may be employed for immunization with these proteins or fragments thereof. Such animals include, but are not limited to the following; sheep, horses, pigs, donkeys, cows, monkeys and rodents such as guinea pigs and rats.

The terms "pharmaceutically acceptable carrier or pharmaceutically acceptable vehicle" are used herein to mean any liquid including but not limited to water or saline, oil, gel, salve, solvent, diluent, fluid ointment base, liposome, micelle, giant micelle, and the like, which is suitable for use in contact with living animal or human tissue without causing adverse physiological responses, and which does not interact with the other components of the composition in a deleterious manner.

The pharmaceutical compositions may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art.

Preferred unit dosage formulations are those containing a dose or unit, or an appropriate fraction thereof, of the administered ingredient. It should be understood that in addition to the ingredients, particularly mentioned above, the formulations of the present invention may include other agents commonly used by one of ordinary skill in the art.

The pharmaceutical composition may be administered through different routes, such as oral, including buccal and sublingual, rectal, parenteral, aerosol, nasal, intramuscular, subcutaneous, intradermal, and topical. The pharmaceutical composition of the present invention may be administered in different forms, including but not limited to solutions, emulsions and suspensions, microspheres, particles, microparticles, nanoparticles, and liposomes. It is expected that from about 1 to 7 dosages may be required per immunization regimen. Initial injections may range from about 0.1 µg to 1 mg, with a preferred range of about 1 µg to 800 µg, and a more preferred range of from approximately 25 µg to 500 µg. Booster injections may range from 0.1 µg to 1 mg, with a preferred range of approximately 1 µg to 800 µg, and a more preferred range of about 10 µg to 500 µg.

The volume of administration will vary depending on the route of administration and the size of the recipient. For example, intramuscular injections may range from about 0.1 ml to 1.0 ml.

The pharmaceutical composition may be stored at temperatures of from about 4° C. to −100° C. The pharmaceutical composition may also be stored in a lyophilized state at different temperatures including room temperature. The pharmaceutical composition may be sterilized through conventional means known to one of ordinary skill in the art. Such means include, but are not limited to filtration, radiation and heat. The pharmaceutical composition of the present invention may also be combined with bacteriostatic agents, such as thimerosal, to inhibit bacterial growth.

Adjuvants

A variety of adjuvants known to one of ordinary skill in the art may be administered in conjunction with the protein in the pharmaceutical composition. Such adjuvants include, but are not limited to the following: polymers, co-polymers such as polyoxyethylene-polyoxypropylene copolymers, including block co-polymers; polymer P1005; Freund's complete adjuvant (for animals); Freund's incomplete adjuvant; sorbitan monooleate; squalene; CRL-8300 adjuvant; alum; QS 21, muramyl dipeptide; trehalose; bacterial extracts, including mycobacterial extracts; detoxified endotoxins; membrane lipids; or combinations thereof.

Monoclonal antibodies can be produced using hybridoma technology in accordance with methods well known to those skilled in the art. The antibodies are useful as research or diagnostic reagents or can be used for passive immunization. The composition may optionally contain an adjuvant.

The polyclonal and monoclonal antibodies useful as research or diagnostic reagents may be employed for detection and measurement of SEQ ID NO:2, SEQ ID NO:4, SEQ ID NO:21, SEQ ID NO:42, SEQ ID NO:46, SEQ ID NO:48 and fragments thereof. Such antibodies may be used to detect these proteins in a biological sample, including but not limited to samples such as cells, cellular extracts, tissues, tissue extracts, biopsies, tumors, and biological fluids. Such detection capability is useful for detection of disease related to these proteins to facilitate diagnosis and prognosis and to suggest possible treatment alternatives.

Detection may be achieved through the use of immunocytochemistry, ELISA, radioimmunoassay or other assays as commonly known to one of ordinary skill in the art. The mox1, mox2, duox1 and duox2 proteins, or fragments thereof, may be labeled through commonly known approaches, including but not limited to the following: radiolabeling, dyes, magnetic particles, biotin-avidin, fluorescent molecules, chemiluminescent molecules and systems, ferritin, colloidal gold, and other methods known to one of skill in the art of labeling proteins.

Administration of Antibodies

The antibodies directed to the proteins shown as SEQ ID NO:2, SEQ ID NO:4, SEQ ID NO:21, SEQ ID NO:42, SEQ ID NO:46 or SEQ ID NO:48, or directed to fragments thereof, may also be administered directly to humans and animals in a passive immunization paradigm. Antibodies directed to extracellular portions of SEQ ID NO:2, SEQ ID NO:4, SEQ ID NO:21, SEQ ID NO:42, SEQ ID NO:46 or SEQ ID NO:48 bind to these extracellular epitopes. Attachment of labels to these antibodies facilitates localization and visualization of sites of binding. Attachment of molecules such as ricin or other cytotoxins to these antibodies helps to selectively damage or kill cells expressing SEQ ID NO:2, SEQ ID NO:4, SEQ ID NO:21, SEQ ID NO:42, SEQ ID NO:46, SEQ ID NO:48 or fragments thereof.

Kits

The present invention includes kits useful with the antibodies, nucleic acids, nucleic acid probes, labeled antibodies, labeled proteins or fragments thereof for detection, localization and measurement of SEQ ID NO:1, SEQ ID NO:2, SEQ ID NO:3, SEQ ID NO:4, SEQ ID NO:21, SEQ ID NO:22, SEQ ID NO:41, SEQ ID NO:42, SEQ ID NO:45, SEQ ID NO:46, SEQ ID NO:47, SEQ ID NO:48 or combinations and fragments thereof.

Kits may be used for immunocytochemistry, in situ hybridization, solution hybridization, radioimmunoassay, ELISA, Western blots, quantitative PCR, and other assays for the detection, localization and measurement of these nucleic acids, proteins or fragments thereof using techniques known to one of skill in the art.

The nucleotide sequences shown in SEQ ID NO:1, SEQ ID NO:3, SEQ ID NO:22, SEQ ID NO:41 SEQ ID NO:45, SEQ ID NO:47, or fragments thereof, may also be used under high stringency conditions to detect alternately spliced messages related to SEQ ID NO:1, SEQ ID NO:3, SEQ ID NO:22, SEQ ID NO:41 SEQ ID NO:45, SEQ ID NO:47 or fragments thereof, respectively.

As discussed in one of the Examples, rat mox1 protein (SEQ ID NO: 21) is similar to mouse gp91 protein (SEQ ID NO: 38), whereas rat mox1B protein (SEQ ID NO:42) is similar to human gp91 protein (SEQ ID NO:12). This observation suggests that other isoforms of mouse and human gp91 may exist. In addition, another subtype of human mox1, similar to rat mox1B (SEQ ID NO:42), also exists. The presence of two isoforms of rat mox1 protein in vascular smooth muscle may have important physiological consequences and biomedical applications. For example, the two isoforms may have different biological activities, different tissue distributions and may be regulated differently in physiological and/or pathological conditions. The fact that mox1B (SEQ ID NO:42) was isolated from cells exposed to angiotensin II, known to promote oxidative stress and vascular growth, suggests that it may be upregulated by this hormone and may be overexpressed in disease. Therefore, the diagnostic kits of the present invention can measure the relative expression of the two mox isoforms. The diagnostic kits may also measure or detect the relative expression of the mox proteins described herein (i.e. human mox1 and/or human mox2) and duox proteins described herein (i.e. human duox1 and/or human duox2).

Fragments of SEQ ID NO:1, SEQ ID NO:3, SEQ ID NO:22, SEQ ID NO:41 SEQ ID NO:45 and SEQ ID NO:47 containing the relevant hybridizing sequence can be synthesized onto the surface of a chip array. RNA samples, e.g., from tumors, are then fluorescently tagged and hybridized onto the chip for detection. This approach may be used diagnostically to characterize tumor types and to tailor treatments and/or provide prognostic information. Such prognostic information may have predictive value concerning disease progression and life span, and may also affect choice of therapy.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Sequence Analysis and Cloning of the Human mox1 cDNA (SEQ ID NO:1) Encoding for Production of the Human mox1 Protein p65mox (SEQ ID NO:2)

Using gp91phox as a query sequence, a 334 base sequenced portion of expressed sequence tag (EST) 176696 (GenBank Accession number AA305700) showed 68.8% sequence identity at the predicted amino acid level with human (h) gp91phox. The bacterial strain number 129134 containing the EST sequence in the pBluescript SK− vector, was purchased from American Tissue Type Culture Collection (ATCC, Rockville, Md.). The EST sequence was originally cloned from a Caco-2 human colon carcinoma cell line. The EST176696 DNA was further sequenced using the T7 and T3 vector promoters and primers designed to match the known 3' sequence. Internal primers used for sequencing were as follows: 5'-AAC AAG CGT GGC TTC AGC ATG-3' SEQ ID NO:5 (251S, numbering is based on the nucleotides from the 5' end of LST176696, and S indicates the sense direction), 5'-AGC AAT ATT GTT GGT CAT-3' SEQ ID NO:6 (336S), 5'-GAC TTG ACA GAA AAT CTA TAA GGG-3' SEQ ID NO:7 (393S), 5'-TTG TAC CAG ATG GAT TTC AA-3' SEQ ID NO:8 (673A, A indicates the antisense direction), 5'-CAG GTC TGA AAC AGA AAA CCT-3' SEQ ID NO:9 (829S), 5'-ATG AAT TCT CAT TAA TTA TTC AAT AAA-3' SEQ ID NO:10 (1455A). The coding sequence in EST176696 showed homology to a 250 amino acid stretch corresponding to the N-terminal 44% of human gp91phox, and contained a stop codon corresponding to the location in human gp91phox. 5' Rapid amplification of cDNA ends (RACE) was carried out using a human colon cDNA library and Marathon cDNA Amplification Kit (ClonTech) using 5'-ATC TCA AAA GAC TCT GCA CA-3' SEQ ID NO:11 (41A) as an internal gene-specific primer (Frohman et al. (1988) *Proc. Natl. Acad. Sci. USA* 85, 8998–9002). 5' RACE resulted in a 1.1 kb fragment representing the complete 5' sequence, based on homology with gp91phox. Reamplification was performed with primers spanning the putative start and stop codons, using the 1.1 kb 5' RACE product and pSK-EST176696 for primer design. The amplified 1.7 kb fragment was TA cloned into the PCR2.1 vector (Invitrogen, Carlsbad, Calif.). This recombinant vector is referred to as PCR-mox.

Figure 1A:
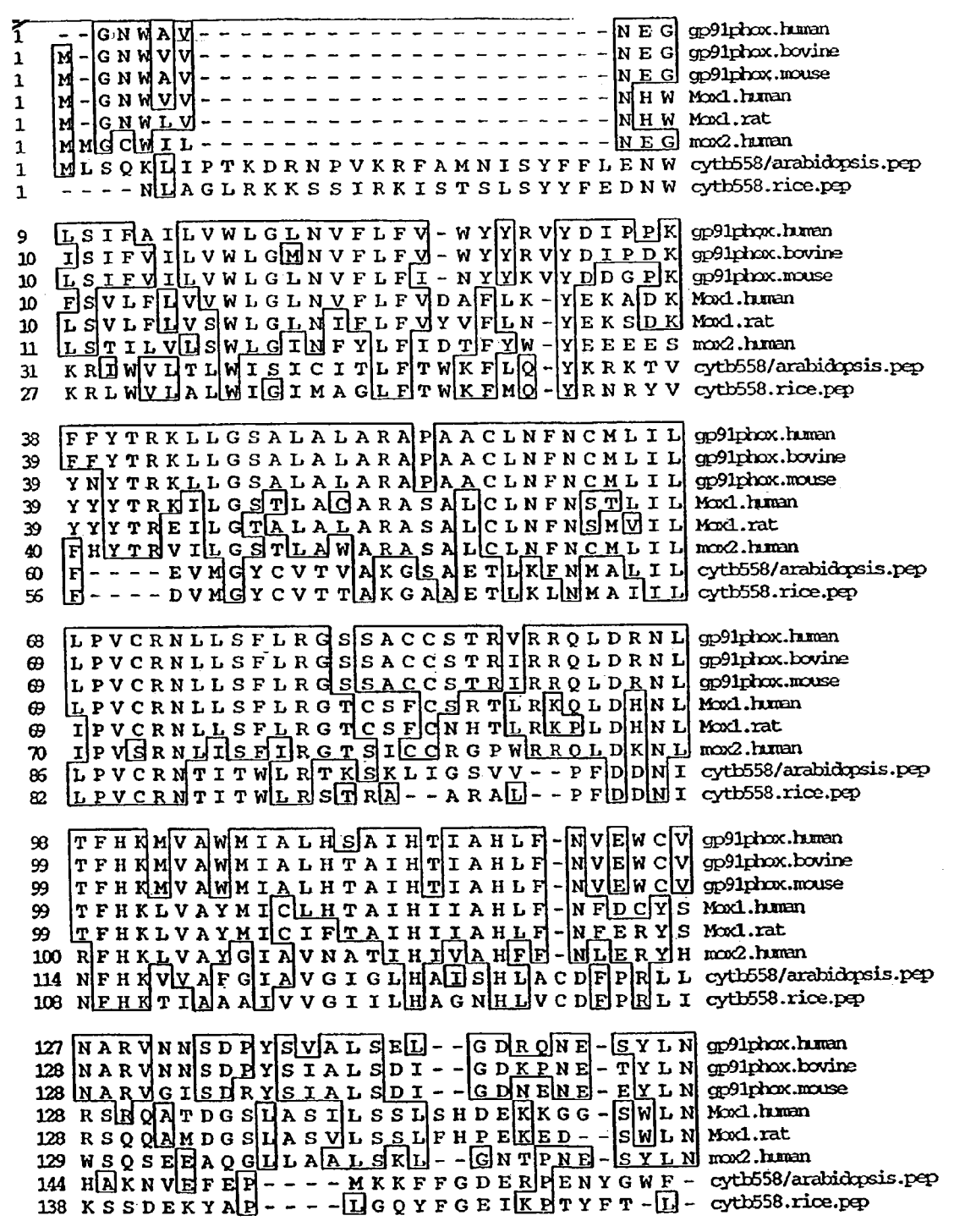

FIG. 1(a–d) presents a comparison of the present amino acid sequences of human, bovine and murine gp91 phox with the human and rat mox1 proteins of the present invention and the human duox2 protein of the present invention. Also shown are the amino acid sequences for related plant enzyme proteins.

The encoded hp65mox ("mox" referring to mitogenic oxidase and "65" referring to its predicted molecular weight) is listed as SEQ ID NO:2. h-gp91phox (SEQ ID NO:12) and SEQ ID NO:2 differ in length by 3 residues and are 70% identical in their amino acid sequence. h-gp91phox and SEQ ID NO:2 show a greater percentage identity in the C-terminal half of the molecule which contains the putative NADPH and FAD binding sites, and there are several relatively long stretches of complete identity within this region.

A dendrogram (FIG. 2) comparing the amino acid sequences of mouse and human gp91phox with that of mox1 SEQ ID NO:2 shows that the latter probably represents a distinct isoform of gp91phox. Two plant homologs of cytochrome $b_{558}$ large subunit are also indicated and represent more distant relatives of the human sequences. Human (and rat mox1 described more fully below) lack asparagine-linked glycosylation sites, which are seen in the highly glycosylated human and mouse gp91phox. Additionally, the hydropathy profiles of human gp91phox and mox1 are nearly identical and include five very hydrophobic stretches in the amino-terminal half of the molecules which are predicted to be membrane-spanning regions.

EXAMPLE 2

Expression of Mox1

Human multiple tissue northern (MTN) Blot I and Human MTN Blot IV (ClonTech) membranes were hybridized with the putative coding region of the PCR-mox vector at 68° C. for several hours. The mox coding region was labeled by random priming with [α-$^{32}$P]dCTP (10 μCi) using the Prime-It II kit (Stratagene). For analysis of mox1 expression in cell lines, total RNA was prepared from $10^6$ cells using the High Pure RNA Isolation Kit (Boehringer Mannheim) or RNeasy kit (Quiagen). Total RNA (10–20 μg) was separated on a 1% agarose formaldehyde mini-gel and transferred to a Nytran filter (Biorad) and immobilized by ultraviolet cross-linking.

Northern blotting revealed that the major location of mRNA coding for the mox1 protein was colon. The message was also detected in prostate and uterus. The human colon-carcinoma cell line, Caco-2, also expressed large quantities of mox1 message. Northern blotting of mRNA from rat aortic smooth muscle cells also showed strong hybridization, which increased roughly two-fold within 12 hours after treatment with platelet-derived growth factor. This increase in the expression of rat mox1 is consistent with the idea that mox1 contributes to the growth-stimulatory effects of PDGF.

EXAMPLE 3

Transfection of NIH3T3 Cells with SEQ ID NO:1

The nucleotide sequence (SEQ ID NO:1) encoding for production of the mox1 protein (SEQ ID NO:2) was subcloned into the Not1 site of the pEF-PAC vector (obtained from Mary Dinauer, Indiana University Medical School, Indianapolis, Ind.) which has a puromycin resistance gene. Transfection was carried out as described in Sambrook et al., Molecular Cloning, A Laboratory Manual, Volumes 1–3, 2nd edition, Cold Spring Harbor Laboratory Press, New York, 1989. The SEQ ID NO:1 in pEF-PAC and the empty vector were separately transfected into NIH 3T3 cells using Fugene 6 (Boeringer Mannheim). About $2 \times 10^6$ cells maintained in DMEM containing 10% calf serum were transfected with 10 μg of DNA. After 2 days, cells were split and selected in the same medium containing 1 mg/ml puromycin. Colonies that survived in selection media for 10 to 14 days were subcultured continuously in the presence of puromycin.

Transfected cells exhibited a "transformed"-like morphology, similar to that seen with (V12) Ras-transfected cells, characterized by long spindle-like cells. The parent NIH 3T3 cells or cells transfected with the empty vector showed a normal fibroblast-like morphology.

EXAMPLE 4

Expression of Mox1 (SEQ ID NO:1) in Transfected NIH3T3 Cells

To verify the expression of mox1 mRNA after transfection, RT-PCR and Northern blotting were performed. Total RNAs were prepared from 10⁶ cells using the High Pure RNA Isolation Kit (Boeringer Mannheim) or RNeasy kit (Qiagen). cDNAs for each colony were prepared from 1–2 µg of total RNA using Advantage RT-PCR Kit (ClonTech). PCR amplification was performed using primers, 5'-TTG GCT AAA TCC CAT CCA-3' SEQ ID NO:13 (NN459S, numbering containing NN indicates numbering from the start codon of mox1) and 5'-TGC ATG ACC AAC AAT ATT GCT G-3' SEQ ID NO:14 (NN1435A). For Northern blotting, 10–20 µg of total RNA was separated on a 1% agarose formaldehyde gel and transferred to a nylon filter. After ultraviolet (UV) cross-linking, filters were used for Northern blotting assay as described in Example 2.

Colonies expressing large amounts of mox1 mRNA were chosen for further analysis. The expression of mRNA for glyceraldehyde 3 phosphate dehydrogenase in the various cell lines was normal.

EXAMPLE 5

Colony Formation on Soft Agar $10^5$ to $10^3$ cells stably transfected with human mox1 gene SEQ ID NO:1 and with empty vector were prepared in 0.3% warm (40° C.) agar solution containing DMEM and 10% calf serum. Cells were distributed onto a hardened 0.6% agar plate prepared with DMEM and 10% calf serum. After three weeks in culture (37° C., 5% $CO_2$) colony formation was observed by microscopy.

Cells which were stably transfected with the empty vector and cultured in soft agar for 3 weeks as above did not display anchorage independent growth. In contrast, NIH 3T3 cells which had been stably transfected with the mox1 (SEQ ID NO:1) and cultured for 3 weeks in soft agar demonstrated anchorage independent growth of colonies.

EXAMPLE 6

NADPH-Dependent Superoxide Generation Assay

In one embodiment of the present invention, NIH 3T3 cells stably transfected with the human mox1 gene (SEQ ID NO:1) were analyzed for superoxide generation using the lucigenin (Bis-N-methylacridinium luminescence assay (Sigma, St. Louis, Mo., Li et al. (1998) *J. Biol. Chem.* 273, 2015–2023). Cells were washed with cold HANKS' solution and homogenized on ice in HANKS' buffer containing 15% sucrose using a Dounce homogenizer. Cell lysates were frozen immediately in a dry ice/ethanol bath. For the assay, 30 µg of cell lysate was mixed with 200 µM NADPH and 500 µM lucigenin. Luminescence was monitored using a LumiCounter (Packard) at three successive one minute intervals and the highest value was used for comparison. Protein concentration was determined by the Bradford method.

Superoxide generation was monitored in lysates from some of the stably transfected cell lines and was compared with superoxide generation by the untransfected NIH 3T3 cell lysates. The results are shown in Table 4. Cell lines 26, 27, and 28 gave the highest degree of morphological changes by microscopic examination corresponding to the highest degree of superoxide generation. The luminescent signal was inhibited by superoxide dismutase and the general flavoprotein inhibitor diphenylene iodonium, but was unaffected by added recombinant human p47phox, p67phox and Rac1(GTP-γS), which are essential cytosolic factors for the phagocyte respiratory-burst oxidase.

TABLE 4

| Cell Line Name | Superoxide Generation (RLU) |
|---|---|
| Control (untransfected) | 6045 |
| mox1-26 | 17027 |
| mox1-27 | 14670 |
| mox1-28 | 18411 |
| mox1-65 | 5431 |
| mox1-615 | 11331 |
| mox1-+3 | 8645 |
| mox1-+10 | 5425 |
| mox1-pcc16 | 8050 |

In an alternate and preferred embodiment of the present invention, cells that had been stably transfected with mox1 (YA28) or with empty vector (NEF2) were grown in 10 cm tissue culture plates in medium containing DMEM, 10% calf serum, 100 units/ml penicillin, 100 µg/ml streptomycin, and 1 µg/ml puromycin to approximately 80% confluency. Cells (five tissue culture plates of each cell type) were washed briefly with 5 ml phosphate buffered saline (PBS) then dissociated from the plates with PBS containing 5 mM EDTA. Cells were pelleted by centrifuging briefly at 1000× g.

To permeabilize the cells, freeze thaw lysis was carried out and this was followed by passage of the cell material through a small bore needle. The supernatant was removed and the cells were frozen on dry ice for 15 minutes. After cells were thawed, 200 µl lysis buffer (HANKS' Buffered Salt Solution—HBBS) containing a mixture of protease inhibitors from Sigma (Catalog # P2714) was added. Cells on ice were passed through an 18 guage needle 10 times and 200 µl of HBSS buffer containing 34% sucrose was added to yield a final concentration of 17% sucrose. Sucrose appeared to enhance stability upon storage. The combination of freeze-thawing and passage through a needle results in lysis of essentially all of the cells, and this material is referred to as the "cell lysate."

The cell lysates were assayed for protein concentration using the BioRad protein assay system. Cell lysates were assayed for NADPH-dependent chemiluminescence by combining HBSS buffer, arachidonic acid, and 0.01–1 µg protein in assay plates (96 well plastic plates). The reaction was initiated by adding 1.5 mM NADPH and 75 µM lucigenin to the assay mix to give a final concentration of 200 µM NADPH and 10 µM lucigenin, and the chemiluminescence was monitored immediately. The final assay volume as 150 µl. The optimal arachidonic acid concentration was between 50–100 µM. A Packard Lumicount luminometer was used to measure chemiluminescence of the reaction between lucigenin and superoxide at 37° C. The plate was monitored continuously for 60 minutes and the maximal relative luminescence unit (RLU) value for each sample was used for the graph.

Figure 3:
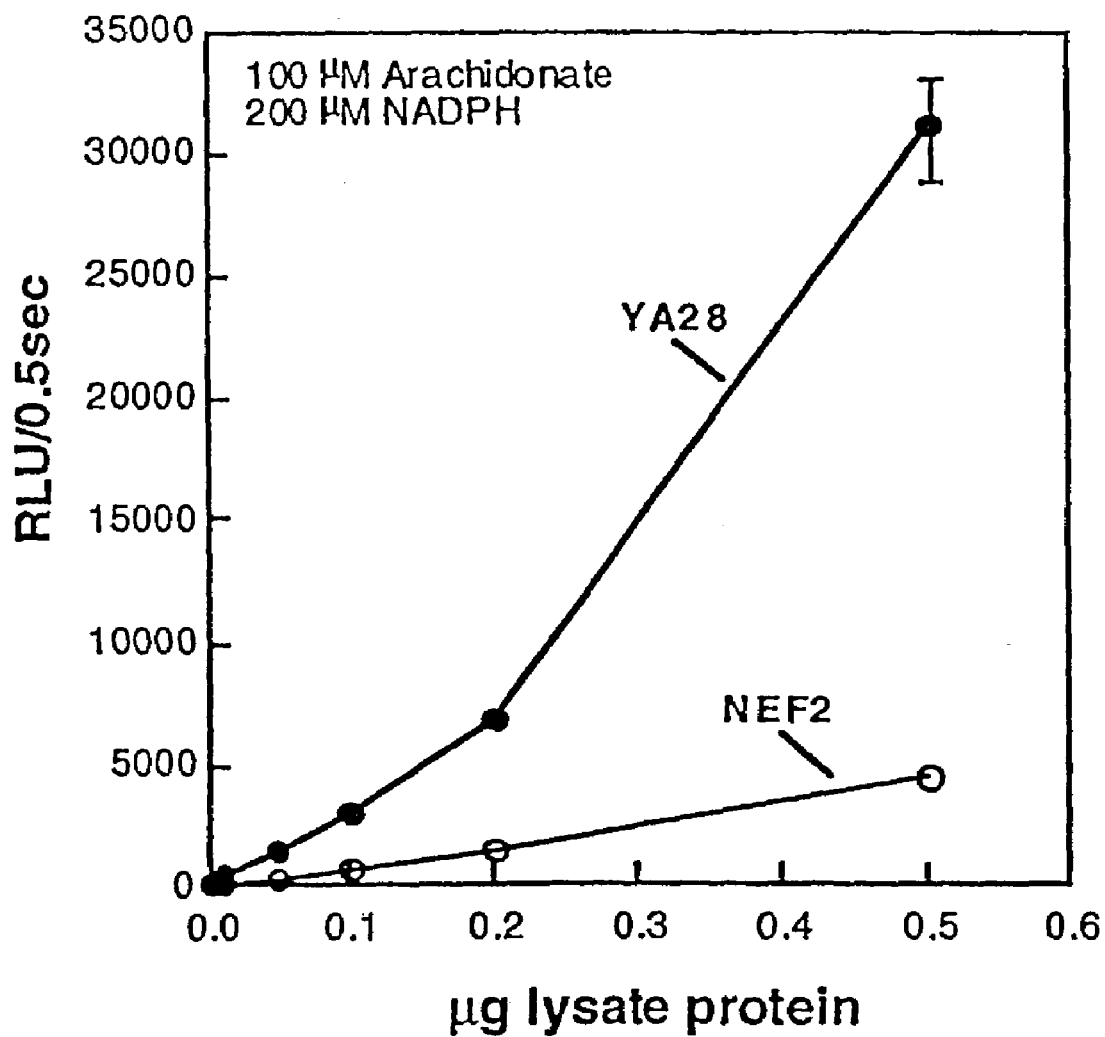
FIG. 3. Cell free assay for mox-1 activity. Superoxide generation was measured using the chemiluminescent reaction between lucigenin and superoxide in cell lysates from vector control NEF2 and mox1 transfected NIH3T3 cells.

FIG. 3 shows the RLU at various concentrations of cell lysates from mox1-transfected (YA28) and vector control (NEF2) cells. The presence of NaCl or KCl within a concentration range of 50–150 µM is important for optimal activity. $MgCl_2$ (1–5 mM) further enhanced activity by about 2-fold. This cell-free assay for mox1 NADPH-oxidase activity is useful for screening modulators (inhibitors or stimulators) of the mox1 enzyme. The assay may also be used to detect mox and duox NADPH-oxidase activity in general and to screen for modulators (inhibitors or stimulators) of the mox and duox family of enzymes.

EXAMPLE 7

Nitro Blue Tetrazolium Reduction by Superoxide Generated by NIH 3T3 cells Transfected with the Mox1 cDNA (SEQ ID NO:1)

Superoxide generation by intact cells was monitored by using superoxide dismutase-sensitive reduction of nitroblue tetrazolium. NEF2 (vector alone control), YA26 (mox1 (SEQ ID NO:1)-transfected) and YA28 (mox1 (SEQ ID NO:1)-transfected) cells were plated in six well plates at 500,000 cells per well. About 24 hours later, medium was removed from cells and the cells were washed once with 1 mL Hanks solution (Sigma, St. Louis, Mo.). About 1 mL of filtered 0.25% Nitro blue tetrazolium (NBT, Sigma) was added in Hanks without or with 600 units of superoxide dismutase (Sigma) and cells were incubated at 37° C. in the presence of 5% $CO_2$. After 8 minutes the cells were scraped and pelleted at more than 10,000 g. The pellet was re-suspended in 1 mL of pyridine (Sigma) and heated for 10 minutes at 100° C. to solubilize the reduced NBT. The concentration of reduced NBT was determined by measuring the absorbance at 510 nm, using an extinction coefficient of 11,000 $M^{-1}cm^{-1}$. Some wells were untreated and used to determine cell number.

Figure 4:
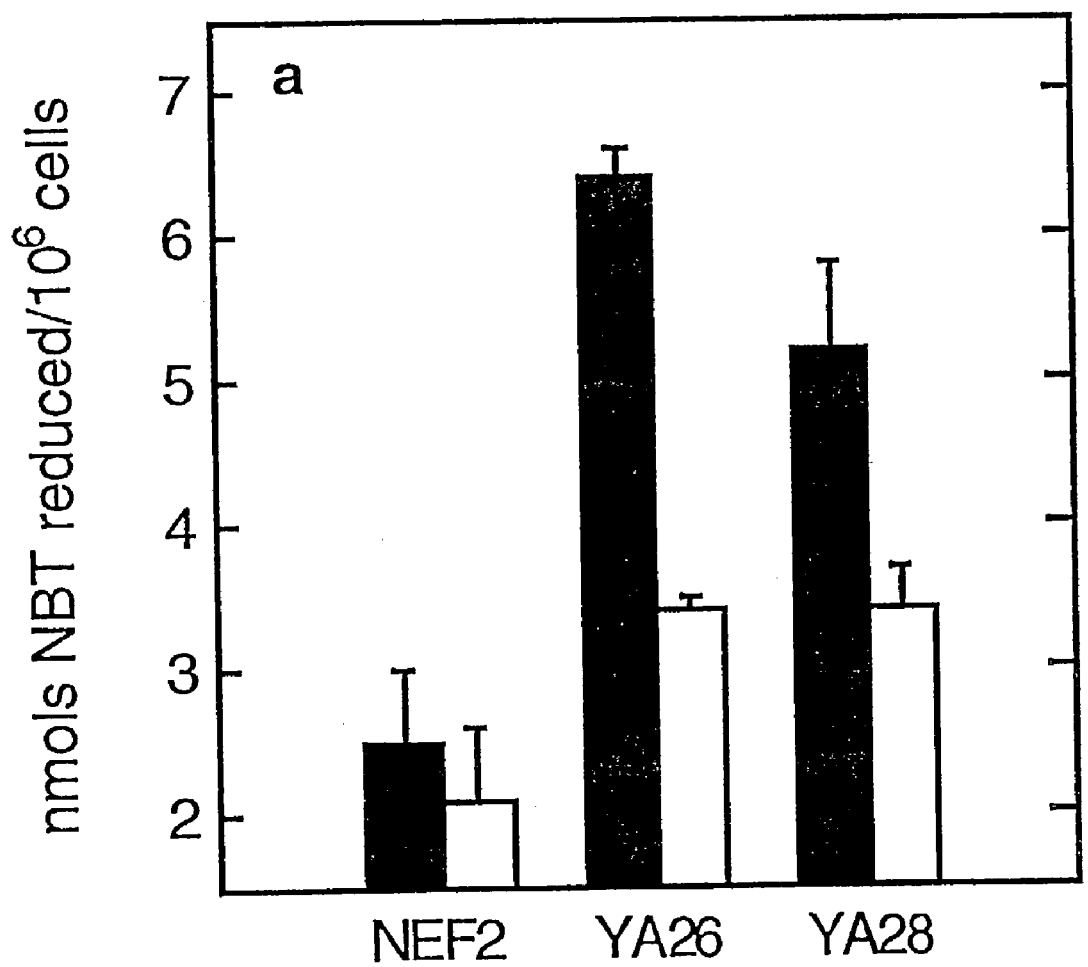
FIG. 4. Superoxide generation by human mox1. Reduction of NBT in mox1 transfected and control fibroblasts was measured in the absence (filled bars) or presence (open bars) or superoxide dismutase.

The data are presented in Table 5 and FIG. 4 and indicate that the mox1 (SEQ ID NO:1)-transfected cells generated significant quantities of superoxide.

TABLE 5

| NBT Reduction (nmols/$10^6$ cells) | −SOD | +SOD |
|---|---|---|
| vector control cells | 2.5 ± 0.5 | 2.1 ± 0.5 |
| YA26 (mox1) cells | 6.4 ± 0.2 | 3.4 ± 0.1 |
| YA28 (mox1) cells | 5.2 ± 0.6 | 3.4 ± 0.3 |

−SOD, and +SOD mean in the absence or presence of added superoxide dismutase, respectively.

Because superoxide dismutase is not likely to penetrate cells, superoxide must be generated extracellularly. The amount of superoxide generated by these cells is about 5–10% of that generated by activated human neutrophils.

EXAMPLE 8

Modification of Intracellular Components in Mox1 Transfected Cells

Figure 5:
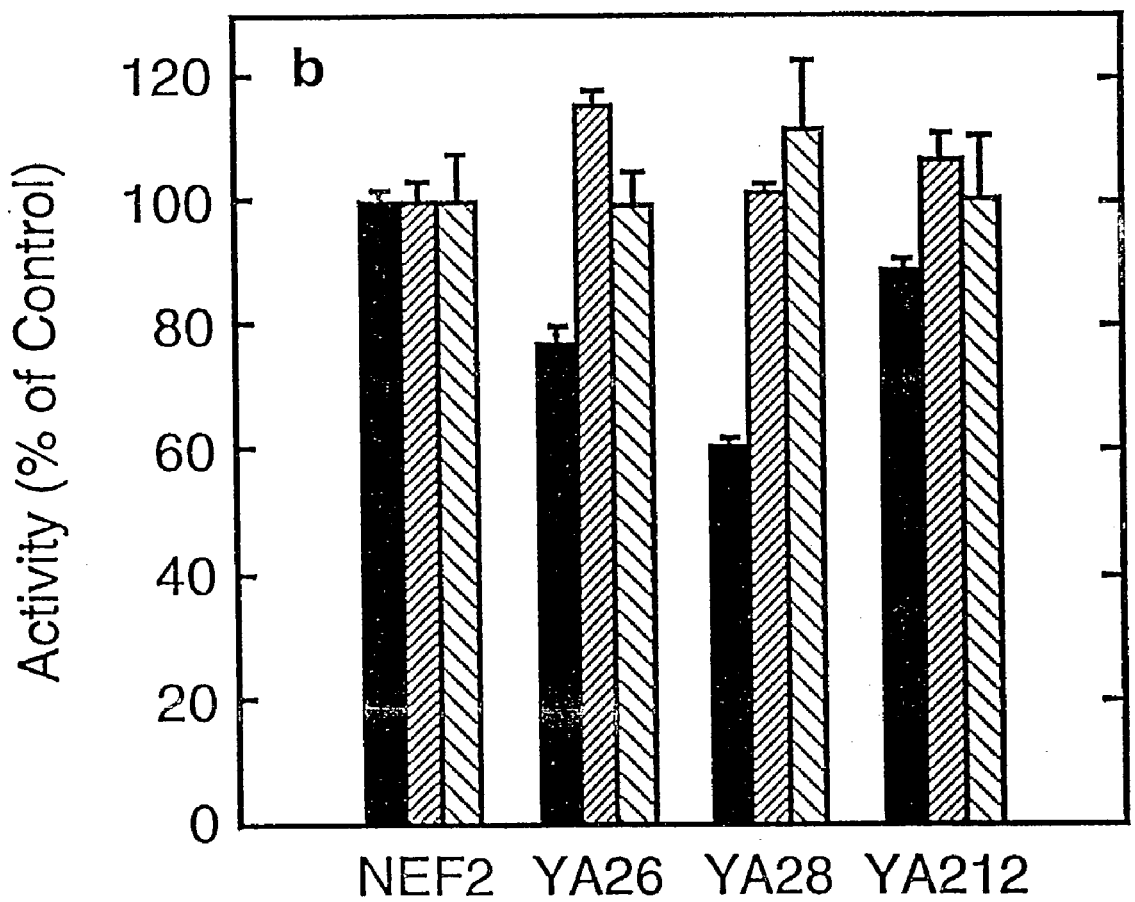
FIG. 5. Aconitase (filled bars), lactate dehydrogenase (narrow hatching) and fumarase (broad hatching) were determined in lysates of cells transfected with vector alone (NEF2) or with mox1 (YA26, YA28 and YA212).

To test whether superoxide generated by mox1 can affect intracellular "targets," aconitase activity in control and mox-transfected cell lines was monitored as described in Suh et al. (1999) *Nature* 401, 79–82. Aconitase contains a four-iron-sulphur cluster that is highly susceptible to modification by superoxide, resulting in a loss of activity, and has been used as a reporter of intra-cellular superoxide generation. Acotinase activity was determined as described in Gardner et al. (1995) *J. Biol. Chem.* 270, 13399–13405. Acotinase activity was significantly diminished in all three mox-transfected cell lines designated YA26, YA28 and YA212 as compared to the transfected control (FIG. 5). Approximately 50% of the aconitase in these cells is mitochondrial, based on differential centrifugation, and the cytosolic and mitochondrial forms were both affected. Control cytosolic and mitochondrial enzymes that do not contain iron-sulfur centres were not affected. Superoxide generated in mox1-transfected cells is therefore capable of reacting with and modifying intracellular components.

EXAMPLE 9

Tumor Generation in Nude Mice Receiving Cells Transfected with the Human mox1 cDNA (SEQ ID NO:1)

About $2\times10^6$ NIH 3T3 cells (either mox1-transfected with SEQ ID NO:1 or cells transfected using empty vector) were injected subdermally into the lateral aspect of the neck of 4–5 week old nude mice. Three to six mice were injected for each of three mox1-transfected cell lines, and 3 mice were injected with the cells transfected with empty vector (control). After 2 to 3 weeks, mice were sacrificed. The tumors were fixed in 10% formalin and characterized by histological analysis. Tumors averaged 1.5×1×1 cm in size and showed histology typical of sarcoma type tumors. In addition, tumors appeared to be highly vascularized with superficial capillaries. Eleven of twelve mice injected with mox1 gene-transfected cells developed tumors, while none of the three control animals developed tumors.

In another study, 15 mice were injected with mox1-transfected NIH 3T3 cells. Of the 15 mice injected, 14 showed large tumors within 17 days of injection, and tumors showed expression of mox1 mRNA. Histologically, the tumors resembled fibrosarcomas and were similar to ras-induced tumors. Thus, ras and mox1 were similarly potent in their ability to induce tumorigenicity of NIH 3T3 cells in athymic mice.

EXAMPLE 10

Demonstration of the Role of Mox1 in Non-Cancerous Growth

A role in normal growth was demonstrated in rat aortic vascular smooth-muscle cells by using antisense to rat mox1. Transfection with the antisense DNA resulted in a decrease in both superoxide generation and serum-dependent growth. Mox1 is therefore implicated in normal growth in this cell type.

EXAMPLE 11

Expression of Human Mox1 Protein (SEQ ID NO:2) in a Baculovirus Expression System SEQ ID NO:2 was also expressed in insect cells using recombinant baculovirus. To establish the p65mox1 expressing virus system, the mox1 gene (SEQ ID NO:1) was initially cloned into the pBacPAK8 vector (Clontech, Palo Alto, Calif.) and recombinant baculovirus was constructed using standard methods according to manufacturer's protocols. Briefly, PCR amplified mox1 DNA was cloned into the KpnI and EcoRI site of the vector. Primers used for PCR amplification were: 5'-CAA GGT ACC TCT TGA CCA TGG GAA ACT-3', SEQ ID NO:15, and 5'-ACG AAT TCA AGT AAA TTA CTG AAG ATA C-3', SEQ ID NO:16. Sf9 insect cells ($2\times10^6$ cells) were infected with 0.5 mg of linearized baculovirus DNA sold under the trademark BACULOGOLD® (PharMingen, San Diego, Calif.) and 5 mg pBacPAC8-p65mox1 using Transfection Buffers A and B (PharMingen, San Diego, Calif.). After 5 days, the supernatants containing recombinant viruses were harvested and amplified by infecting fresh sf9 cells for 7 days. Amplification was carried out three times and the presence of the recombinant virus containing mox1 DNA was confirmed by PCR using the same primers. After three times amplification of viruses, plaque purification was carried out to obtain the high titer viruses. Approximately $2\times10^8$ sf9 cells in agar plates were infected for 5 days with serial dilutions of virus and were dyed with neutral red for easy detection of virus plaques. Selected virus plaques were extracted and the presence of the human mox1 DNA was confirmed again by PCR.

EXAMPLE 12

Cloning of a Rat Homolog of p65mox (SEQ ID NO:2)

cDNA clones of p65mox from a rat aortic smooth muscle cell have been obtained. RT-PCR (reverse transcription polymerase chain reaction) was carried out as follows: first strand cDNA synthesis was performed using total RNA from rat aortic vascular smooth muscle cells, oligo dT primer and superscript II reverse transcriptase, and followed by incubation with RNase H. Degenerate PCR primers were designed to anneal to conserved areas in the coding regions of h-mox1 and gp91phox of human (X04011), mouse (U43384) and porcine (SSU02476) origin. Primers were: sense 5'-CCIGTITGTCGIAATCTGCTSTCCTT-3', SEQ ID NO:17 and antisense 5'-TCCCIGCAIAICCAGTA-GAARTAGATCTT-3', SEQ ID NO:18. A major PCR product of the expected 1.1 kb size was purified by agarose electrophoresis and used as template in a second PCR amplification reaction.

An aliquot of the RT-PCR product was blunt-ended, ligated into a modified Litmus 29 vector and used to transform XL10 competent *E. coli*. Approximately 120 bacterial colonies were screened for the presence of a full-length insert by direct PCR using vector primers and Taq polymerase. Plasmids were purified from 25 positive colonies and mapped by digestion with Bam HI. Representative plasmids from each digestion pattern were partially sequenced. Five out of 25 clones contained non-specific amplification products and 20 contained identical inserts similar to human (h)-mox1. One of the latter clones was fully sequenced and found to be 83% identical to h-mox1 over 1060 nucleotides. A 1.1 kb probe was generated by PCR amplification of the insert of a rat mox1 clone with the degenerate primers described above and used to hybridize to a Northern blot of rat vascular smooth muscle cell RNA. A single band, migrating between 28S rRNA and 18S rRNA, indicated the presence of a message with a size compatible to that of human mox-1 (2.6 kb).

To obtain full-length rat mox1, 3' and 5' rapid amplification of cDNA ends (RACE) reactions were performed as describe above, using the gene-specific primers 5'-TTG-GCACAGTCAGTGAGGATGTCTTC-3', SEQ ID NO:19 and 5'-CTGTTGGCTTCTACTGTAGCGTTCAAAGTT-3', SEQ ID NO:20 for 3' and 5' RACE, respectively. Single major 1.5 kb and 850 bp products were obtained for 3' and 5' RACE, respectively. These products were purified by agarose gel eletrophoresis and reamplified with Taq polymerase. Both products were cloned into the pCR 2.1 vector and used to transform electrocompetent XL1 blue *E. coli*. The RACE products were sequenced and new terminal primers were designed: sense 5'-TTCTGAGTAGGTGTG-CATTTGAGTGTCATAAAGAC-3' (SEQ ID NO:43), and antisense 5'-TTTTCCGTCAAAATTATAACTTTT-TATTTTCTTTTTATAACACAT-3' (SEQ ID NO:44). PCR amplification of rat VSMC cDNA was performed using these primers.

A single 2.6 kb product was obtained, ligated into pCR 2.1 and used to transform electrocompetent XL1 blue *E. coli*. The insert was sequenced with 12 sense and 14 antisense primers. Its length is 2577 bp (including primer sequences), comprising a 1692 bp open reading frame, 127 bp 5' and 758 bp 3' untranslated regions. The presence of six in-frame stop codons in the 5' untranslated region suggests that the full length coding region has been obtained. Consensus polyadenylation sequences are present at nucleotides 2201 and 2550. Conceptual translation yields a 563 amino acid peptide, one residue shorter than the human deduced sequence. This new amino acid sequence is more similar to human mox1 SEQ ID NO:3 (82% identity) than to mouse gp91phox SEQ ID NO:38 (55% identity), suggesting that it is indeed rat mox1 (SEQ ID NO:21). This rat (r) homolog of p65mox protein is called r-p65mox or p65mox/rat.pep and is shown as SEQ ID NO:21. The nucleotide sequence encoding for r-p65mox is shown as SEQ ID NO:22

EXAMPLE 13

Expression of rat (r)-p65mox mRNA in Vascular Smooth Muscle and Induction by Angiotensin II, Platelet-Derived Growth Factor (PDGF), and Phorbol Myristic Acid (PMA)

Using the partial cDNA clone from rat, we have examined cultured rat aortic smooth muscle cells for expression of message for r-p65mox. We have observed the mRNA for r-p65mox in these cells. It has been previously reported (Griendling et al. (1994) Circ. Res. 74, 1141–1148; Fukui et al. (1997) Circ. Res. 80, 45–51; Ushio-Fukai et al. (1996) J. Biol. Chem. 271, 23317–23321) that in vitro or in vivo treatment with angiotensin II (AII) is a growth stimulus for vascular smooth muscle cells, and that AII induces increased superoxide generation in these cells. Platelet-derived growth factor (PDGF) and PMA are proliferative signals for vascular smooth muscle cells. We observed that the mRNA for r-p65mox was induced approximately 2–3 fold by angiotensin II (100 nM), corresponding to the increased level of superoxide generation. Thus, the increased superoxide generation in these cells correlates with increased expression of the mRNA for this enzyme. The mRNA for r-p65mox also increased 2 or more fold in response to the growth stimulus PDGF (20 ng/ml), and 2–3 fold in response to PMA. Quantitation by densitometry revealed that rat mox1 message was induced nearly 4-fold at the 6 and 12 hour time points in response to PDGF, and about 2-fold at the 12 hour time point in response to AII. 28S RNA was used as a control for RNA recovery.

EXAMPLE 14

Antibodies to Fragments of Human (h)-p65mox (SEQ ID NO:2)

Polyclonal antibodies were raised in rabbits against the C-terminal half of h-p65mox (residues 233 through 564, SEQ ID NO:23) which is predicted to fold into a cytosolic domain containing FAD and the NADPH or NADH binding site. This domain was expressed in *E. coli* as an N-terminal GST-fusion protein and was purified on glutathione agarose by standard methods. Two antipeptide antibodies were also made against h-p65mox (residues 243–256, referred to as Peptide A, SEQ ID NO:24) and h-65mox (residues 538–551, referred to as Peptide B, SEQ ID NO:25). Peptides were conjugated to keyhole limpet hemocyanin (KLH) using glutaraldehyde.

Antigens were injected into different rabbits initially in complete Freund's adjuvant, and were boosted 4 times with antigen in incomplete Freund's adjuvant at intervals of every three weeks. Approximately 0.5 mg to 1 mg of peptide was administered at each injection. Blood was drawn 1 week after each boost and a terminal bleed was carried out 2 weeks after the final boost. Antibodies to Peptide A and Peptide B were affinity purified by column chromatography through peptide A or peptide B conjugated to Affigel 15 (BioRad, Richmond, Calif.). 10 mg of peptide was covalently crosslinked to 2 ml of Affigel 15 resin and the gel was washed with 20 ml of binding buffer (20 mM Hepes/NaOH, pH 7.0, 200 mM NaCl, and 0.5% Triton X-100). The remaining functional N-hydrosuccinimide was blocked with 100 µl of 1 M ethanolamine. After washing with 20 ml of binding buffer, 5 ml of the antiserum was incubated with the pep A-conjugated Affigel 15 resin overnight at 4° C. Unbound protein was washed away with 20 ml of binding buffer. Elution of the antibodies from the gel was performed with 6 ml of elution buffer (100 mM glycine/HCl, pH 2.5, 200 mM NaCl, and 0.5% Triton X-100). The eluate was then neutralized by adding 0.9 ml of 1 M Tris/HCl, pH 8.0. The GST-fusion form of truncated p65mox1 protein (residues 233–566, SEQ ID NO:23) was expressed in *E. coli*. Samples (20 µg each) were run on 12% SDS-PAGE either before or 1 or 4 hours after induction with 100 µM IPTG (isopropyl β-thiogalactoside).

The extracted proteins were subjected to immunoprobing with affinity purified antiserum to peptide A at a 1:1000 dilution. The detection of antigens was performed using an enhanced chemiluminescence kit (Amersham, Buckinghamshire, UK). The affinity purified antibody to mox1 (243–256, SEQ ID NO:24) was used at a dilution of 1:1000 in a Western blot in which a total of 10 µg of protein was added to each lane. The major band observed at 4 hours after IPTG induction corresponded to the size of the GST-mox1 expressed in bacteria containing the pGEX-2T vector encoding the GST-mox1 fusion protein.

Example 15

Presence of an NAD(P)H Oxidase in Ras-Transformed Fibroblasts

A superoxide-generating NADPH oxidase activity was detected in homogenates from NIH 3T3 cells, and this activity increased about 10–15 fold in Ras-transformed NIH 3T3 cells (Table 6). To establish the stable Ras-transformed cell lines, the DNA for human Ras encoding an activating mutation at amino acid number 12 (Valine, referred to as V12-Ras) was subcloned into BamH1 and EcoR1 sites of pcDNA3 vector which has a neomycin resistance gene. V12-Ras in pcDNA3 and empty vector were transfected into NIH 3T3 cells using Lipofectamine Plus (Gibco). $2 \times 10^6$ cells were maintained with DMEM containing 10% calf serum and transfected with 1 mg of DNA. After 2-days, cells were split and selected with the same medium but containing 1 mg/ml neomycin. Colonies surviving in selection media for 10 to 14 days were sub-cultured and characterized by immunoblot analysis using antibody against human H-Ras.

The expression of Ras in cells transfected with pcDNA-3 vector alone or in three cell lines transfected with V12-Ras in the same vector was analyzed on a Western blot. The three cell lines were named V12-Ras-7, V12-Ras-4, and V12-Ras-8. The expression of V12-Ras varied widely among the three cell lines tested. The V12-Ras-4 cell line expressed the highest level of Ras followed by the V12-Ras-8 cell line. The V12-Ras-7 cell line expressed the lowest level of Ras.

Lysates from each of these lines were then prepared and tested for their ability to generate superoxide. For each cell line, cells were washed with cold HANKS' balanced salt solution (HBSS), collected by centrifugation, kept on dry-ice for more than 30 min, and disrupted by suspending in low salt buffer (LSB; 50 mM Tris/HCl, pH 7.5, 1 mM PMSF, and protease cocktail from Sigma) and passing through a syringe needle (18 gauge) ten times. Cell lysates were frozen in dry-ice immediately after determining the protein concentration.

Table 6 shows superoxide generation in the transfected cells measured using the lucigenin luminescence assay. For the assay, 5 µg of cell lysates were incubated with the reaction mixture containing 10 µM lucigenin (luminescent probe) and 100 µM NADPH (substrate) in the presence or absence of 100 µM arachidonate in the absence or presence of 100 U of superoxide dismutase (SOD) or 1 µM diphenyleneiodonium (DPI). Luminescence of the reaction mixture was monitored for 0.5 second by LumiCounter (Packard) for four times at 3 second intervals. RLU in Table 5 refers to relative luminescence units.

As shown in Table 6, the luminescence was partially inhibited by superoxide dismutase indicating that the signal was due at least in part to the generation of superoxide. DPI, a known inhibitor of both neutrophil and non-neutrophil. NADPH oxidase activities, completely inhibited activity. The generation of superoxide correlated with the expression of Ras in the three cell lines. Thus, oncogenic Ras appears to induce an NADPH-dependent superoxide generating activity that is similar to the activity catalyzed by p65mox1.

TABLE 6

| | RLU/5 µg protein | | |
| --- | --- | --- | --- |
| | no additions | plus SOD | plus DPI |
| Vector Control (1) | 465 | 154 | 48 |
| V12-Ras-7 (2) | 1680 | 578 | 39 |
| V12-Ras-4 (3) | 5975 | 2128 | 36 |
| V12-Ras-8 (4) | 4883 | 2000 | 35 |

EXAMPLE 16

Molecular Cloning of Another Rat mox1 cDNA Called Rat mox1B

A rat cDNA library was screened in an effort to identify new rat mox sequences. The library was constructed in a ZAP express lambda phage vector (Stratagene, La Jolla, Calif.) using RNA isolated from rat vascular smooth muscle cells which had been exposed to 100 nM angiotensin II for 4 hours. The library was screened using standard blot hybridization techniques with the rat mox1 probe described previously. Fifteen individual clones were obtained that were characterized by PCR and restriction mapping. Two different types of clones were thus identified and representatives of each type were sequenced. A clone of the first type (representative of 13) was found to be similar to the previously identified rat mox1 and was thus named rat mox1B. Clones of the second type (representative of 2) were incomplete rat mox sequences.

The length of the rat mox1B nucleotide sequence is 2619 bp and is listed as SEQ ID NO:41. The single longest 1497 bp open reading frame encompasses nucleotides 362 to 1858. The presence of two in-frame stop codons in the 5' untranslated region at nucleotides 74 and 257 indicates that the full-length coding region has been isolated. Two putative polyadenylation sites are present at positions 2243 and 2592. Alignment of the rat mox1 nucleotide sequence (SEQ ID NO:22) and the rat mox1B nucleotide sequence (SEQ ID NO:41) shows that the two nucleotides sequences are identical except at their 5' ends, suggesting that they may represent two alternatively spliced messages from the same gene. Sequence identity starts at nucleotides 269 and 311, for rat mox1 and rat mox1B, respectively.

Conceptual translation of the rat mox1B nucleotide sequence (SEQ ID NO:41) yields a 499 amino acid sequence with a predicted molecular weight of 58 kDa. This amino acid sequence for rat mox1B protein is shown in SEQ ID NO:42. Alignment of the deduced amino acid sequences for rat mox1 (SEQ ID NO:21) and rat mox1B (SEQ ID NO:42) indicates that rat mox1B is identical to rat mox1A, except for a missing stretch of 64 residues at the N-terminus. Therefore, rat mox1B appears to be a splicing variant derived from the same gene as rat mox1.

EXAMPLE 17

Sequence Analysis and Cloning of the Human Mox2 cDNA (SEQ ID NO:3) Encoding for Production of the Human Mox2 Protein (SEQ ID NO:4)

Note that the mox2 protein as described herein, was described in U.S. Provisional Application Ser. No. 60/149,332 as mox3.

A blast search was carried out using the sequence of mox1 as a query sequence. The sequence identified by this search was a sequence present in the GenBank database that contains regions of homology with mox1 and gp91phox. The GenBank sequence located in the search was a 90.6 kb sequenced region of human chromosome 6 (6q25.1–26) that was reported as a GenBank direct submission dated Feb. 9, 1999 and given the Accession No. AL031773. Sequencing was carried out as part of the human genome sequencing project by S. Palmer, at Sanger Centre, in Hinxton, Cambridgeshire, UK. The GenBank sequence was reported as being similar to "Cytochrome B" and was not reported as having any homology or relation to a mox protein. The sequence contained a theoretical amino acid sequence that was derived by computer using an algorithm that predicted intron/exon boundaries and coding regions. This predicted region contained a 545 amino acid sequence that was 56% identical to mox1 and 58% identical to gp91phox.

In the present invention, based on the GenBank genomic sequence and the homologies described above, several specific primers were designed and used to determine the tissue expression patterns of a novel mox protein, mox2, using Human Multiple Tissue PCR Panels (Clontech, Palo Alto, Calif.). The primers were as follows: Primer 1: 5'-CCTGA-CAGATGTATTTCACTACCCAG-3' (SEQ ID NO:49); Primer 2: 5'-GGATCGGAGTCACTCCCTTCGCTG-3' (SEQ ID NO:50); Primer 3: 5'-CTAGAAGCTCTCCTTGT-TGTAATAGA-3' (SEQ ID NO:51); Primer 4: 5'-ATGAA-CACCTCTGGGGTCAGCTGA-3' (SEQ ID NO:52). It was determined that mox2 is expressed primarily in fetal tissues, with highest expression in fetal kidney, with expression also seen in fetal liver, fetal lung, fetal brain, fetal spleen and fetal thymus. Among 16 adult tissues tested, mox2 expression was seen in brain, kidney, colon and lung, although levels of expression appeared to be very low.

Additionally, the 5' RACE (RACE=Rapid Amplification of cDNA Ends) and 3' RACE techniques were used to complete the sequence of the 5' and 3' regions of mox2. (5' RACE kit and 3' RACE kit were from Clontech, Palo Alto, Calif. and are more fully described in Frohman et al. (1988) *Proc. Natl. Acad. Sci. USA* 85, 8998–9002. The 5' RACE and 3'-RACE techniques were carried out using a human fetal kidney library (Marathon-Ready cDNA library, Cat. #7423-1), using the following specific primers: 5'-RACE: Primer 4: 5'-ATGAACACCTCTGGGGTCAGCTGA-3' (SEQ ID NO:53); Primer 5: 5'-GTCCTCTGCAGCATTGT-TCCTCTTA-3' (SEQ ID NO:54); 3'-RACE: Primer 1: 5'-CCTGACAGATGTATTTCACTACCCAG-3' (SEQ ID NO:55); Primer 2: 5'-GGATCGGAGTCACTCCCT-TCGCTG-3' (SEQ ID NO:56). The RACE procedures were successful in completing the 5' sequence and in confirming the 3' sequence. The complete coding sequence of mox2 is shown in SEQ ID NO:2, while the predicted amino acid sequence of mox2 is shown in SEQ ID NO:4.

In comparing the sequences of the present invention to the predicted coding regions of the GenBank sequence, the GenBank sequence did not contain a start codon, appeared to be missing approximately 45 base pairs at the N-terminus, and contained one other major difference in the predicted coding region which could have been due to inaccurate computer prediction of intron/exon boundaries.

EXAMPLE 18

Sequence Analysis and Partial Cloning of the Human Duox2 cDNA (SEQ ID NO:47) Encoding for Production of the Human Duox2 Protein (SEQ ID NO:48)

A partial cDNA clone of duox2 was obtained as follows. A 535-base portion of an expressed sequence tag (EST zc92h03.rl; Genbank accession no. W52750) from human pancreatic islet was identified using the human gp91phox amino-acid sequence as a query in a Blast search. The bacterial strain #595758 containing the EST sequence zc92h03.rl in the pBluescript SK-vector was purchased from ATCC (Rockville, Md.). The DNA inserted into the pBluescript SK-vector was further sequenced using T7 and T3 vector promoters as well as sequence specific internal primers. The EST encoded 440 amino acids showing a 24.4% identity to gp91phox, including a stop codon corresponding to the C-terminus of gp91phox. 5'-RACE was carried out using mRNA obtained from human colon carcinoma cells (CaCo2) and the Marathon cDNA Amplification Kit (Clon-Tech, Palo Alto). The following gene-specific primers were used for this procedure: 5'-GAAGTGGTGGGAGGCGAA-GACATA-3' (SEQ ID NO:26) and 5'-CCTGTCATAC-CTGGGACGGTCTGG-3' (SEQ ID NO:27).

The results of the 5'-RACE yielded an additional 2 kilobase of sequenced DNA but this region did not contain the start codon. To complete the sequence of the 5' and 3' regions of duox2, 5'-RACE and 3'-RACE were carried out using a human adult pancreas mRNA (Clontech, Palo Alto, Calif.) with the kit of 5' RACE System for Rapid Amplification of cDNA Ends version 2.0 (Gibco BRL, Gaithersburg, Md.). PCR done using the following specific primers resulted in a total predicted amino acid sequence of about 1000 residues:

```
5'-RACE: Primer 3:                    (SEQ ID NO:28)
5'-GAGCACAGTGAGATGCCTGTTCAG-3';

Primer 4:                             (SEQ ID NO:29)
5'-GGAAGGCAGCAGAGAGCAATGATG-3' (for nested PCR);
```

-continued

3'-RACE Primer 5: (SEQ ID NO:30)
5'-ACATCTGCGAGCGGCACTTCCAGA-3'

Primer 6: (SEQ ID NO:31)
5'-AGCTCGTCAACAGGCAGGACCGAGC-3' (for nested PCR).

EXAMPLE 19

Sequence Analysis and Cloning of the Human Duox1 cDNA (SEQ ID NO:45) Encoding for Production of the Human Duox1 Protein (SEQ ID NO:46)

A cDNA clone of duox1 was obtained as follows. A homologous 357-base portion of an expressed sequence tag (EST nr80d12.s1; Genbank accession no. AA641653) from an invasive human prostate was identified by using the partial duox2 predicted amino-acid sequence described above as a query in a Blast search. The bacterial strain #1441736 containing the EST sequence nr80d12.s1 in the pBluescript SK-vector was purchased from ATCC (Rockville, Md.). The DNA inserted into the pBluescript SK-vector was further sequenced using T7 and T3 vector promoters as well as sequence specific internal primers. The EST insert encoded 673 amino acids with no start or stop codons present. Northern Blot analysis of duox1 indicated the gene was about 5.5 kilobase pairs. To complete the sequence of 5' and 3' regions of duox1, 5' RACE and 3'-RACE were carried out using a human adult lung mRNA (Clontech, Palo Alto, Calif.) with the kit of 5' RACE System for Rapid Amplification of cDNA Ends version 2.0 (Gibco BRL, Gaithersburg, Md.). The RACE procedure was carried out using the following specific primers: 5'-RACE: Primer 5: 5'-GCAGTGCATCCACATCTTCAGCAC-3' (SEQ ID NO:32); Primer 6: 5'-GAGAGCTCTGGAGACACT-TGAGTTC-3' (SEQ ID NO:33) (for nested PCR); 3'-RACE Primer 7: 5'-CATGTTCTCTCTGGCTGACAAG-3' (SEQ ID NO:34); Primer 8: 5'-CACAATAGCGAGCTCCGCT-TCACGC-3' (SEQ ID NO:35) (for nested PCR). RACE procedures were successful in completing the 5' sequence and the 3' sequence of duox1. The open reading frame is approximately 4563 base pairs.

EXAMPLE 20

Tissue Expression of Duox1 and Duox2

Based on the duox1 sequence data, several specific primers were designed (Primer 1 a: 5'-GCAGGACATCAAC-CCTGCACTCTC-3' (SEQ ID NO:36); Primer 2a: 5'-AAT-GACACTGTACTGGAGGCCACAG-3' (SEQ ID NO:57); Primer 3a: 5'-CTGCCATCTACCACACGGATCTGC-3' (SEQ ID NO:58); Primer 4a: 5'-CTTGCCATTC-CAAAGCTTCCATGC-3' (SEQ ID NO:59) and used these to determine the tissue expression patterns of duox1 using Human Multiple Tissue PCR Panels (Clontech, Palo Alto, Calif.). It was determined that duox1 is expressed primarily in lung, testis, placenta, prostate, pancreas, fetal heart, fetal kidney, fetal liver, fetal lung, fetal skeletal muscle and thymus, with highest expression in adult and fetal lung. Among 16 adult tissues and 8 fetal tissues tested, duox1 expression in brain, heart, kidney, colon, ovary, thymus, fetal brain and fetal spleen appeared to be low.

Two duox2 specific primers were also used to determine the tissue expression patterns of duox2 using Human Multiple Tissue PCR (polymerase chain reaction) Panels (Clontech, Palo Alto, Calif.). (Primer 1b: 5'-GTACAAGTCAG-GACAGTGGGTGCG-3' (SEQ ID NO:60); Primer 2b: 5'-TGGATGATGTCAGCCAGCCACTCA-3' (SEQ ID NO:61)). Duox2 is expressed primarily in lung, pancreas, placenta, colon, prostate, testis and fetal tissues, with highest expression in adult lung and fetal tissues. Among 16 adult tissues and 8 fetal tissues tested, duox2 expression in brain, heart, kidney, liver, skeletal muscle, thymus and fetal brain appeared to be low.

EXAMPLE 21

Role of Duox1 and Duox2 in Collagen Crosslinking

To investigate a possible role for the human duox1 and duox2, the model organism *Caenorhabditis elegans* and a new reverse genetic tool, RNA interference (RNAi), were used to "knock out" the homologues of duox in this organism (Fire et al. (1998) *Nature* 391, 806–811). This technique involved injection of double stranded RNA encoding a segment of Ce-duox1 or Ce-duox2 into gonads of *C. elegans* N2 hermaphrodites. Injected worms were then allowed to lay eggs, and the harvested eggs were allowed to develop and the F1 progeny were scored for phenotypes. This procedure has been documented to "knock-out" the expression of the gene of interest (Fire et al. (1998) *Nature* 391, 806–811).

In the case of Ce-duox1 and Ce-duox2, the knockout animals resulted in a complex phenotype including worms with large superficial blisters, short or "dumpy" worms, worms with locomotion disorders, and worms with retained eggs and/or larvae. Because of the high identity between Ce-duox1 and Ce-duox2, three different RNA constructs were predicted to knock out either both genes or Ce-duox2 alone. In all cases, essentially the same group of phenotypes was obtained. Most or all of these phenotypes had been described previously in *C. elegans* mutated in the collagen biosynthetic pathway. *C. elegans* has an extracellular structure known as the cuticle, a complex sheath composed largely of cross-linked collagen, which functions as the exoskeleton of the nematode. Cross-linking of collagen in nematodes occurs in part by cross-linking tyrosine residues, and peroxidases such as sea urchin ovoperoxidase and human myeloperoxidase have previously been shown to be capable of carrying out this reaction.

Based upon the similarities of the phenotypes obtained, the Ce-duox1/2 knockout worms were examined for the presence of dityrosine linkages, using an HPLC methodology (Andersen, S. O. (1966) *Acta Physiol. Scand.* 66, Suppl. 263–265; Abdelrahim et al. (1997) *J. Chromatogr. B Biomed. Sci. Appl.* 696, 175–182). It was determined that dityrosine linkages, while easily detected in the wild type worms, were almost completely lacking in the knockout worms. Thus, an inability to catalyze dityrosine cross-linking accounts for the phenotype of *C. elegans* failing to express Ce-duox1/2. These data support the concept that the duox enzymes in higher organisms can probably function in a similar manner to modulate the extracellular milieu, possibly the extracellular matrix and/or the basement membrane.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. An isolated nucleic acid encoding a protein comprising the amino acid sequence set forth in SEQ ID NO: 46, or a fragment of SEQ ID NO: 46 wherein the fragment has enzymatic activity of generating reactive oxygen intermediates.

2. The isolated nucleic acid of claim 1, wherein the nucleic acid comprises the nucleotide sequence set forth in SEQ ID NO:45.

3. A vector, comprising the nucleic acid of claim 1.

4. The vector of claim 3, comprising a nucleic acid having the nucleotide sequence set forth in SEQ ID NO:45.

5. An isolated cell comprising the vector of claim 3.

6. An isolated cell comprising the vector of claim 4.

7. The isolated nucleic acid of claim 1, wherein the nucleic acid encodes a protein comprising the amino acid sequence set forth in SEQ ID NO: 46.

8. The isolated nucleic acid of claim 1, wherein the nucleic acid a protein consisting of the amino acid sequence set forth in encodes SEQ ID NO: 46.

9. The isolated nucleic acid of claim 1, wherein the nucleic acid encodes a fragment of SEQ ID NO: 46 wherein the fragment has enzymatic activity of generating reactive oxygen intermediates.

* * * * *

UNITED STATES PATENT AND TRADEMARK OFFICE
CERTIFICATE OF CORRECTION

PATENT NO. : 7,045,351 B2
APPLICATION NO. : 10/318906
DATED : May 16, 2006
INVENTOR(S) : Lambeth et al.

It is certified that error appears in the above-identified patent and that said Letters Patent is hereby corrected as shown below:

<u>In the Specification:</u>
In column 14, line 44, "(O)" should be --(Q)--
In column 16, line 53, please insert a period after the word "thereof" to read --thereof.--
In column 23, line 21, the word "LST176696" should be --EST176696--

<u>In the Claims:</u>
In Claim 8, the phrase "acid a" should be --acid encodes a--
In Claim 8, the phrase "in encodes SEQ" should be --in SEQ--

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.       : 7,045,351 B2  
APPLICATION NO.  : 10/318906  
DATED            : May 16, 2006  
INVENTOR(S)      : Lambeth et al.

Page 1 of 1

It is certified that error appears in the above-identified patent and that said Letters Patent is hereby corrected as shown below:

In the Specification:
In column 14, line 44, "(O)" should be --(Q)--  
In column 16, line 53, please insert a period after the word "thereof" to read --thereof.--  
In column 23, line 21, the word "LST176696" should be --EST176696--

In the Claims:
Column 124, line 58, In Claim 8, the phrase "acid a" should be --acid encodes a--  
Column 124, line 59, In Claim 8, the phrase "in encodes SEQ" should be --in SEQ--

This certificate supersedes the Certificate of Correction issued June 17, 2008.

Signed and Sealed this

Fifteenth Day of July, 2008

JON W. DUDAS  
*Director of the United States Patent and Trademark Office*